United States Patent
Wu et al.

(10) Patent No.: US 11,913,939 B2
(45) Date of Patent: Feb. 27, 2024

(54) COMPARTMENTALIZED ASSAYS OF BISPECIFIC AND MULTISPECIFIC BIOLOGICS

(71) Applicant: Amberstone Biosciences, Inc., Laguna Hills, CA (US)

(72) Inventors: George Guikai Wu, Laguna Hills, CA (US); Yonglei Shang, Laguna Hills, CA (US)

(73) Assignee: Amberstone Biosciences, Inc., Laguna Hills, CA (US)

( * ) Notice: Subject to any disclaimer, the term of this patent is extended or adjusted under 35 U.S.C. 154(b) by 0 days.

(21) Appl. No.: 17/221,688

(22) Filed: Apr. 2, 2021

(65) Prior Publication Data
US 2021/0293782 A1    Sep. 23, 2021

Related U.S. Application Data

(63) Continuation of application No. PCT/US2019/055047, filed on Oct. 7, 2019.
(Continued)

(51) Int. Cl.
*G01N 33/50* (2006.01)
*G01N 33/53* (2006.01)
*B01L 3/00* (2006.01)

(52) U.S. Cl.
CPC ...... *G01N 33/502* (2013.01); *B01L 3/502761* (2013.01)

(58) Field of Classification Search
CPC ............ G01N 33/502; G01N 33/5436; G01N 33/6845; B01L 3/502761; C12N 15/1075; C12N 15/1034
See application file for complete search history.

(56) References Cited

U.S. PATENT DOCUMENTS

| 8,415,173 B2 | 4/2013 | Harriman |
| 2005/0266425 A1* | 12/2005 | Zauderer ............ C07K 16/2866 435/6.14 |

(Continued)

FOREIGN PATENT DOCUMENTS

| CN | 107810413 A | 3/2018 |
| JP | 2015529826 A | 10/2015 |

(Continued)

OTHER PUBLICATIONS

Patterson "Chemically generated IgG2 bispecific antibodies through disulfide briding" (Bioorganic & Medicinal Chemistry Letters 2017 27:3647-3652). (Year: 2017).*

(Continued)

*Primary Examiner* — Changhwa J Cheu
(74) *Attorney, Agent, or Firm* — Knobbe Martens Olson & Bear LLP

(57) ABSTRACT

Methods and systems for performing assays in compartmentalized nano-volumes to screen for functional bispecific or multispecific biologics, including: providing a plurality of at least two distinct types of cells, wherein two or more first-type cells are engineered to express substantially a single genetic-variant per cell for a bispecific or multispecific biologic in a secreted form, wherein two or more second-type cells are selected or engineered to produce a positive reporter molecule signal that is triggered by a functional variant of the said biologic expressed by a first-type cell; providing a plurality of compartmentalized nano-volumes, wherein two or more nano-volumes are each provided with substantially one first-type cell, and one or more second-type cell(s); incubating the said nano-volumes over a period of time to allow the expression and secretion of the said biologics inside the said nano-volumes; collecting data representing the positive reporter molecule signal triggered by secreted biologics inside the said nano-vol- (Continued)

umes, and recovering cells from the nano-volumes with the positive reporter molecule signal and extracting the genetic information representing respective functional variants of the biologics.

27 Claims, 29 Drawing Sheets

Specification includes a Sequence Listing.

Related U.S. Application Data

(60) Provisional application No. 62/784,171, filed on Dec. 21, 2018, provisional application No. 62/742,837, filed on Oct. 8, 2018.

(56) References Cited

U.S. PATENT DOCUMENTS

| | | | | |
|---|---|---|---|---|
| 2011/0275063 | A1* | 11/2011 | Weitz | G01N 33/5436 |
| | | | | 435/7.1 |
| 2013/0130379 | A1* | 5/2013 | Adams | C07K 16/2866 |
| | | | | 435/69.6 |
| 2016/0102280 | A1* | 4/2016 | Tovar | C12M 25/01 |
| | | | | 435/3 |
| 2016/0215282 | A1* | 7/2016 | Lin | C07K 16/00 |
| 2016/0231324 | A1* | 8/2016 | Zhao | G01N 33/54366 |
| 2017/0296678 | A1 | 10/2017 | Frost et al. | |
| 2018/0346600 | A1* | 12/2018 | Kim | C07K 16/468 |

FOREIGN PATENT DOCUMENTS

| | | | |
|---|---|---|---|
| JP | 2016533164 A | 10/2016 | |
| KR | 20140106933 | * 10/2014 | ............... C12Q 1/25 |
| WO | WO 98/41869 A1 | 9/1998 | |
| WO | WO 2014/035693 A2 | 3/2014 | |
| WO | WO 2016/174229 A1 | 11/2016 | |
| WO | WO 2017/132627 A2 | 8/2017 | |
| WO | WO 2018/170013 A1 | 9/2018 | |
| WO | WO 2018/204150 A1 | 11/2018 | |

OTHER PUBLICATIONS

Rosowski (Microb Cell Fact 2018 (Jan. 17:3, Total 11 pages). (Year: 2018).*
Krah et al. Protein Engineering, Design & Selection, 2017, vol. 30 No. 4, pp. 291-301 (Year: 2017).*
Tiller Annu. Rev. Biomed. Eng. 2015 vol. 17:191-216 (Year: 2015).*
Tomlinson Methods in Enzymology 2000 vol. 326 p. 461-479 (Year: 2000).*
English Translation KR20140106933 (Year: 2014).*
International Search Report and Written Opinion in Application No. PCT/US2019/055047 dated Feb. 28, 2020 in 13 pages.
Segaliny, et al. 2018 "Functional TCT T cell screening using single-cell droplet microfluidics" Lab chip 18(24): 3733-3749.
Extended European Search Report in corresponding European Application No. 19871473.5, dated Apr. 3, 2023.

* cited by examiner

SEQUENCE LISTING

```
<160> NUMBER OF SEQ ID NOS: 42

<210> SEQ ID NO 1
<211> LENGTH: 4
<212> TYPE: PRT
<213> ORGANISM: Artificial Sequence
<220> FEATURE:
<223> OTHER INFORMATION: peptide

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: peptide

<400> SEQUENCE: 2

Gly Gly Ser Gly
1
```

```
<210> SEQ ID NO 3
<211> LENGTH: 5
<212> TYPE: PRT
<213> ORGANISM: Artificial Sequence
<220> FEATURE:
<223> OTHER INFORMATION: pepide

<400> SEQUENCE: 3

Gly Gly Gly Gly Ser
1               5

<210> SEQ ID NO 4
<211> LENGTH: 5
<212> TYPE: PRT
<213> ORGANISM: Artificial Sequence
<220> FEATURE:
<223> OTHER INFORMATION: peptide

<400> SEQUENCE: 4

Gly Gly Ser Gly Gly
1               5

<210> SEQ ID NO 5
<211> LENGTH: 5
<212> TYPE: PRT
<213> ORGANISM: Artificial Sequence
<220> FEATURE:
<223> OTHER INFORMATION: peptide

<400> SEQUENCE: 5

Gly Lys Pro Gly Ser
1               5

<210> SEQ ID NO 6
<211> LENGTH: 6
<212> TYPE: PRT
<213> ORGANISM: Artificial Sequence
<220> FEATURE:
<223> OTHER INFORMATION: peptide

<400> SEQUENCE: 6

Gly Lys Pro Gly Gly Ser
1               5

<210> SEQ ID NO 7
<211> LENGTH: 7
<212> TYPE: PRT
<213> ORGANISM: Artificial Sequence
<220> FEATURE:
<223> OTHER INFORMATION: peptide

<400> SEQUENCE: 7

Gly Lys Pro Gly Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: peptide

<400> SEQUENCE: 8

Ala Glu Ala Ala Ala Lys Ala
1               5

<210> SEQ ID NO 9
```

```
<211> LENGTH: 9
<212> TYPE: PRT
<213> ORGANISM: Artificial Sequence
<220> FEATURE:
<223> OTHER INFORMATION: peptide

<400> SEQUENCE: 9

Thr Ala Ala Ala Ala Thr Ala Ala Ala
1               5

<210> SEQ ID NO 10
<211> LENGTH: 6
<212> TYPE: PRT
<213> ORGANISM: Artificial Sequence
<220> FEATURE:
<223> OTHER INFORMATION: peptide

<400> SEQUENCE: 10

Phe Asn Arg Gly Glu Cys
1               5

<210> SEQ ID NO 11
<211> LENGTH: 5
<212> TYPE: PRT
<213> ORGANISM: Artificial Sequence
<220> FEATURE:
<223> OTHER INFORMATION: peptide

<400> SEQUENCE: 11

Glu Pro Ser Gly Pro
1               5

<210> SEQ ID NO 12
<211> LENGTH: 4
<212> TYPE: PRT
<213> ORGANISM: Artificial Sequence
<220> FEATURE:
<223> OTHER INFORMATION: peptide

<400> SEQUENCE: 12

Leu Gly Gly Cys
1

<210> SEQ ID NO 13
<211> LENGTH: 6
<212> TYPE: PRT
<213> ORGANISM: Artificial Sequence
<220> FEATURE:
<223> OTHER INFORMATION: peptide

<400> SEQUENCE: 13

Val Glu Pro Lys Glu Cys
1               5

<210> SEQ ID NO 14
<211> LENGTH: 20
<212> TYPE: PRT
<213> ORGANISM: Artificial Sequence
<220> FEATURE:
<223> OTHER INFORMATION: peptide

<400> SEQUENCE: 14

Pro Ser Gly Gln Ala Gly Ala Ala Ala Ser Glu Ser Leu Phe Val Ser
1               5                   10                  15

Asn His Ala Tyr
            20
```

<210> SEQ ID NO 15
<211> LENGTH: 16
<212> TYPE: PRT
<213> ORGANISM: Artificial Sequence
<220> FEATURE:
<223> OTHER INFORMATION: peptide

<400> SEQUENCE: 15

Ala Lys Thr Thr Pro Lys Leu Glu Glu Gly Glu Phe Ser Glu Ala Arg
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: peptide

<400> SEQUENCE: 16

Ala Lys Thr Thr Pro Lys Leu Glu Glu Gly Glu Phe Ser Glu Ala Arg
1               5                   10                  15

Val

<210> SEQ ID NO 17
<211> LENGTH: 9
<212> TYPE: PRT
<213> ORGANISM: Artificial Sequence
<220> FEATURE:
<223> OTHER INFORMATION: peptide

<400> SEQUENCE: 17

Ala Lys Thr Thr Pro Lys Leu Gly Gly
1               5

<210> SEQ ID NO 18
<211> LENGTH: 10
<212> TYPE: PRT
<213> ORGANISM: Artificial Sequence
<220> FEATURE:
<223> OTHER INFORMATION: peptide

<400> SEQUENCE: 18

Ser Ala Lys Thr Thr Pro Lys Leu Gly Gly
1               5                   10

<210> SEQ ID NO 19
<211> LENGTH: 17
<212> TYPE: PRT
<213> ORGANISM: Artificial Sequence
<220> FEATURE:
<223> OTHER INFORMATION: peptide

<400> SEQUENCE: 19

Ala Lys Thr Thr Pro Lys Leu Glu Glu Gly Glu Phe Ser Glu Ala Arg
1               5                   10                  15

Val

<210> SEQ ID NO 20
<211> LENGTH: 6
<212> TYPE: PRT
<213> ORGANISM: Artificial Sequence
<220> FEATURE:
<223> OTHER INFORMATION: peptide

<400> SEQUENCE: 20

Ser Ala Lys Thr Thr Pro
1               5

<210> SEQ ID NO 21
<211> LENGTH: 10
<212> TYPE: PRT
<213> ORGANISM: Artificial Sequence
<220> FEATURE:
<223> OTHER INFORMATION: peptide

<400> SEQUENCE: 21

Ser Ala Lys Thr Thr Pro Lys Leu Gly Gly
1               5                   10

<210> SEQ ID NO 22
<211> LENGTH: 6
<212> TYPE: PRT
<213> ORGANISM: Artificial Sequence
<220> FEATURE:
<223> OTHER INFORMATION: peptide

<400> SEQUENCE: 22

Arg Ala Asp Ala Ala Pro
1               5

<210> SEQ ID NO 23
<211> LENGTH: 9
<212> TYPE: PRT
<213> ORGANISM: Artificial Sequence
<220> FEATURE:
<223> OTHER INFORMATION: peptide

<400> SEQUENCE: 23

Arg Ala Asp Ala Ala Pro Thr Val Ser
1               5

<210> SEQ ID NO 24
<211> LENGTH: 12
<212> TYPE: PRT
<213> ORGANISM: Artificial Sequence
<220> FEATURE:
<223> OTHER INFORMATION: peptide

<400> SEQUENCE: 24

Arg Ala Asp Ala Ala Ala Ala Gly Gly Pro Gly Ser
1               5                   10

<210> SEQ ID NO 25
<211> LENGTH: 12
<212> TYPE: PRT
<213> ORGANISM: Artificial Sequence
<220> FEATURE:
<223> OTHER INFORMATION: peptide

<400> SEQUENCE: 25

Arg Ala Asp Ala Ala Ala Ala Gly Gly Gly Gly Ser
1               5                   10

<210> SEQ ID NO 26
<211> LENGTH: 18
<212> TYPE: PRT
<213> ORGANISM: Artificial Sequence
<220> FEATURE:
<223> OTHER INFORMATION: peptide

<400> SEQUENCE: 26

Ser Ala Lys Thr Thr Pro Lys Leu Glu Glu Gly Glu Phe Ser Glu Ala

```
                1               5                   10                  15
Arg Val

<210> SEQ ID NO 27
<211> LENGTH: 5
<212> TYPE: PRT
<213> ORGANISM: Artificial Sequence
<220> FEATURE:
<223> OTHER INFORMATION: peptide

<400> SEQUENCE: 27

Ala Asp Ala Ala Pro
1               5

<210> SEQ ID NO 28
<211> LENGTH: 12
<212> TYPE: PRT
<213> ORGANISM: Artificial Sequence
<220> FEATURE:
<223> OTHER INFORMATION: peptide

<400> SEQUENCE: 28

Ala Asp Ala Ala Pro Thr Val Ser Ile Phe Pro Pro
1               5                   10

<210> SEQ ID NO 29
<211> LENGTH: 5
<212> TYPE: PRT
<213> ORGANISM: Artificial Sequence
<220> FEATURE:
<223> OTHER INFORMATION: peptide

<400> SEQUENCE: 29

Thr Val Ala Ala Pro
1               5

<210> SEQ ID NO 30
<211> LENGTH: 12
<212> TYPE: PRT
<213> ORGANISM: Artificial Sequence
<220> FEATURE:
<223> OTHER INFORMATION: peptide

<400> SEQUENCE: 30

Thr Val Ala Ala Pro Ser Val Phe Ile Phe Pro Pro
1               5                   10

<210> SEQ ID NO 31
<211> LENGTH: 6
<212> TYPE: PRT
<213> ORGANISM: Artificial Sequence
<220> FEATURE:
<223> OTHER INFORMATION: peptide

<400> SEQUENCE: 31

Gln Pro Lys Ala Ala Pro
1               5

<210> SEQ ID NO 32
<211> LENGTH: 13
<212> TYPE: PRT
<213> ORGANISM: Artificial Sequence
<220> FEATURE:
<223> OTHER INFORMATION: peptide

<400> SEQUENCE: 32
```

```
Gln Pro Lys Ala Ala Pro Ser Val Thr Leu Phe Pro Pro
1               5                   10
```

<210> SEQ ID NO 33
<211> LENGTH: 6
<212> TYPE: PRT
<213> ORGANISM: Artificial Sequence
<220> FEATURE:
<223> OTHER INFORMATION: peptide

<400> SEQUENCE: 33

```
Ala Lys Thr Thr Pro Pro
1               5
```

<210> SEQ ID NO 34
<211> LENGTH: 13
<212> TYPE: PRT
<213> ORGANISM: Artificial Sequence
<220> FEATURE:
<223> OTHER INFORMATION: peptide

<400> SEQUENCE: 34

```
Ala Lys Thr Thr Pro Pro Ser Val Thr Pro Leu Ala Pro
1               5                   10
```

<210> SEQ ID NO 35
<211> LENGTH: 6
<212> TYPE: PRT
<213> ORGANISM: Artificial Sequence
<220> FEATURE:
<223> OTHER INFORMATION: peptide

<400> SEQUENCE: 35

```
Ala Lys Thr Thr Ala Pro
1               5
```

<210> SEQ ID NO 36
<211> LENGTH: 13
<212> TYPE: PRT
<213> ORGANISM: Artificial Sequence
<220> FEATURE:
<223> OTHER INFORMATION: peptide

<400> SEQUENCE: 36

```
Ala Lys Thr Thr Ala Pro Ser Val Tyr Pro Leu Ala Pro
1               5                   10
```

<210> SEQ ID NO 37
<211> LENGTH: 15
<212> TYPE: PRT
<213> ORGANISM: Artificial Sequence
<220> FEATURE:
<223> OTHER INFORMATION: peptide

<400> SEQUENCE: 37

```
Gly Pro Ala Lys Glu Leu Thr Pro Leu Lys Glu Ala Lys Val Ser
1               5                   10                  15
```

<210> SEQ ID NO 38
<211> LENGTH: 6
<212> TYPE: PRT
<213> ORGANISM: Artificial Sequence
<220> FEATURE:
<223> OTHER INFORMATION: peptide

<400> SEQUENCE: 38

```
Ala Ser Thr Lys Gly Pro
```

```
                                   -continued
1               5

<210> SEQ ID NO 39
<211> LENGTH: 13
<212> TYPE: PRT
<213> ORGANISM: Artificial Sequence
<220> FEATURE:
<223> OTHER INFORMATION: peptide

<400> SEQUENCE: 39

Ala Ser Thr Lys Gly Pro Ser Val Phe Pro Leu Ala Pro
1               5                   10

<210> SEQ ID NO 40
<211> LENGTH: 15
<212> TYPE: PRT
<213> ORGANISM: Artificial Sequence
<220> FEATURE:
<223> OTHER INFORMATION: peptide

<400> SEQUENCE: 40

Gly Glu Asn Lys Val Glu Tyr Ala Pro Ala Leu Met Ala Leu Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: peptide

<400> SEQUENCE: 41

Gly His Glu Ala Ala Ala Val Met Gln Val Gln Tyr Pro Ala Ser
1               5                   10                  15

<210> SEQ ID NO 42
<211> LENGTH: 18
<212> TYPE: PRT
<213> ORGANISM: Artificial Sequence
<220> FEATURE:
<223> OTHER INFORMATION: peptide

<400> SEQUENCE: 42

Val Glu Gly Gly Ser Gly Gly Ser Gly Gly Ser Gly Gly Ser Gly Gly
1               5                   10                  15

Val Asp
```

COMPARTMENTALIZED ASSAYS OF BISPECIFIC AND MULTISPECIFIC BIOLOGICS

CROSS REFERENCE TO RELATED APPLICATIONS

This application is a continuation of International Application No.: PCT/US2019/055047, filed Oct. 7, 2019, designating the U.S. and published in English on Apr. 16, 2020 as WO 2020/076730, which claims the benefit of priority to U.S. Provisional Patent Application Ser. No. 67/784,171, filed on 21 Dec. 2018, and to U.S. Provisional Patent Application Ser. No. 62/742,837, filed on 8 Oct. 2018, the contents of which are incorporated by reference in their entirety.

STATEMENT REGARDING FEDERALLY SPONSORED RESEARCH OR DEVELOPMENT

This invention was made with government support under the SBIR Grant Number 1913404 awarded by the National Science Foundation. The government has certain rights in the invention.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 35135364_1.TXT, the date of creation of the ASCII text file is Jun. 11, 2021, and the size of the ASCII text file is 8.13 KB.

TECHNICAL FIELD

The present disclosure is related to various embodiments of compartmentalized nano-volume based biological assays, more specifically, to microfluidic droplet or microchamber based assays of bispecific and multispecific biologics for general applications, particularly therapeutic usages.

BACKGROUND

Bispecific and multispecific biologics are single biological molecules capable of engaging at least two molecular sites on the same or distinct targets including ligands and receptors. Examples include bispecific antibodies (BsAbs), immunocytokine (i.e., fusion of an antibody moiety with a cytokine moiety), and chimeric cytokines, as novel and increasingly important approaches for dual or multivalent targeting strategies. Some BsAbs may be useful for disease therapy.

Conventionally, a bispecific or multispecific biologic can be screened using multi-step approaches via rational or random pairing or assembling of two or more functional moieties (or, subunits), wherein individual moieties of a biologic are co-expressed and assembled in cells or in vitro, and the resultant individual assemblies, each representing a variant of the biologic, are tested respectively in vitro for target-binding or functional activities. Alternatively, individual assemblies are displayed on a cell surface and subject to a binding assay, wherein positive binders are selected, cloned, further expressed and screened with a functional validation assay.

With the advancement of clinical development, there are increasing needs of innovative yet robust platform technologies to enable highly efficient screening of functionally active bispecific antibodies, and more broadly, bispecific and multispecific biologics.

SUMMARY

The following summary is illustrative only and is not intended to be limiting in any way. That is, the following summary is provided to introduce concepts, highlights, benefits and advantages of the novel and non-obvious embodiments of systems, methods, techniques and devices described herein. Select implementations are further described below in the detailed description. Thus, the following summary is not intended to identify essential features of the claimed subject matter, nor is it intended for use in determining the scope of the claimed subject matter.

Some embodiments utilize microfluidics technology in combination with cell engineering and biological assays. According to several embodiments, methods provided herein avoid the issues of biased selection of individual moieties of a bispecific or multispecific biologic in conventional assay approaches. The use of nano-volume droplets or microchambers also permits much deeper and efficient screenings for functional biologics at the single cell level from a large pool of candidates without the need for large sample volumes.

Provided herein, in several embodiments, are methods for screening a bispecific or multispecific biologic in compartmentalized nano-volumes. In some embodiments, each compartmentalized nano-volume is provided substantially with at least two distinct types of cells, wherein a first type of cell is engineered to express a single variant per cell for the said biologic, wherein a second cell is selected to produce a reporter signal upon the triggering by a functional bispecific or multispecific biologic, wherein at least one of the said first and second cells concomitantly express one or more distinct cell surface targets of the said biologic. Proper expression, assembling and secretion of a functional biologic and its interaction with intended molecular targets produces a positive reporter signal inside the nano-volume, thereby allowing the detection and recovery of the biologic-expressing cell and subsequent genetic identification of respective functional variants of the said biologic.

As disclosed herein, several embodiments relate to a method for performing assays in compartmentalized nano-volumes to screen for functional bispecific or multispecific biologics. In several embodiments, the method comprises providing a plurality of at least two distinct types of cells, wherein two or more first-type cells are engineered to express substantially a single genetic-variant per cell for a bispecific or multispecific biologic in a secreted form, wherein two or more second-type cells are selected or engineered to produce a positive reporter signal molecule that is triggered by a functional variant of the said biologic expressed by a first-type cell, providing a plurality of compartmentalized nano-volumes, wherein two or more nano-volumes are each provided with substantially one first-type cell, and one or more second-type cell(s), incubating the said nano-volumes over a period of time to allow the expression and secretion of the said biologics inside the said nano-volumes, collecting data representing the positive reporter signal molecule triggered by secreted biologics inside the said nano-volumes. In several embodiments, the method further comprises recovering cells from the nano-volumes with the positive reporter signal molecule and extracting the genetic information representing respective functional variants of the biologics.

In several embodiments, the compartmentalized nano-volumes are microchambers or droplets with a homogeneous or near-homogeneous size of about 0.03 nL to about 100 nL. In several embodiments, the size (e.g. volume) ranges from about about 0.1 nL to about 4 nL. In additional embodiments, the volume can range from about 0.03 to about 100 nL, including any volumes between (and including) those listed.

In some examples, the bispecific or multispecific biologic includes at least two distinct target-binding moieties. Depending on the embodiment, the target-binding moieties can be an IgG heavy chain, an IgG light chain, a scFv, a Fab, a Fab', a F(ab')2, a single domain antibody, a VHH antibody, a nanobody, a non-antibody alternative scaffold, an extracellular fragment of cell surface protein, a chemokine or a chemokine-like molecule, a cytokine or a cytokine-like molecule, and a combination or derivative of the foregoing molecules.

In several embodiments, target-binding moieties of the said biologic are linked to one another. For example, in several embodiments, they are linked by at least one non-target-binding moiety, which is selected from a group consisting of a heterodimerization domain, a hetero-trimerization domain, a linker peptide with a length of about 2 to about 30 amino acids or of about 10 to about 50 amino acids. In embodiments in which multispecific binding moieties are used, the linkers may be the same type (e.g., domain and/or length) or may vary in type and/or length.

In several embodiments, the bispecific biologic is an antibody including a common IgG light chain plus two distinct IgG heavy chains. In several embodiments, the bispecific biologic is an antibody including a common IgG heavy chain plus two distinct IgG light chains.

In several embodiments, the bispecific biologic is an antibody including two distinct moieties. For example, in several embodiments the moieties are selected (individually) from scFvs, Fabs, VHH, and single domain antibodies. In several embodiments, the moieties are fused as a single chimeric polypeptide through a linker peptide of about 2 to about 30 amino acids.

In several embodiments, the bispecific biologic is an immunocytokine including an antibody or an antibody derivative or an antibody-like molecule, which is fused to a cytokine or a cytokine-like polypeptide thereof.

In several embodiments, the bispecific biologic is a chimeric fusion protein including at least two distinct cytokines or cytokine-like polypeptides thereof.

In several embodiments, the first-type cell is engineered with one or more distinct expression cassettes or vehicles that are integrated into the genome of the first-type cell. As such the cells of the first type express a single genetic-variant of the said biologic from the integrated expression cassettes or vehicles.

In several embodiments, the bispecific or multispecific biologic target two or more distinct sites on a cell-surface target, or on two or more distinct cell-surface targets expressed by at least one of the cells provided in the compartmentalized nano-volume.

In several embodiments, the positive reporter signal molecule in the second-type cell is a fluorescent protein, a fluorogenic molecule, or a fluorescent molecule or complex. In several embodiments, the positive reporter signal molecule in the second cell is a luciferase, a luminogenic molecule or complex. In several embodiments, the positive reporter signal molecule is genetically encoded by an expression cassette (or cassettes) integrated into the genome of a second-type cell.

In several embodiments, the positive reporter signal molecule is an effector molecule downstream of a cell-surface target in a second-type cell, wherein the target-binding by a functional biologic expressed by the first-type cell triggers the accumulation of the said effector molecules, thereby producing a detectable signal that represents that the biologic expressed by the first cell has successfully interacted with a target on the second cell.

In several embodiments, the positive reporter signal molecule is a matched pair of FRET donor and acceptor conjugated with two distinct targets of the said biologic respectively.

In several embodiments, the positive reporter signal molecule is genetically detected by a linkage Polymerase Chain Reaction (PCR) that links a reporter-encoding sequence to a sequence representing the said biologic, followed by genetic sequencing of the linkage PCR products.

In several embodiments, three distinct types of cells are provided, wherein a first-type cell is engineered to express a single variant of the said biologic, a second-type cell is selected or engineered to serve as a reporter cell, and a third-type cell is selected as a target-expressing cell.

In several embodiments, collecting data that represent the positive reporter signal molecule activation is through detecting a reporter-derived optical signal using an optical detection device. In several embodiments, collecting data that represent the positive reporter signal molecule activation is through sequencing a linked nucleic acid sequence that in one portion represents a reporter gene transcript, and in another portion represents the said biologic.

In several embodiments, the at least two distinct types of cells are mammalian cells, or a derivative or an engineered form of a mammalian cell. In several embodiments, the at least two distinct types of cells includes a mammalian cell and the other is a yeast or fungal cell. In several embodiments, the two or more first-type cells are diploid yeast cells and wherein the two or more second-type cells are mammalian cells. In several embodiments, the diploid yeast cell is derived from the mating between two haploid strains of opposite mating types, wherein a first haploid strain is engineered to express substantially a single genetic-variant each encoding at least one moiety of the said biologic, and a second haploid strain is engineered to express substantially a single genetic-variant encoding the remaining moiety or moieties of the said biologic.

Some aspects relate to a method for performing assays in compartmentalized nano-volumes to screen for functional bispecific or multispecific biologics, comprising providing a plurality of compartmentalized nano-volumes, wherein two or more nano-volumes are each provided with substantially a single diploid yeast cell and at least one mammalian cell, wherein the said yeast cell is engineered to express a single genetic-variant of a bispecific or multispecific biologic in a secreted form, wherein the said mammalian cell is selected to produce a reporter signal that is triggered by a functional variant of the said biologic expressed by the yeast cell, incubating the compartmentalized nano-volumes over a period of time to allow the expression and secretion of the biologic inside the said nano-volumes, collecting data representing a positive reporter signal triggered by secreted functional biologics inside the nano-volumes, and recovering cells from the nano-volumes with a positive reporter signal. In several embodiments, the method further comprises extracting the genetic information representing respective functional variants of the biologics.

In several embodiments, the diploid yeast cell is derived from the mating between two haploid strains of opposite mating types, wherein a first haploid strain is engineered to express substantially a single genetic-variant each encoding at least one moiety of the said biologic, and a second haploid strain is engineered to express substantially a single genetic-variant encoding the remaining moiety or moieties of the said biologic.

In some examples, the compartmentalized nano-volumes are microfluidic microchambers or droplets with a homogeneous or near-homogeneous size of about 0.03 nL to about 100 nL, or of about 0.1 nL to about 4 nL.

In some examples, the bispecific or multispecific biologic includes at least two functionally distinct target-binding moieties selected from a group consisting of an IgG heavy chain, an IgG light chain, a scFv, a Fab, a Fab', a F(ab')2, a single domain antibody, a VHH domain antibody, a nanobody, a non-antibody alternative scaffold, a cytokine or a cytokine-like polypeptide, an extracellular fragment of a cell surface protein, a chemokine or a chemokine-like molecule, and a combination or derivative of the foregoing said molecules thereof.

In some examples, the target-binding moieties of the said biologic are linked by at least one non-target-binding moiety of the said biologic selected from a group consisting of a heterodimerization domain a hetero-trimerization domain, a linker peptide with a length of about 2 to about 30 amino acids or of about 10 to about 50 amino acids, or a combination of the foregoing domains and linkers.

In some examples, the bispecific biologic is an antibody including a common IgG light chain plus two distinct IgG heavy chains, or an antibody including a common IgG heavy chain plus two distinct IgG light chains.

In some examples, the bispecific biologic is an immunocytokine including an antibody or an antibody derivative or an antibody-like molecule, and a cytokine or a cytokine-like molecule.

In some examples, the bispecific biologic is a single chimeric fusion protein or a complex including at least two distinct cytokines or cytokine-like molecules.

Some aspects relate to a system for screening for functional variants of a multispecific biologic, including:

a plurality of droplets or microchambers, each droplet or microchamber including:

a first cell including a nucleic acid sequence encoding a genetic variant of a first component of a multispecific biologic, and including a nucleic acid sequence encoding a genetic variant of a second component of the multispecific biologic;

a second cell including a nucleic acid sequence encoding a reporter molecule;

wherein the first or second cell includes a first target for the first component, and wherein the second cell includes a second target for the second component;

and wherein the reporter molecule is transcribed when the first component binds to the first target, and the second component binds to the second target, indicating that the genetic variants of the first and second components of the multispecific biologic encode a functional version of the multispecific biologic.

In some examples, the multispecific biologic includes a bispecific or trispecific biologic In some examples, the biologic includes an antibody, a cytokine or an immunocytokine.

Some aspects relate to a compartmentalized system for directly screening for proper pairing of components that include functional variants of a bispecific antibody, cytokine or immunocytokine, the system including a plurality of droplets or microchambers, each droplet or microchamber including a first mammalian cell including a nucleic acid encoding a genetic variant of a first component of a bispecific antibody, cytokine or immunocytokine, and a nucleic acid encoding a genetic variant of a second component of the bispecific antibody, cytokine or immunocytokine, and a second mammalian cell including a first target, a second target, and a nucleic acid encoding a reporter molecule, wherein the reporter molecule is transcribed upon activation of the first and second targets by a functional bispecific antibody, cytokine or immunocytokine, wherein the first and second components of the bispecific antibody, cytokine or immunocytokine are functional and bind to the first and second targets if the genetic variants of the first and second components of the bispecific antibody, cytokine or immunocytokine are functional variants and bind together to form the bispecific antibody, cytokine or immunocytokine.

Some aspects relate to a method for screening for functional variants of a multispecific biologic, including providing a first DNA library including a library of genetic variants of a first component of a multispecific biologic, providing a second DNA library including a library of genetic variants of a second component of the multispecific biologic, introducing the first and second DNA libraries into a plurality of cells to obtain a cell library, wherein cells of the cell library express variants of the first and second components, introducing cells of the cell library into droplets (or microchambers), wherein at least two droplets each include substantially a single cell of the cell library, introducing reporter cells into the droplets, wherein at least two droplets each include one or more reporter cells, incubating the droplets, detecting signals generated by the reporter cells; and identifying, based on the detected signals, which droplets include functional variants of the multispecific biologic.

Some aspects relate to a method for directly screening for proper pairing of components that include functional variants of a bispecific antibody, cytokine or immunocytokine, the method comprising providing a first DNA library including a library of genetic variants of a first component of a bispecific antibody, cytokine or immunocytokine, providing a second (or further) DNA library including a library of genetic variants of a second component of the bispecific antibody, cytokine or immunocytokine, introducing the first and second (and/or further) DNA libraries into a plurality of cells to obtain a cell library, wherein each cell of the cell library expresses substantially a distinct variant of the first component and a distinct variant of the second component in relation to each of the other cells of the cell library, introducing the cells of the cell library into droplets, wherein at least two droplets each include substantially a single cell of the cell library, introducing a plurality of reporter cells into the droplets, whereby each droplet further includes a reporter cell including a first target, a second target, and a nucleic acid encoding a reporter molecule, wherein the reporter molecule is transcribed upon activation of the first and second targets by a functional bispecific antibody, cytokine or immunocytokine, thereby generating a reporter signal, incubating the droplets to allow transcription and assembly of the first and second components of the bispecific antibody, cytokine or immunocytokine in each droplet, wherein in each droplet the first and second components of the bispecific antibody, cytokine or immunocytokine are functional and bind to the first and second targets if the genetic variants of the first and second components of the bispecific antibody, cytokine or immunocytokine are functional variants and bind together to form the bispecific antibody, cytokine or immunocytokine, and detecting the reporter signals. In several embodiments, the method further comprises identifying, based on the detected reporter signals, which droplets include functional variants of the bispecific antibody, cytokine or immunocytokine.

In some examples, each cell of the cell library includes an individual variant of the first component, and an individual variant of the second component.

In some examples, the multispecific biologic includes a bispecific or trispecific biologic.

In some examples, the biologic includes an antibody, a cytokine or an immunocytokine.

In some examples, identifying which droplets include functional variants of the multispecific biologic includes sequencing nucleic acids of cells in the droplets.

Some aspects relate to a method for performing assays in compartmentalized nano-volumes to screen for functional bispecific or multispecific biologics, including providing a plurality of at least two distinct types of cells, wherein two or more first-type cells are (1) engineered to express substantially a single genetic-variant per cell for a bispecific or multispecific biologic in a secreted form, are (2) engineered or selected to express at least one target intended for the biologic, and are (3) engineered or selected to produce a positive reporter signal molecule that is triggered by a functional variant of the said biologic that engages the first-type cell to a distinct second-type cell that expresses at least another distinct target intended for the said biologic, providing a plurality of compartmentalized nano-volumes, wherein two or more nano-volumes are each provided with substantially one first-type cell, and one or more second-type cell(s), incubating the said nano-volumes over a period of time to allow the expression and secretion of the said biologics inside the said nano-volumes, collecting data representing the positive reporter signal molecule triggered by secreted biologics inside the said nano-volumes, and recovering cells from the nano-volumes with the positive reporter signal molecule and extracting the genetic information representing respective functional variants of the biologics.

BRIEF DESCRIPTION OF THE DRAWINGS

The accompanying drawings are included to provide a further understanding of the present disclosure and are incorporated in and constitute a part of this specification. The drawings illustrate embodiments of the present disclosure and, together with the description, serve to explain the principles of the present disclosure. The drawings may not necessarily be in scale so as to better present certain features of the illustrated subject matter. Like annotation symbols in the various drawings indicate like elements, unless otherwise stated.

DETAILED DESCRIPTION

Figure 1:
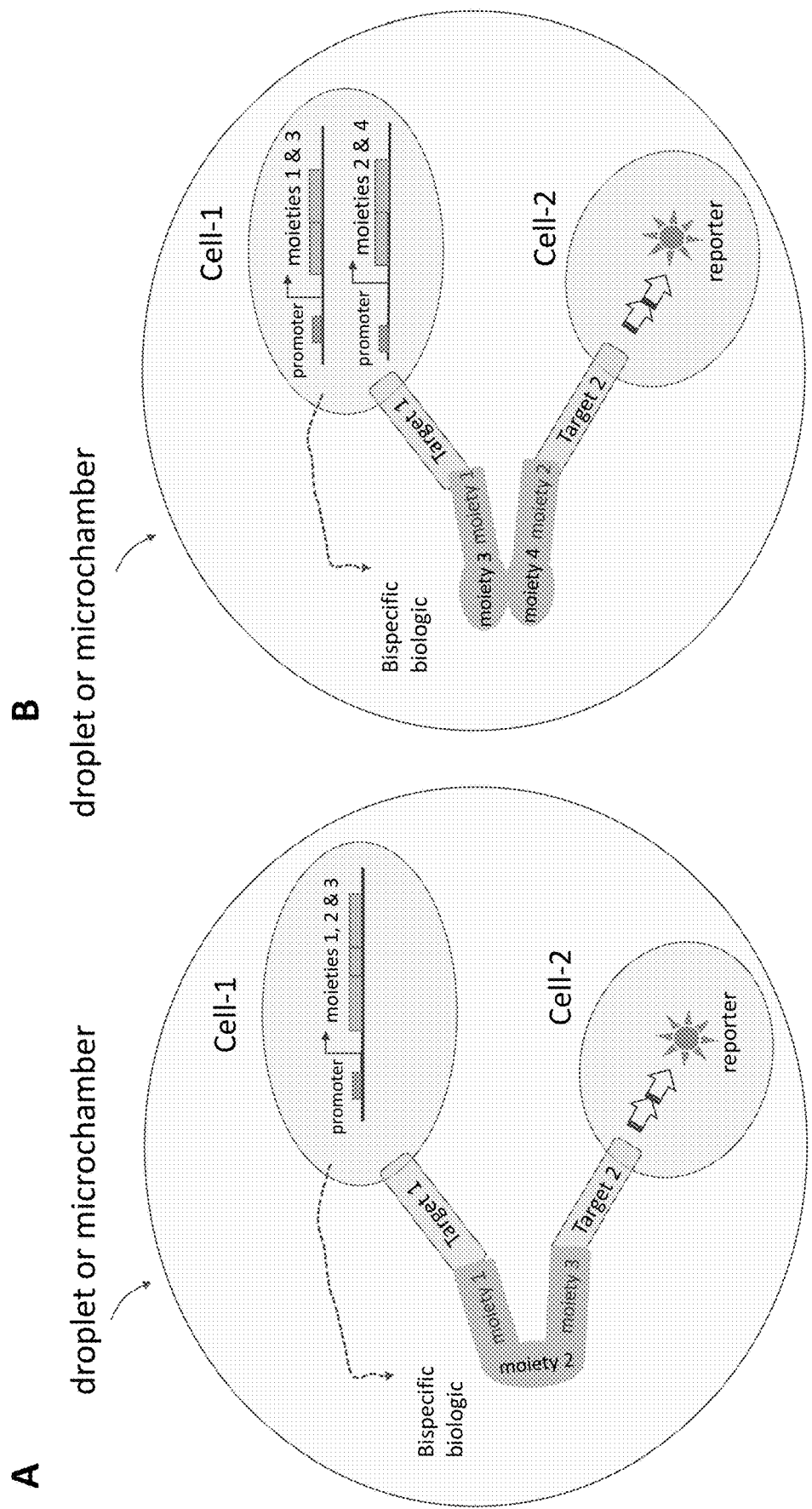
FIG. 1 illustrates a general principle and features of some embodiments of a compartmentalized nano-volume based assay for a dual-target binding bispecific biologic comprising a single chimeric protein with two target-binding moieties and one non-target-binding moiety (A), or two sub-units, each with a target-binding and a non-target-binding moiety (B).

Detailed embodiments of the claimed subject matters are disclosed herein. However, it shall be understood that the disclosed embodiments are merely illustrative of the claimed subject matters which may be embodied in various forms. The present disclosure may, however, be embodied in many different forms and should not be construed as limited to the exemplary embodiments set forth herein. Rather, these exemplary embodiments are provided so that description of the present disclosure is thorough and complete and will fully convey the scope of the present disclosure to those skilled in the art. In the description below, details of well-known features and techniques may be omitted to avoid unnecessarily obscuring the presented embodiments.

Overview

Some embodiments of the systems and methods described herein relate to biological assays in compartmentalized nano-volumes, including general assay principles, schemes, components and processes for direct and rapid screening of functional single variants from an engineered library of bispecific or multispecific biologics in a plurality of compartmentalized nano-volumes in a microfluidic device. As used herein, nano-volumes shall refer to nanoliter- and sub-nanoliter microfluidic droplets or microchambers with a homogeneous or near-homogeneous volume ranging from about 0.03 nL to about 100 nL (aka, nanoliter). In several embodiments, the volume ranges from about 0.05 to about 10 nL. In some examples, the nano-volume is about 0.1 nL, 0.2 nL, 0.3 nL, 0.4 nL, 0.5 nL, 0.6 nL, 0.7 nL, 0.8 nL, 0.9 nL, 1 nL, 2 nL, 3 nL, 4 nL, 5 nL, 6 nL, 7 nL, 8 nL, 9 nL, 10 nL, 11 nL, 12 nL, 13 nL, 14 nL, 15 nL, 16 nL, 17 nL, 18 nL, 19 nL, 20 nL, 21 nL, 22 nL, 23 nL, 24 nL, 25 nL, 26 nL, 27 nL, 28 nL, 29 nL, 30 nL, 31 nL, 32 nL, 33 nL, 34 nL, 35 nL, 36 nL, 37 nL, 38 nL, 39 nL, 40 nL, 41 nL, 42 nL, 43 nL, 44 nL, 45 nL, 46 nL, 47 nL, 48 nL, 49 nL, 50 nL, 51 nL, 52 nL, 53 nL, 54 nL, 55 nL, 56 nL, 57 nL, 58 nL, 59 nL, 60 nL, 61 nL, 62 nL, 63 nL, 64 nL, 65 nL, 66 nL, 67 nL, 68 nL, 69 nL, 70 nL, 71 nL, 72 nL, 73 nL, 74 nL, 75 nL, 76 nL, 77 nL, 78 nL, 79 nL, 80 nL, 81 nL, 82 nL, 83 nL, 84 nL, 85 nL, 86 nL, 87 nL, 88 nL, 89 nL, 90 nL, 91 nL, 92 nL, 93 nL, 94 nL, 95 nL, 96 nL, 97 nL, 98 nL, 99 nL or 100 nL. In some embodiments, the volume ranges from about 0.1 nL to about 4 nL, from about 0.1 nL to about 1 nL or from about 5 nL to about 10 nL.

In some embodiments, the compartmentalized nano-volumes comprise droplets. In other embodiments, the compartmentalized nano-volumes are contained within enclosed or semi-enclosed devices.

As used herein, droplets shall be given its ordinary meaning and shall refer to water-in-oil emulsions, e.g., discrete aqueous microcompartments of a certain volume that encapsulate an aqueous liquid surrounded by an immiscible oil phase. As used herein, microchambers shall be given its ordinary meaning and generally refer to microfluidic chambers or micro-pores of a certain volume that are used to contain a single-phase aqueous liquid. As would be understood by a person skilled in the art, microchambers may have a geometry, a feature or a shape representing one or more polyhedrons selected from a group consisting of a cube, a cuboid, a cylinder, a trapezoid, a sphere, and an ellipsoid.

As used herein, bispecific biologic shall be given its ordinary meaning and shall refer to an integral single molecule or complex comprising at least two target-binding moieties selected from a group consisting of proteins or protein fragments thereof, peptides, sugars, or nucleic acids or any complex combinations of these substances thereof, wherein the said biologic is intended to bind to two molecular sites on a same target molecule, or on two distinct target molecules.

As used herein, multispecific biologic shall be given its ordinary meaning and shall refer to an integral single molecule or complex comprising at least three target-binding moieties selected from a group consisting of proteins or protein fragments thereof, peptides, sugars, or nucleic acids or any complex combinations of these substances thereof, wherein the said biologic is intended to bind to three or more molecular sites on the same target molecule, or on two or three distinct target molecules.

In some embodiments, preferred target-binding moieties comprised by a bispecific or multispecific biologic are proteins, protein fragments, peptides, or a combination of these substances thereof. In some embodiments, more preferred target-binding moieties are: (1) antibodies and antibody-like molecules, and further derivatives or engineered forms of these said molecules thereof; (2) cytokine or cytokine-like molecules, including cytokines, growth factors, chemokines, extracellular domains of cell membrane or surface proteins such as receptors, and further derivatives or engineered forms of these said molecules thereof; (3) non-antibody alternative scaffolds; (4) the combinations or pairs from (1), (2) and (3) above with exemplary examples of antibody-cytokine fusions or immunocytokines and their various forms of derivatives and modifications.

In one aspect, it is understood to a person skilled in the art that a moiety representing an antibody-derivative can be selected from a group consisting of a scFv (i.e., single-chain fragment variable), a Fab, a Fab', a F(ab')$_2$, a single domain antibody, a CrossMab, a VHH domain antibody, a nanobody, an IgG heavy chain, an IgG light chain, and an engineered or a combination of these antibody-derivative molecules thereof. In some embodiments, preferred antibody derivatives are a single chain (IgG heavy or light chain), a scFv, a Fab, a CrossMab, a VHH domain antibody, and a nanobody. In another aspect, it is also understood by an artisan that a non-antibody alternative scaffold can be selected from a group consisting of an Affibody, an Affilin, an Alphabody, a Knottin, a DARPin, an Anticalin, a Kunitz domain peptide, a FN3 scaffold, a Fynomer, a Cys-knots, a Monobody, an Affimer, and a lectin domain.

As would be understood by a person skilled in the art, a moiety representing a cytokine or cytokine-like molecule can be selected from a cytokine, a chemokine, a growth factor, an extracellular domain of a cell membrane protein, and a derivative or engineered form of these said cytokine or cytokine-like molecules, represented by a list consisting of IL-1α, IL-1β, IL-2, IL-2-like, CD132, IL-4, IL-5, IL-6, IL-6-like, IL-8, IL-9, IL-10, IL-10-like, LIF, OSM, IL-12, IL-13, IL-15, IL-17, IL-23, IL-25, IL-27, IL35, IL-38, G-CSF, GM-CSF, IFNβ, IFNγ, TGFβ, TNFα, TNFβ, a TNF superfamily member, CD154, LT-β, TNF-α, TNF-β, 4-1 BBL, APRIL, CD70, CD153, CD178, GITRL, LIGHT, OX40L, TALL-1, TRAIL, TWEAK, TRANCE, M-CSF, SCF, MSP, EPO, TPO, Flt-3L, and an extracellular domain of a cytokine receptor such as the extracellular domains of TGFβ-receptor and IL-15 receptor.

It is understood by a person skilled in the art that, in some embodiments, in addition to target-binding moieties, a non-target-binding moiety is included as an integral part of a bispecific or multispecific biologic. In some embodiments, a non-target-binding moiety serves to physically link two or more target-binding moieties together to form a single chimeric polypeptide or a subunit of the biologic. In some embodiments, a non-target-binding moiety is an "appendage" or chemical modification that serves to provide the biologic a favorable pharmaceutical or pharmacological property. The composition, length, stiffness, orientation, and format of a non-target-binding moiety is often crucial for the proper assembling and functional activity of a bispecific or multispecific biologic.

In some embodiments, a non-target-binding moiety is a peptide linker that covalently links two target-binding moieties in a single chimeric polypeptide. In several embodiments, peptide linkers are: (1) a flexible linker with a length of about 1 to about 49 amino acids, preferentially 2-30 amino acids, represented by a G/S rich linker such as $(G)_n$, $(SG)_n$, $(GS)_n$, $(GSG)_n$, $(GGS)_n$, $(GGGS)_n$ (SEQ ID NO: 1), $(GGSG)_n$ (SEQ ID NO: 2), $(GGGGS)_n$ (SEQ ID NO: 3), $(GGSGG)_n$ (SEQ ID NO: 4), $(GKPGS)_n$ (SEQ ID NO: 5), $(GKPGGS)_n$ (SEQ ID NO: 6), $(GKPGGGS)_n$ (SEQ ID NO: 7), wherein n is an integer between 1 and 9; (2) a rigid linker with a length of about 1 to about 49 amino acids, preferentially about 2-30 amino acids, represented by a E/A/P rich linker such as $A(EAAAK)_nA$ (SEQ ID NO: 8) and $T(A4T)_nAAA$ (SEQ ID NO: 9), wherein n is an integer between 1 and 8; (3) a peptide linker derived from a natural protein, represented by FNRGEC (SEQ ID NO: 10) and EPSGP (SEQ ID NO: 11) (derived from an IgG upper hinge region), LGGC (SEQ ID NO: 12) and VEPKEC (SEQ ID NO: 13) (derived from C-terminus of the kappa light chain of an IgG), and PSGQAGAAASESLFVSNHAY (SEQ ID NO: 14) (derived from human muscle aldolase); (4) a peptide sequence represented by AKTTPKLEEGEFSEAR (SEQ ID NO: 15), AKTTPKLEEGEFSEARV (SEQ ID NO: 16), AKTTPKLGG (SEQ ID NO: 17), SAKTTPKLGG (SEQ ID NO: 18), AKTTPKLEEGEFSEARV (SEQ ID NO: 19), SAKTTP (SEQ ID NO: 20), SAKTTPKLGG (SEQ ID NO: 21), RADAAP (SEQ ID NO: 22), RADAAPTVS (SEQ ID NO: 23), RADAAAAGGPGS (SEQ ID NO: 24), $RADAAAA(GGGGS)_{1-3}$ (SEQ ID NO: 25), SAKTTPKLEEGEFSEARV (SEQ ID NO: 26), ADAAP (SEQ ID NO: 27), ADAAPTVSIFPP (SEQ ID NO: 28), TVAAP (SEQ ID NO: 29), TVAAPSVFIFPP (SEQ ID NO: 30), QPKAAP (SEQ ID NO: 31), QPKAAPSVTLFPP (SEQ ID NO: 32), AKTTPP (SEQ ID NO: 33), AKTTPPSVTPLAP (SEQ ID NO: 34), AKTTAP (SEQ ID NO: 35), AKTTAPSVYPLAP (SEQ ID NO: 36), GPAKELTPLKEAKVS (SEQ ID NO: 37), ASTKGP (SEQ ID NO: 38), ASTKGPSVFPLAP (SEQ ID NO: 39), GENKVEYAPALMALS (SEQ ID NO: 40), GHEAAAVMQVQYPAS (SEQ ID NO: 41), and VEGGSGGSGGSGGSGGVD (SEQ ID NO: 42); (4) a combination between or among the foregoing (1), (2), (3) and (4) peptide linkers with various compositions or biophysical properties. In some embodiments, a non-target-binding moiety is a chemical linker that covalently links two target-binding moieties in a single chimeric fusion protein. Exemplary chemical linkers are polyethylene glycol (PEG), polylactic-co-glycolic acid (PLGA), polylactic acid (PLA), and poly(ε-caprolactone) (PCL). In some embodiments, preferred non-target-binding moiety is a peptide linker with a length of about 2-30 amino acids.

In some embodiments, a non-target-binding moiety comprised by a bispecific or multispecific biologic is a heterodimerization or multimerization domain, represented by a Fc or a Fc-derived domain of an IgG and a Dock-and-Lock (DNL) domain (e.g., a leucine zipper derived from cAMP-dependent protein kinase (PKA) and A kinase anchor proteins (AKAPs). In some embodiments, a preferred heterodimerization domain is a Fc or a derivative of Fc domain engineered to improve the stability of a bispecific or multispecific biologic, represented by a Fc mutated to possess biophysical features represented by the so-called "Knobs-in-Holes", "electrostatic steering", "Dock & Block®" or "XmAb®", which favor heterodimerization over homodimerization.

It is understood by an artisan that a further modification to a target-binding or a non-target-binding moiety of a bispecific or multispecific biologic can be made to achieve a favorable pharmaceutical and pharmacological property. In one embodiment, an albumin or a biocompatible polymeric molecule (e.g., PEG, polyethylene glycol) can be included in a bispecific biologic to prolong the biologic's serum half-life (i.e., a better pharmacokinetic profile). In an additional embodiment, a toxic molecule (e.g., doxorubicin or other therapeutic agent) can be linked to a bispecific antibody to improve its target-killing activity (e.g., a better efficacy). In an additional embodiment, point mutations (including those that affect glycosylation on certain residues of Fc), can be introduced in the Fc region of an IgG, wherein the mutations can reduce, abolish, or enhance the binding of Fc with a FcγR receptor, in connection with a reduced or enhanced ADCC activity of a bispecific antibody, which is primarily mediated by NK (natural killer) or NK-like cells via their FcγR-III receptors. For a further example, IL-2, a cytokine known to concomitantly bind to three distinct IL-2 receptor subunits (CD25, CD122, and CD132), may be mutated or PEGylated at certain amino acid residues to obtain an IL-2-like multispecific biologic with improved specificity biased for CD25 for autoimmunity-related therapeutic applications, or alternatively biased for its low-affinity target CD122 for cancer indications.

Two or more moieties comprised by a bispecific or multispecific biologic can target different molecular sites on a single target molecule, or on two or more, same or different, target molecules. By combining two or more functionally distinct moieties together in an integral biologic, dual- or multi-targeting can be achieved to enable improved (e.g., synergistic) targeting specificity, efficacy or both, that are favorable to a therapeutic application. For instance, a biologic representing a bispecific antibody may be assembled by integrating two distinct target-binding moieties selected from a list of antibodies and antibody-like molecules, that are intended to bind to two distinct molecular sites on a same target molecule or two distinct ones on a cell. Similarly, a tri-specific (aka, "trispecific") antibody may be formulated by integrating three distinct target-binding moieties selected from a list of antibodies and antibody-like molecules, that are intended to target three distinct molecular sites on the same or distinct target molecules on a single cell or on different cells. By combining or pairing the available versatile formats of antibodies and antibody-like molecules, it is appreciated that more than 100 different BsAbs or multispecific antibodies can be formulated. For example, Catumaxomab was the first bispecific biologic drug approved for the treatment of malignant ascites, which targets both CD3 (a T cell target) and EpCAM (a cancer cell target); Emicizumab, a bispecific IgG4-like antibody targeting Factors IXa and X, was approved for routine prophylaxis of bleeding episodes in people with hemophilia A with factor VIII inhibitors; Blinatumomab targeting CD3 and CD19 was approved for the treatment of certain forms of leukemia. Representative bispecific biologics in clinical development are: CD3×CD20 dual-targeting BsAb that engages a $CD3^+$ T cell and a $CD20^+$ cancer cell; CD3×BCMA dual-targeting BsAb that engages a $CD3^+$ T cell and a $BCMA^+$ cancer cell; HER2×HER2 dual-targeting BsAb that engages two molecule sites of HER2 molecules on a cancer cell; PD-L1×TGFβ dual-targeting immunocytokine that targets PD-L1 on a tumor cell and TGFβ in a tumor microenvironment; IL-2R×p53 dual-targeting biologic that comprise a IL-2 and a p53-specific single-molecule TCR (T cell receptor).

It is understood to a person skilled in the art that, two or more identical or near identical copies of a biologic moiety can be included in a single biologic molecule. In some embodiments, the increased copy number increases the target-binding valency or avidity of the said biologic, which can be advantageous for a therapeutic application.

According to several embodiments, a library of bispecific or multispecific biologic encoding genetic materials, each encoding a single genetic variant and collectively a diversified variant pool of the said biologics, can be engineered from genetically combining or pairing a pool of target-binding and non-target-binding moieties (e.g., domains from lead antibody candidates derived from antigen-naïve and immunized animals, and human subjects). The genetic library can also be generated or further diversified by direct DNA synthesis, error-prone or parsimonious Polymerase Chain Reactions (PCRs), genetic editing, or by a recombination approach such as DNA shuffling and Gibson Assembly, using pre-existing biologic-expression DNAs as seed templates. For example, in the case for a bispecific antibody, such seed templates may be derived from a common screening process for a primary antibody by a person skilled in the art.

In some embodiments, a select cell type can be engineered to express a diversified library of bispecific or multispecific biologics, wherein each individual cell expresses a single variant of the said biologics, and collectively these cells constitute a biologic-expressing cell library. It is understood that a person skilled in the art may generate a single-variant expressing cell library via retrovirus- or lentivirus-mediated genomic integration of a genetic library of the said biologics into the said select type of cells. In some embodiments, to ensure single-variant integration into the cell genome, a low Multiplicity-of-Infection (MOI) of virus is used, e.g., using a low virus-to-cell ratio for cell infection, with a MOI below for example one or 0.5. With a retroviral or lentiviral approach, highly efficient genomic integration (up to 95% efficiency) can typically be achieved. In some embodiments, a CRISPR- or recombinase (such as integrase or transposon) based genetic engineering approach, or transient transfection and selection, can be utilized to meditate a single-insertion of a biologic-expressing DNA material. In some embodiments, with a CRISPR- or recombinase-based method, a reasonably high efficiency of genomic integration can be achieved, particularly for those transfection-compatible cells such as CHO, 293, and HeLa cells (up to about 30% efficiency). As used herein, the terms "single variant", "single-variant" and "single genetic-variant" can be used interchangeably, which generally refer to a single genetic-coding sequence or two or more copies of identical genetic-coding sequences representing the same variant, in a given single cell.

Figure 2:
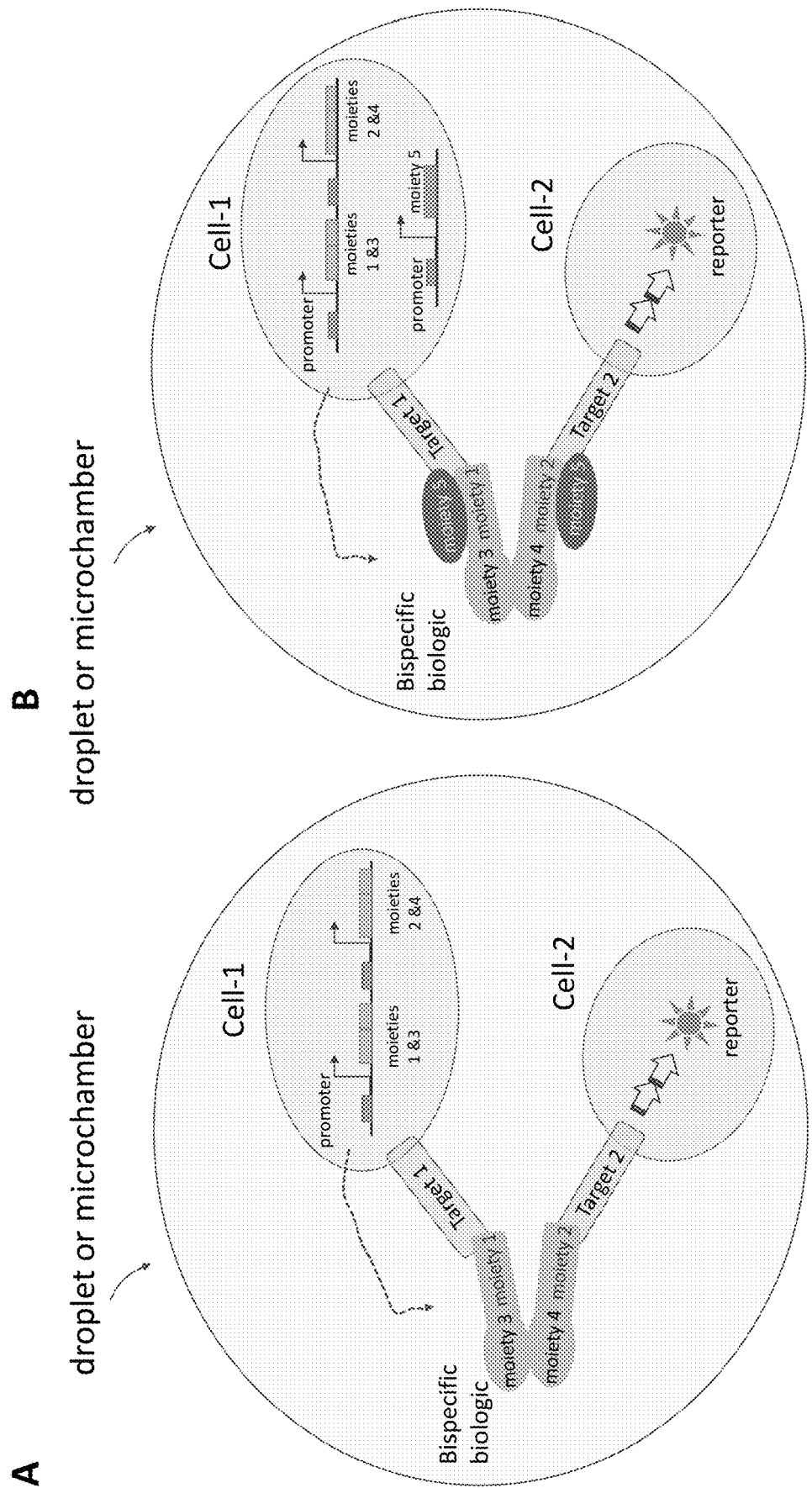
FIGS. 2, (A) and (B) depict general principles and features of some embodiments of a compartmentalized nano-volume based assay for a dual-target binding bispecific biologic.

In some embodiments, all necessary moieties of a bispecific or multispecific biologic are integrated into a single artificial fusion protein that is encoded by a single gene-expression cassette. As such, a single genomic integration event is adequate to create a biologic expressing cell. In some embodiments, the moieties of a biologic are spread into two or more distinct expression cassettes. The said expression cassettes can be further assembled as a single expression vehicle, and subsequently integrated into a single genomic locus of a cell type of choice. In some embodiments, the cassettes can be respectively inserted into two or more distinct genomic loci through two or more recombination events. In some embodiments, the cassettes shall be inserted into no more than two distinct genomic loci as illustrated in FIGS. 1 and 2.

As used herein, the term "genomic integration" is used interchangeably as genomic insertion or recombination. As used herein, the term "gene expression cassette" shall be given its ordinary meaning and generally refers to a DNA construct comprising a gene promoter, a gene-coding open reading frame, a stop codon, and a poly-adenylation signal element, and one or more optional regulatory DNA elements. Optionally, in the format of a single expression cassette, two or more open reading frames, each encoding at least one biologic moiety, can be concatenated via an IRES (internal ribosome entry site) or a self-cleaving sequence (e.g., P2A, F2A, E2A and T2A peptides), yet still under the control of a single gene promoter. As used herein, the term "expression vehicle" generally refers to a DNA construct that comprises two or more expression cassettes, including those encoding biologic moieties and optionally a selection marker.

A biologic-expressing cell library may be enriched by using a selection marker, wherein the negative populations (those not integrated with a biologic-expressing genetic material) are minimized or removed.

It is generally understood that a select type of cell for expressing a biologic can be a human cell, an animal cell, a fused hybrid cell, a hybridoma cell, a fungal cell, a yeast cell, an engineered eukaryotic cell, a virally infected cell, a transfected cell, an insect cell, or a drug-treated cell. In some embodiments, a yeast expression system is utilized to create a large library (with up to $10^8$ clone diversity) of a biologic with at least two polypeptide subunits that are linked through heterodimerization or trimerization. For example, on one hand, a first library of haploid yeast strain with mating type a is generated by transforming a plurality of genetic variants, each representing one subunit, and a second library of haploid yeast strain of mating type a is generated by transforming a plurality of genetic variants, each representing the remaining subunit(s). Mating of the two said yeast libraries with opposite mating types may create a combinatorial diploid yeast library, wherein each diploid yeast cell expresses substantially a single variant of the said biologic.

In some embodiments, at least one moiety comprised by a bispecific or multispecific biologic is provided with a secretion signal, for example at its N-terminal end. As used herein, secretion signal interchangeably refers to leader sequence, leader peptide, signal peptide, or signal sequence, which is used to direct the secretion of individual biologic moieties or a properly assembled biologic as a whole, into an extracellular space. In some embodiments, at least one moiety comprised by a bispecific or multispecific biologic is provided with a membrane-anchoring domain which is removable via an exon-skipping or leaky stop-codon mechanism, wherein upon conditional removal of the membrane-anchoring domain, a portion of the biologics in a given cell will be tethered to a cell surface membrane, and in the meantime, another portion will be secreted into the extracellular space.

In some embodiments, one or more reporter cells are provided in a compartmentalized assay together with a first type cell that expresses and secretes a certain single variant of a bispecific or multispecific biologic. The said reporter cell is in part selected based on its inherent ability to stably express, or is genetically engineered to stably express, an adequate amount of at least one intended target molecule for the said biologic. In some embodiments, the said first cell may also express a distinct target molecule; together, the said first and second cells express all intended target molecules of the said biologic, as illustrated by, for example FIGS. 1 through 8. In some embodiments, a reporter cell shall be a human cell, an animal cell, a fused hybrid cell, a virally infected cell, a transfected cell, a drug-treated cell, an insect cell, a yeast cell, or a derivative or engineered form of these said cells.

Figure 25:
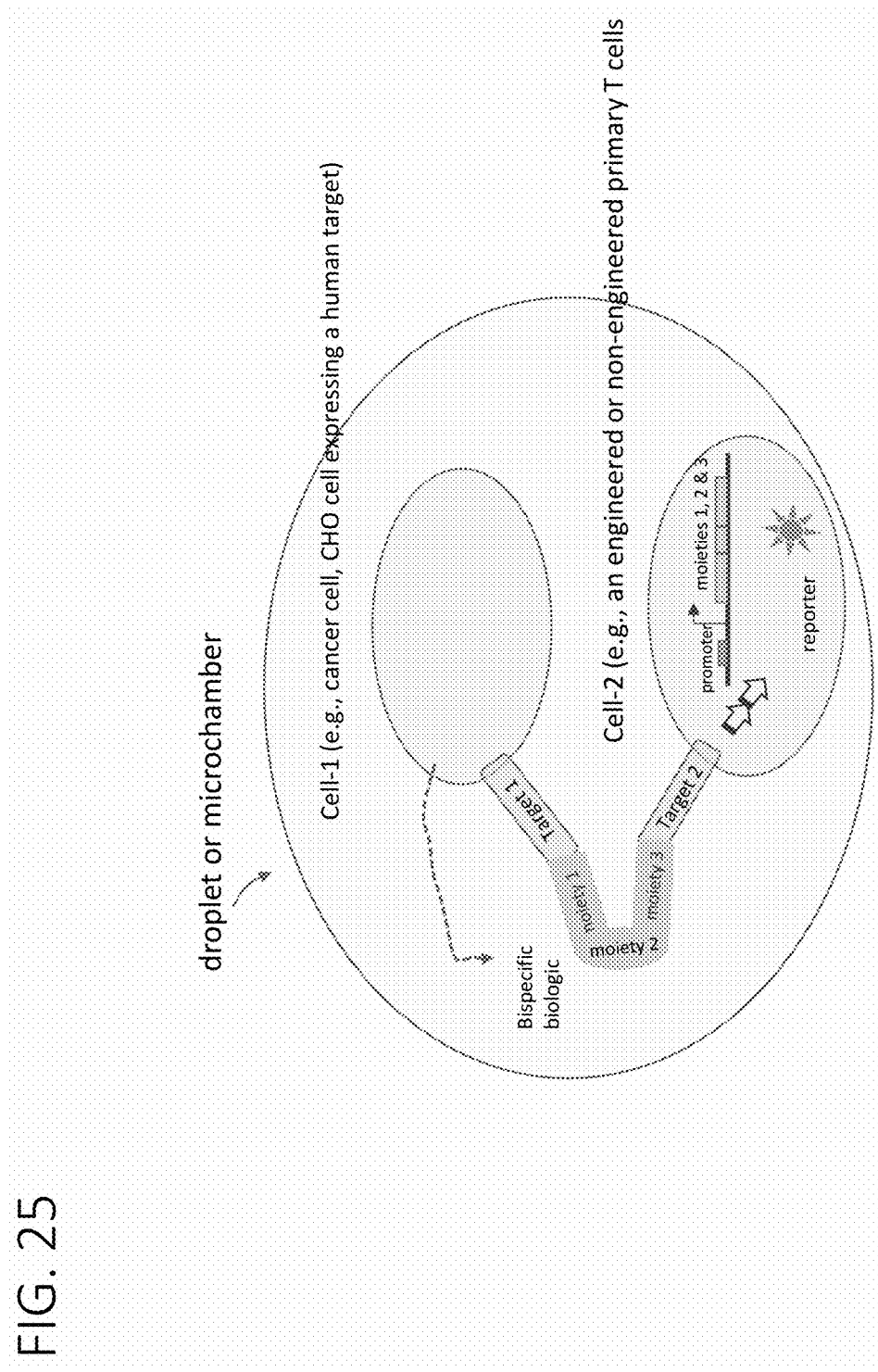
FIG. 25. Alternative design for encoding of subunits. All components (subunits) encoding the biologic are integrated into cell-2.

In some embodiments, as exemplified in FIG. 25, a reporter cell is selected to be engineered with all moieties of a single bispecific or multispecific biologic variant per cell, and meanwhile all intended targets or at least intended one target for the said biologic is expressed by a second-type cell.

In some embodiments, at least one cell of a second type (for example, the reporter cell) is provided in an assay together with a first cell that expresses and secretes a certain single-variant of a bispecific or multispecific biologic. The said reporter cell is in part selected based on its inherent ability to stably express, or is genetically engineered to stably express, an adequate amount of at least one intended target molecule for the said biologic. In some embodiments, the said first cell may also express a distinct target molecule; together, the said first and second cells express all intended target molecules of the said biologic, as illustrated by, for example FIGS. 1 through 8. In some embodiments, a reporter cell shall be a human cell, an animal cell, a fused hybrid cell, a virally infected cell, a transfected cell, a drug-treated cell, an insect cell, a yeast cell, or a derivative or engineered form of these said cells.

In some embodiments, three distinct types of cells are provided in a compartmentalized assays, wherein a first cell is engineered to express a single variant of a bispecific or multispecific biologic, one or more cells of a second type is selected or engineered to serve as a reporter cell, and one or more cells of a third type are selected or engineered as a target-expression cell which expresses at least one distinct type of intended targets for the said biologic. For example, an NK (or NK-like) cell may be included in a droplet together with a target-expressing cancer cell and a common-light-chain BsAb expressing cell, to demonstrate the NK-dependent ADCC activity (antibody dependent cellular cytotoxicity) of the secreted BsAb towards the cancer cell.

In some embodiments, reporter cells are selected based on its ability to, or genetically engineered to, produce a reporter signal upon specific-binding and functional modulation by a properly assembled functional biologic. As used herein, functional modulation generally refers to neutralization, blocking, activation, clustering, endocytosis or degradation, of the intended target molecules; to a lesser extent, functional modulation may refer to an acquired new biological function, or programmed death of the said reporter cell. As used herein, reporter signal generally refers to an intracellular, a cell surface, or an extracellular molecule or signal, the abundance of which is subject to the direct or indirect regulation of the said biologic, and the intensity or presence of which is detected using an established method and tool of choice.

In some embodiments, the reporter signal is derived from a genetically driven reporter gene, wherein the transcriptional activation of the said reporter gene is controlled by a promoter with a response element that is responsive to the functional modulation of targets by a biologic. In some embodiments, the reporter signal is a cellular factor whose abundance is regulated at the post-transcriptional or translational level by the said biologic. In some embodiments, the reporter signal is a small molecule such as cAMP, cGMP, and calcium, wherein its abundance is subject to the functional activity of the said biologic.

In some embodiments, the reporter gene encodes a transcriptionally driven, optically detected fluorescent protein, wherein the said reporter gene is under the control of a promoter with a response element that is responsive to the functional activity of a bispecific or multispecific biologic. Exemplary fluorescent proteins are blue fluorescent proteins such as BFP and mTagBFP, cyan fluorescent proteins such as ECFP and TagCFP, green fluorescent proteins such as EGFP and ZsGreen, yellow fluorescent proteins such as EYFP and ZsYellow1, red fluorescent proteins such as mRFP and mCherry, far-red proteins such as E2-Crimson, a derivative or engineered form of a fluorescent protein, and a cleavable fluorogenic chimeric protein that may yield a mature fluorescent polypeptide upon cleavage by an enzyme that is induced by a functional biologic. It is understood that the coding sequences for the foregoing fluorescent and fluorogenic proteins are publicly accessible to a person skilled in the art or are available from a variety of commercial sources.

In some embodiments, the reporter gene encodes a fluorogenic protein which may produce a fluorescent signal upon catalysis of a provided suitable fluorogenic substrate, wherein the said reporter gene is under the control of a promoter with a response element that is responsive to the functional activity of a bispecific or multispecific biologic. Exemplary fluorogenic proteins are a certain form of β-galactosidases, phosphatases, peptidases or proteases. Exemplary fluorogenic substrates for a β-galactosidase are fluorescein digalactosides, resorufin galactosides, and dimethylacridinone (DDAO) galactosides. Exemplary fluorogenic substrates for a phosphatase are fluorescein diphosphates, DDAO phosphates, and methylumbelliferyl phosphates (MUP). Exemplary fluorogenic substrates for a peptidases or protease are chemicals based on a 7-Amino-coumarin backbone such as 7-Amino-4-methylcoumarin, and those based on a Rhodamine-110 backbone such as bis-(CBZ-Arg)-R110. It is understood that the coding sequences for the foregoing said fluorogenic proteins and the relevant fluorogenic substrates are readily accessible to a person skilled in the art, or widely available from a variety of commercial vendors or may be made in a chemistry lab by a person skilled in the art.

In some embodiments, the reporter gene encodes a luminescent protein, wherein the said gene is under the control of a promoter with a response element that is responsive to the functional activity of a bispecific or multispecific biologic. Exemplary luminescent proteins are Firefly™ luciferase, Renilla™ luciferase, NanoBiT™ luciferase, and a derivative or an engineered form of a luciferase.

In some embodiments, the reporter gene encodes a luminogenic protein, wherein the said gene is under the control of a promoter with a response element that is responsive to the functional activity of a bispecific or multispecific biologic. Exemplary luminogenic proteins are certain isoforms of cytochrome P450 or N-acetyl-transferase-2 (NAT2) wherein a corresponding luminogenic substrate is pro-luciferin.

In some embodiments, the reporter signal is a fluorescent sensor dye for a cell metabolic product, or for an ion such as calcium, zinc and magnesium, wherein the level of the said cell metabolite or the flux of the said ion in a cell can be subject to the regulation by a functional activity of a bispecific or multispecific biologic on an intended cell surface target such as an ion channel. In some embodiments, the exemplary ion is calcium, wherein the calcium flux through an ion channel target can be optically detected using fluorescent sensor dyes such as Fura-2 AM, Fura Red AM, Fluo-4 Direct, and Indol-1 AM.

In some embodiments, the reporter signal is a fluorescent sensor dye for an effector or messenger molecules such as cAMPs and cGMPs, wherein the cellular level of the said effector molecules is responsive to the functional status of a G Protein Coupled Receptor (GPCR), a class of highly attractive therapeutic targets.

In some embodiments, the reporter signal is derived from a matched pair of a donor and an acceptor that are capable of Foster Resonance Energy Transfer (FRET), or AlphaLISA® based luminescent signal amplification, wherein the said donor is conjugated with a first target, and the said acceptor is conjugated with a second target. In some embodiments, when a functional bispecific biologic that is expressed and secreted in a compartmentalized nano-volume binds to the said first and second targets at the same time, such that the two said targets are within a desired short distance (i.e., within the Foster radius of the FRET pair), then FRET may occur upon excitation. The said FRET may be optically detected as emission light signal, which indicates the presence of a functional bispecific biologic.

It is understood that a person skilled in the art may readily establish a reporter expression cassette comprising a target-responsive promoter and a reporter coding gene, through a variety of approaches including viral integration, CRISPR-mediated recombination, landing-pad mediated site-specific recombination, and random integration.

In some embodiments, the reporter is an effector gene that is in a biological regulatory pathway downstream of a target molecule intended for a bispecific or multispecific biologic. The activation of such a reporter by the said biologic can be genetically detected, for example, through a linkage PCR, wherein a common oligo-DNA primer is provided to prime the PCR from at least two genetic regions: (a) a genetic sequence representing a portion or whole of a bispecific or multispecific biologic, and (b) a genetic sequence representing an effector gene that is responsive to the functional activity of a properly assembled functional biologic. Exemplary effector genes are those encoding effector cytokines such as IL-2, IL-6, IL-10, TNFα, IFNγ, and effector enzymes such as perforins and granzymes, wherein the upregulation of the said effectors can be induced by a functional bispecific antibody that targets a T Cell Receptor in one arm and a tumor antigen in the other arm.

In some embodiments, among a genetic library engineered to include random diverse combinations or pairings from individual moieties of a bispecific or multispecific biologic, most of the combinations or parings will not efficiently lead to a biologic with a proper functional activity. It is well appreciated in the art that in some embodiments only a small portion (0.3% or lower) of biologic variants are properly assembled and show a functional activity. Traditionally, the assays for those rare functional clones heavily rely on multiple rounds of screenings based on a microtiter-well plate format, which is often tedious, highly inefficient and costly. Alternatively, one may choose to display individual variants of a bispecific or multispecific biologic on cell surface, followed by multiple rounds of flow cytometric screenings and functional validation. Such alternatives are similarly inefficient in part because it screens for binders rather than functional activity. As used herein, clone can be used interchangeably as variant. As such, single variant shall refer to single clone.

In some embodiments, a plurality of compartmentalized nano-volumes, in particular microchambers and water-in-oil droplets, are used as a microreactor system of biological assays to directly and rapidly screen for functional single variants from an engineered library of bispecific or multispecific biologics in an ultra-high throughput manner. In some embodiments, the throughput of compartmentalized nano-volumes is from about 10,000 to about 800 million, from about 40,000 to about 100 million, or from about 100,000 to about 20 million.

In some embodiments, a compartmentalized nano-volume comprises a first cell that is engineered to express a single variant of each and all necessary moieties of a bispecific or multispecific biologic, and at least a second cell that serves as a reporter cell that produces a reporter signal indicating a functional biologic expressed and secreted from the said first cell.

Some embodiments include the use of microfluidics. In one aspect, microfluidics allows the partitioning of a bulk pool of heterogeneous samples into many isolated, small-volume compartments to quickly increase the effective analyte concentration and simultaneously reduce interferences from irrelevant species present in the same bulk samples. In another aspect, it combines the ability of compartmentalization, the flexibility of fluidic manipulation and the capacity for ultra-high throughput screening at the single cell level.

It is expected that a person skilled in the art may readily produce a plurality of microfluidic microchambers or droplets. For example, droplets encapsulated with one or more cells at a quick speed (up to thousands of droplets per second), by using a syringe- or pressure-pump, a microfluidic chip with a flow-focus or T-junction geometry, and a biocompatible oil such as 3M™ Novec-7500™ oil and Fluorinert™ FC40 oil, supplemented with a biocompatible surfactant, all of which are accessible via commercial vendors or in a properly equipped mechanical or biomedical engineering lab or a micro-electro-mechanical systems (MEMS) core facility.

In some embodiments, a compartmentalized nano-volume has a sub-nanoliter or nanoliter size, ranging from about 0.05 nL to about 10 nL, about 0.03 nL to about 100 nL, from about 0.1 nL to about 4 nL, from about 0.1 nL to about 1 nL or from about 5 nL to about 10 nL. In some examples, the nano-volume is about 0.1 nL, 0.2 nL, 0.3 nL, 0.4 nL, 0.5 nL, 0.6 nL, 0.7 nL, 0.8 nL, 0.9 nL, 1 nL, 2 nL, 3 nL, 4 nL, 5 nL, 6 nL, 7 nL, 8 nL, 9 nL, 10 nL, 11 nL, 12 nL, 13 nL, 14 nL, 15 nL, 16 nL, 17 nL, 18 nL, 19 nL, 20 nL, 21 nL, 22 nL, 23 nL, 24 nL, 25 nL, 26 nL, 27 nL, 28 nL, 29 nL, 30 nL, 31 nL, 32 nL, 33 nL, 34 nL, 35 nL, 36 nL, 37 nL, 38 nL, 39 nL, 40 nL, 41 nL, 42 nL, 43 nL, 44 nL, 45 nL, 46 nL, 47 nL, 48 nL, 49 nL, 50 nL, 51 nL, 52 nL, 53 nL, 54 nL, 55 nL, 56 nL, 57 nL, 58 nL, 59 nL, 60 nL, 61 nL, 62 nL, 63 nL, 64 nL, 65 nL, 66 nL, 67 nL, 68 nL, 69 nL, 70 nL, 71 nL, 72 nL, 73 nL, 74 nL, 75 nL, 76 nL, 77 nL, 78 nL, 79 nL, 80 nL, 81 nL, 82 nL, 83 nL, 84 nL, 85 nL, 86 nL, 87 nL, 88 nL, 89 nL, 90 nL, 91 nL, 92 nL, 93 nL, 94 nL, 95 nL, 96 nL, 97 nL, 98 nL, 99 nL or 100 nL.

In some embodiments, a compartmentalized nano-volume may further comprise a detection reagent that is used to label a reporter signal to enable optical detection. For instance, a fluorescent sensor dye specific to cAMP or calcium may be co-encapsulated into a droplet with a biologic-expressing cell and a reporter cell. Positive dual-targeting function of an expressed biologic clone on an assumed GPCR or ion channel target will trigger the cellular accumulation of cAMP or calcium that is then optically detected by an optical detection module.

In some embodiments, the intended target molecules for a bispecific or multispecific can be expressed mainly on the surface of a first cell that is engineered to express the said biologic, or mainly on a second cell that serve as a reporter cell, or mainly on a third cell that is a target-positive cell or used to concomitantly serve as another distinct reporter cell. In some embodiments, the target molecules are respectively distributed on two or three of the said first, second, and third cells as illustrated in FIGS. 1-8. The said first, second and third cells may be selected for its inherent ability to express a target on its cell surface, or engineered to stably express the said target, which can be achieved using a genomic integration method such as a lentiviral or retroviral method, a CRISPR/cas9 mediated genetic editing method, and a recombinase-mediated approach.

In some embodiments, one or more distinct types of cells are co-provided into a droplet through co-encapsulation using a droplet generating device. Under a random distribution circumstance, the percentage of droplets comprising exactly a single cell generally follows a certain Poisson statistic, such that droplets with one single cell is of a low percentage (about 32%), and droplets with two types of cells are of even lower abundance (about 10%). In some embodiments, to improve the percentage of droplets containing paired cells of two or more distinct types, a plurality of each cell type can be respectively ordered via an inertial microfluidic flow method right before the step of co-encapsulation into a droplet. In some embodiments, a first cell is encapsulated into a first droplet, a second cell separately into a second droplet, and then the said two first and second droplets are coalesced to become a single yet bigger droplet (i.e., two droplets merged into one).

In some embodiments, a suitable culture medium is provided in compartmentalized nano-volumes to promote the survival and functionality of cells in the said droplet. Such a culture medium may be further modified to be more compatible with a compartmentalized environment. For example, additional fetal bovine serum, non-essential amino acids, glutamine, and glutamate plus some anti-oxidant chemicals (e.g., β-mercaptoethanol), may be included to favor the survival of cells in a droplet or microchamber. It is understood that a person skilled in the art may readily procure the foregoing medium components through commercial vendors.

In some embodiments, compartmentalized nano-volumes containing provided live cells can be incubated over a period of time in a microfluidic device (e.g., on-device) or in a container, a chamber, a vial or a tube (e.g., off-device), in the presence of one or more environmental control modules selected from a list consisting of a temperature control module (with a temperature range from, for example, about 4° C. to about 37° C.), an oxygen control module (with a $O_2$ level from, for example, about 0.0001% to about 20%), a carbon dioxide control module (with a $CO_2$ level from, for example, about 0.1% to about 20%), and a humidity control module (with a humidity level from, for example, about 40% to about 99%).

In some embodiments, compartmentalized nano-volumes containing live cells can be detected by using a proper reporter signal detector. Exemplary detectors are an optical detector for detecting optical signals such as fluorescence and luminescence signals. Exemplary optical detector is a detection module that in part comprises a photon sensor and a signal amplification unit, which can be selected from a group consisting of a charge-coupled device (CCD) camera, a complementary metal-oxide semiconductor (CMOS) sensor, a photomultiplier (PMT), and an avalanche photodiode (APD). The detection module can be connected to a signal acquisition and processing board, which can be integrated with a computer equipped with a process-control or user interface software. Collecting data representing a positive reporter signal can be performed by collecting optical signals produced by accumulated reporters that are triggered by a functional biologic.

In some embodiments, collecting data representing a positive reporter signal are performed at one time-point, or two, three or more time-points. In some embodiments, the reporter detection and data processing are performed in a real-time or non-real-time mode, wherein the presence of a positive reporter signal will trigger a downstream sorting step to recover the biologic-expressing cell from a nano-volume with the positive reporter signal.

In some embodiments, the sorting of a droplet is performed using a sorting module based on a dielectrophoretic (DEP), an acoustic, a microvalve, a piezoelectric, a dynamic stream deflection, or an electrical capacitance mechanism. In some embodiments, the sorting is performed using a DEP- or acoustic-based sorting module. In some embodiments, the recovery of a cell in a microchamber is performed using a micro-pipette module. As used herein, the term "sorting" is often used interchangeably with "retrieving" or "recovering" in a controlled manner in the context of isolating one or more cells from a compartmentalized nano-volume.

In some embodiments, sorted cells are lysed using a commonly available lysis buffer, and then are subject to reverse transcription (RT) and one or more rounds of PCR to amplify DNAs representing biologic-coding sequences. The amplified DNAs are then subject to DNA sequencing and necessary genetic analysis. It is understood that these RT-PCR, sequencing and genetic analysis steps are generally known to a person skilled in the art.

In some embodiments, products of manufacture as provided herein are synchronized or integrated with digital communication and computer or mobile device applications. In some embodiments, products of manufacture as provided herein are used in assays for detecting and quantifying a chemical, biological, or a single cell in a single-plex, duplex-, or multi-plex assay format.

In some embodiments, the cell is a human cell, an animal cell, a fused hybrid cell, a hybridoma cell, a fungal cell, a yeast cell, an engineered eukaryotic cell, a virally infected cell, a transfected cell, or a drug-treated cell. Optionally a heterogeneous cell pool of a select type can be partitioned into individual droplets or microchambers, and characterized, imaged, manipulated and sorted at a single-cell level. Optionally a plurality of compartmentalized nano-volumes may contain not only 1-to-1 perfectly paired cells of two distinct types, but also zero cell, a single cell, or two or more cells of the same or different types.

Non-Limiting and Illustrative Embodiments

FIG. 1, (A) illustrates general concepts and schemes of some embodiments of a nano-volume (microfluidic droplet or microchamber) based assay for a bispecific single fusion protein, wherein a provided first cell is engineered to express three moieties of the said biologic through a single integrated genomic locus, wherein a provided second cell is selected or engineered to produce a reporter signal that is triggered by the said biologic, wherein the said biologic, upon properly assembling and secretion in the extracellular space as a functional form, is intended to target a first target expressed on the surface of the said first cell, and a second yet distinct target expressed on the said reporter cell. FIG. 1, (B) illustrates similar assay principles and features as FIG. 1, (A), except that the bispecific biologic comprises four functional moieties spreading into two distinct subunits inserted into two genomic loci, wherein two non-target-binding moieties (moiety-3 and moiety-4) are provided as heterodimerization domains.

FIG. 2, (A) shows general concepts and schemes of some embodiments of a nano-volume (droplet or microchamber) based assay for a bispecific biologic comprising four distinct moieties, which shares similar assay principles and features as FIG. 1, (B), except that the biologic expression vehicle is inserted into a single genomic locus. FIG. 2, (B) illustrates similar assay principles and features as FIG. 2, (A), except that the bispecific biologic comprises one additional moiety (moiety-5), wherein the said moiety-5 is expressed from an expression cassette inserted into a distinct genomic locus; moiety-5 is also involved in target binding in part through direct interaction with moiety-1 and moiety-2 respectively.

Figure 3:
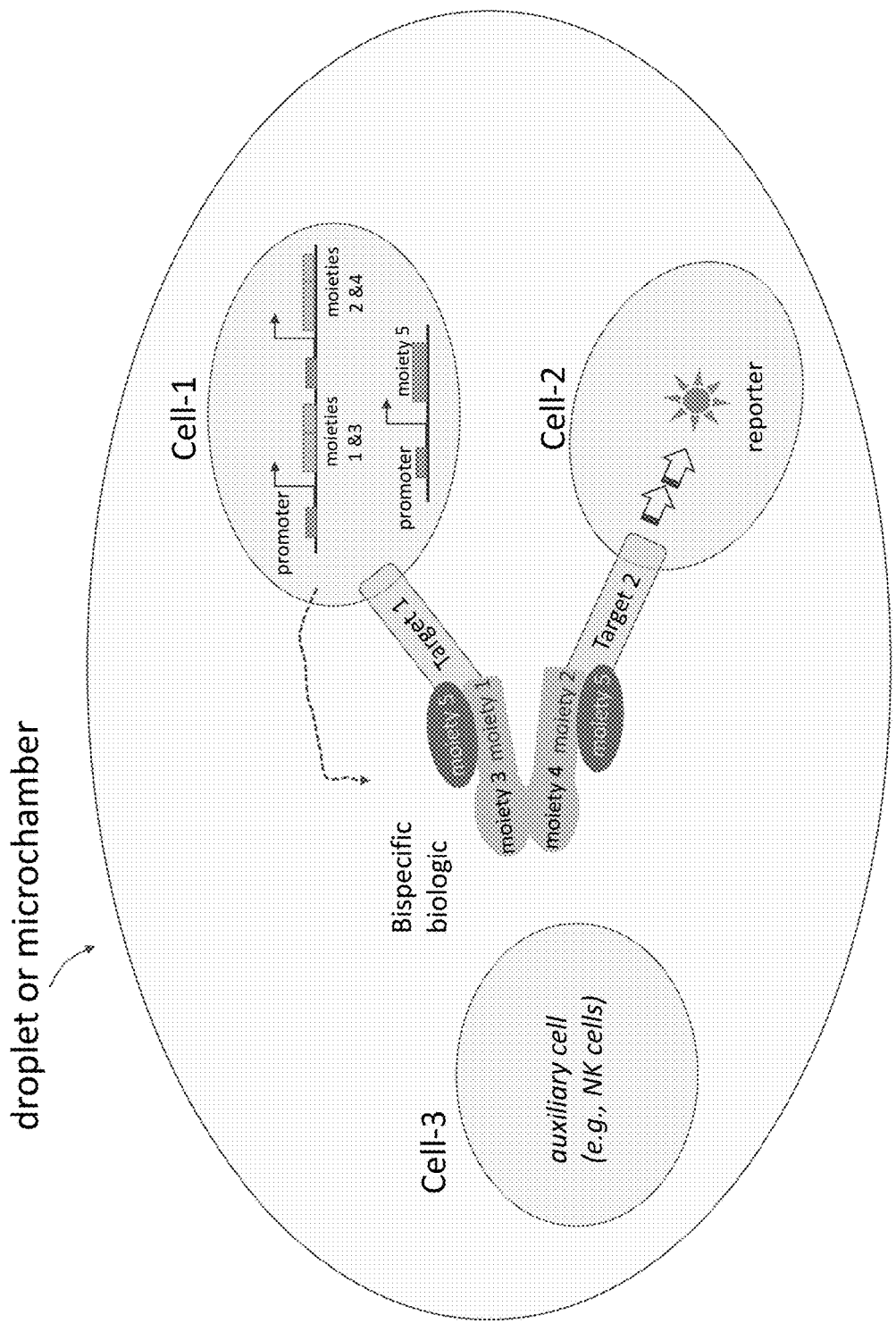
FIG. 3 is a schematic illustrating a general principle and features of some embodiments of a compartmentalized nano-volume based assay with three cells of distinct types for a dual-targeting bispecific biologic.

FIG. 3 depicts general concepts and schemes of some embodiments of a nano-volume (droplet or microchamber) based assay for a bispecific biologic, wherein a first cell is provided, which is engineered to express five moieties of the said biologic through two integrated genomic loci, wherein a second cell is provided, which is selected or engineered to produce a reporter signal that is triggered by the said biologic, wherein the said biologic, if properly assembled and secreted in a functional form, is intended to target two distinct types of targets expressed on the said first and second cells respectively, wherein a third cell is also provided to elicit or promote the biologic function, or to serve as a reporter cell with a distinct reporter from the second one.

Figure 4:
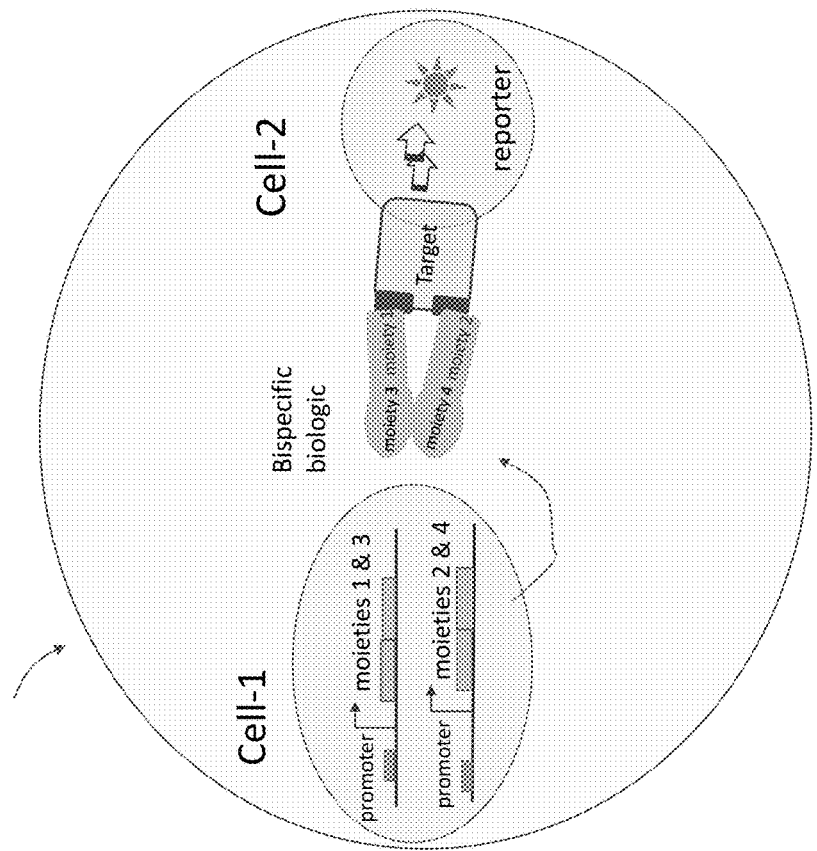
FIGS. 4, (A) and (B) are schematics illustrating general principles and features of some embodiments of a compartmentalized nano-volume based assay for a one-target-two-site binding bispecific biologic.
Figure 4:
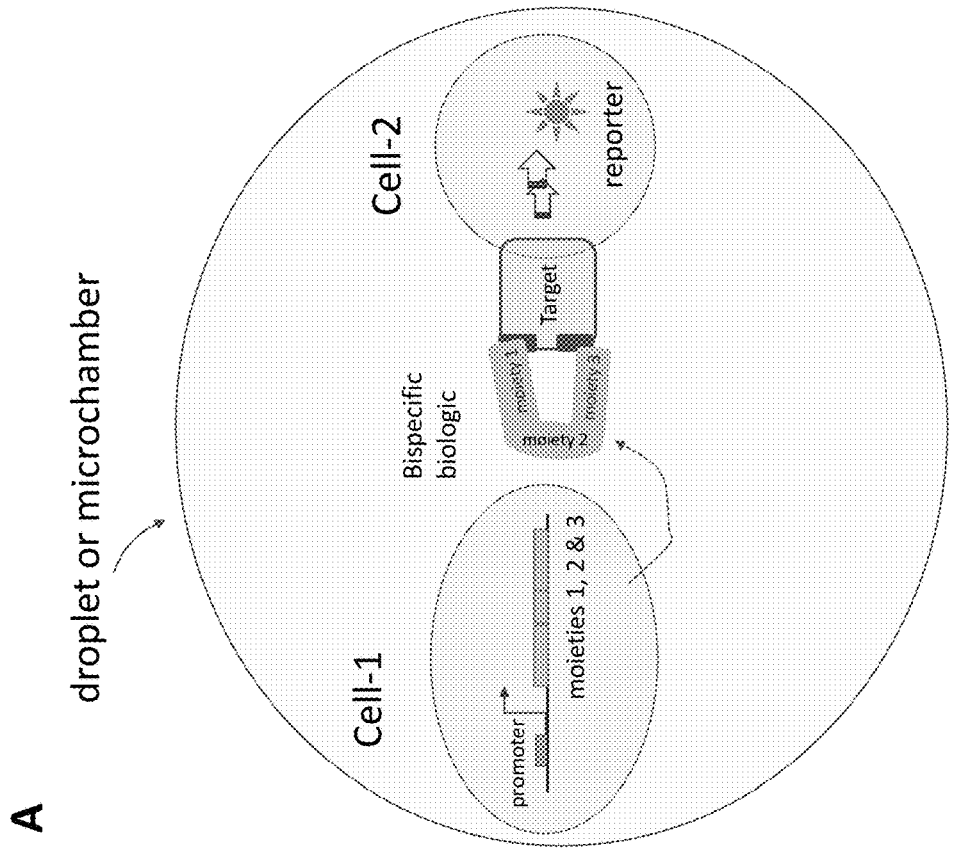

FIG. 4, (A) shows general concepts and schemes of some embodiments of a nano-volume (droplet or microchamber) based assay for a bispecific biologic, which shares similar assay principles and features as FIG. 1, (A), except that the said biologic is expected to target two distinct molecule sites on a same target molecule expressed on the reporter cell. FIG. 4, (B) illustrates similar assay principles and features as FIG. 1, (B), except that the said biologic is expected to target two distinct molecule sites on a same target molecule expressed on the reporter cell.

Figure 5:
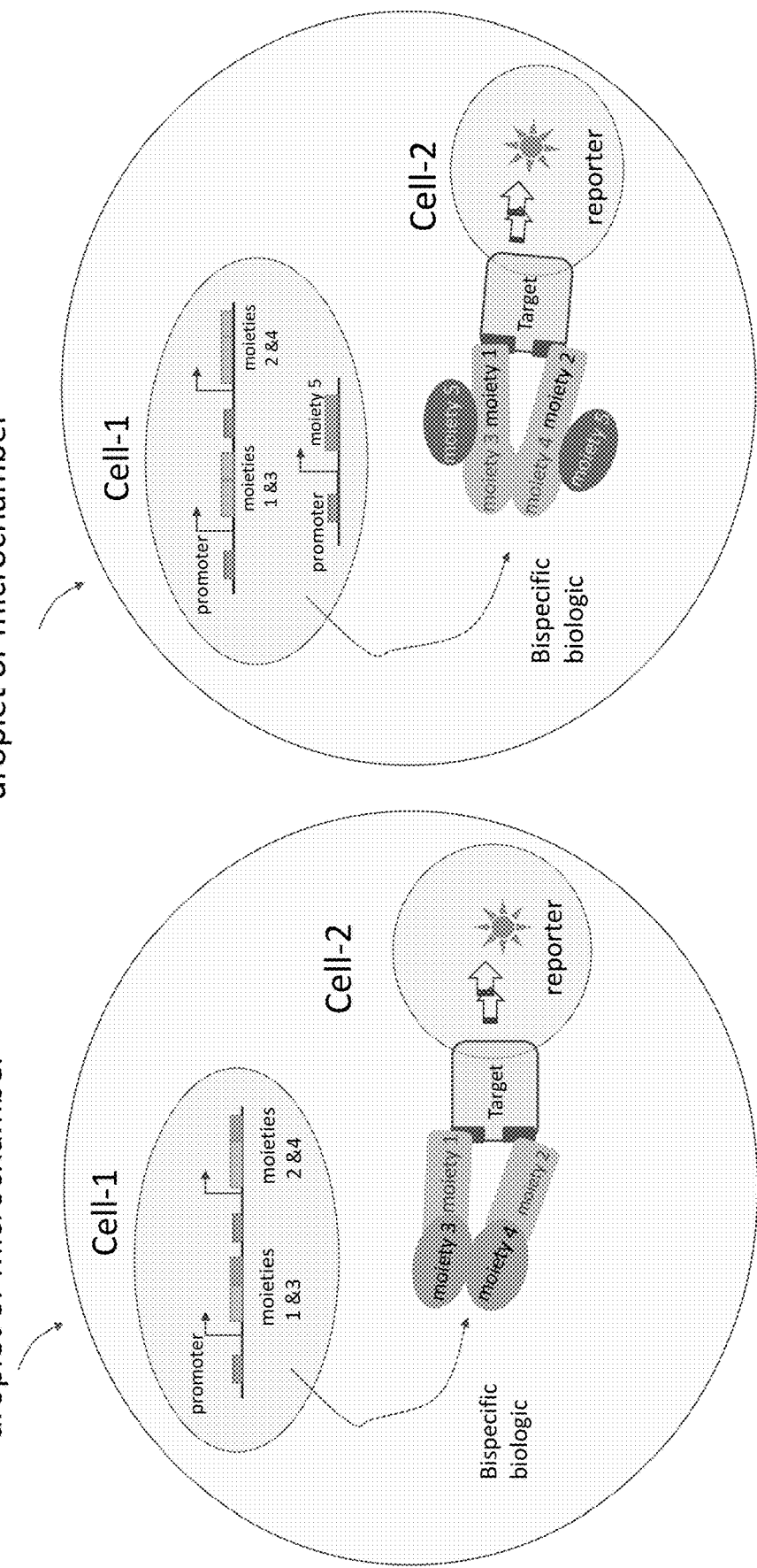
FIGS. 5, (A) and (B) depict general principles and features of some embodiments of a compartmentalized nano-volume based assay for a triple-target-binding multispecific biologic.

FIG. 5, (A) illustrates general concepts and schemes of some embodiments of a nano-volume (droplet or microchamber) based assay for a bispecific biologic, which shares similar assay principles and features as FIG. 2, (A), except that the said biologic is expected to target two distinct molecule sites on a same target molecule expressed on the reporter cell. FIG. 5, (B) illustrates similar assay principles and features as FIG. 2, (B), except that the said biologic is expected to target two distinct molecule sites on a same target molecule expressed on the reporter cell.

Figure 6:
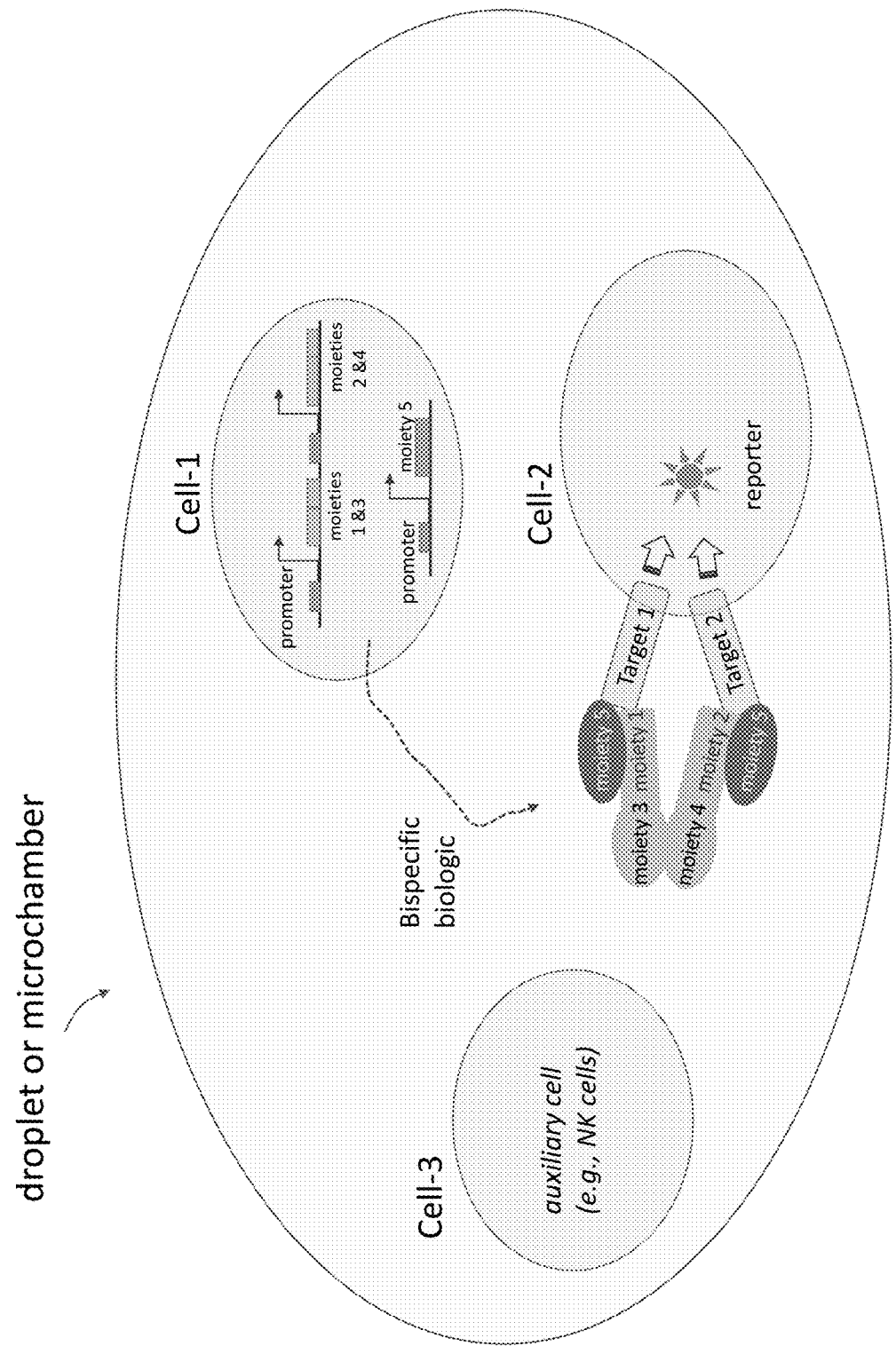
FIGS. 6, (A) and (B) depict general principles and features of some embodiments of a compartmentalized nano-volume based assay with three cells of distinct types for a dual-target-binding bispecific biologic comprising three or four moieties.
Figure 6:
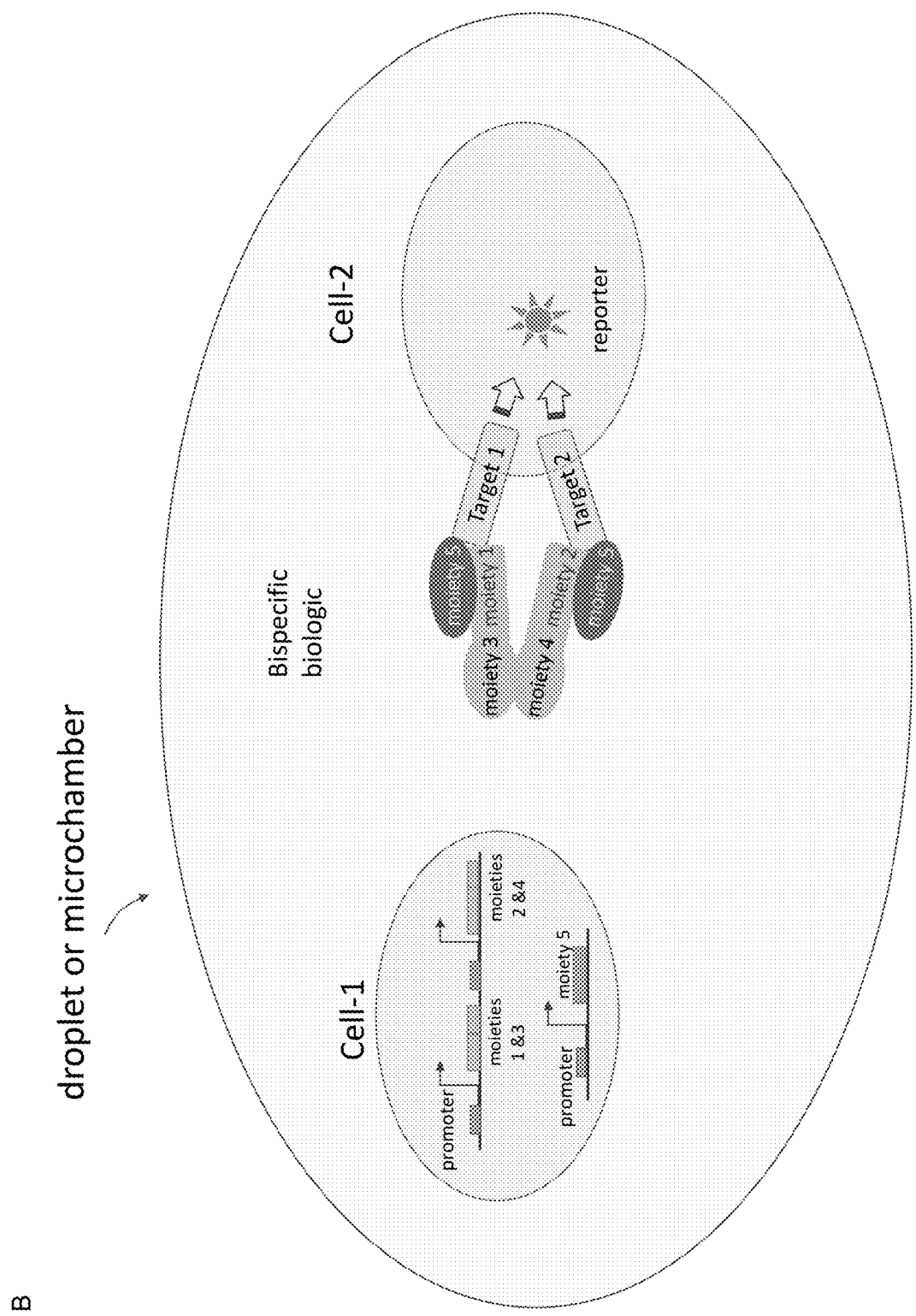

FIG. 6, (A) depicts general concepts and schemes of some embodiments of a nano-volume (droplet or microchamber) based assay for a bispecific biologic, wherein a first cell is provided, which is engineered to express five moieties of the said biologic through two integrated genomic loci, wherein a second cell is provided, which is selected or engineered to produce a reporter signal that is triggered by the said biologic, wherein the said biologic, if properly assembled and secreted in a functional form, is intended to target two distinct targets expressed on the second cell, wherein a third cell is also provided to elicit or promote the biologic function, or to serve as another reporter cell with a distinct reporter from the second one.

FIG. 6, (B) depicts general concepts and schemes of some embodiments of a nano-volume (droplet or microchamber) based assay for a bispecific biologic, wherein a first cell is provided, which is engineered to express five moieties of the said biologic through two integrated genomic loci, wherein the said moieties constitutes three single-fusion-protein subunits of the biologic, wherein a second cell is provided, which is selected or engineered to produce a reporter signal that is triggered by the said biologic, wherein the said biologic, if properly assembled and secreted in a functional form, is intended to target two distinct targets expressed on the second cell.

Figure 7:
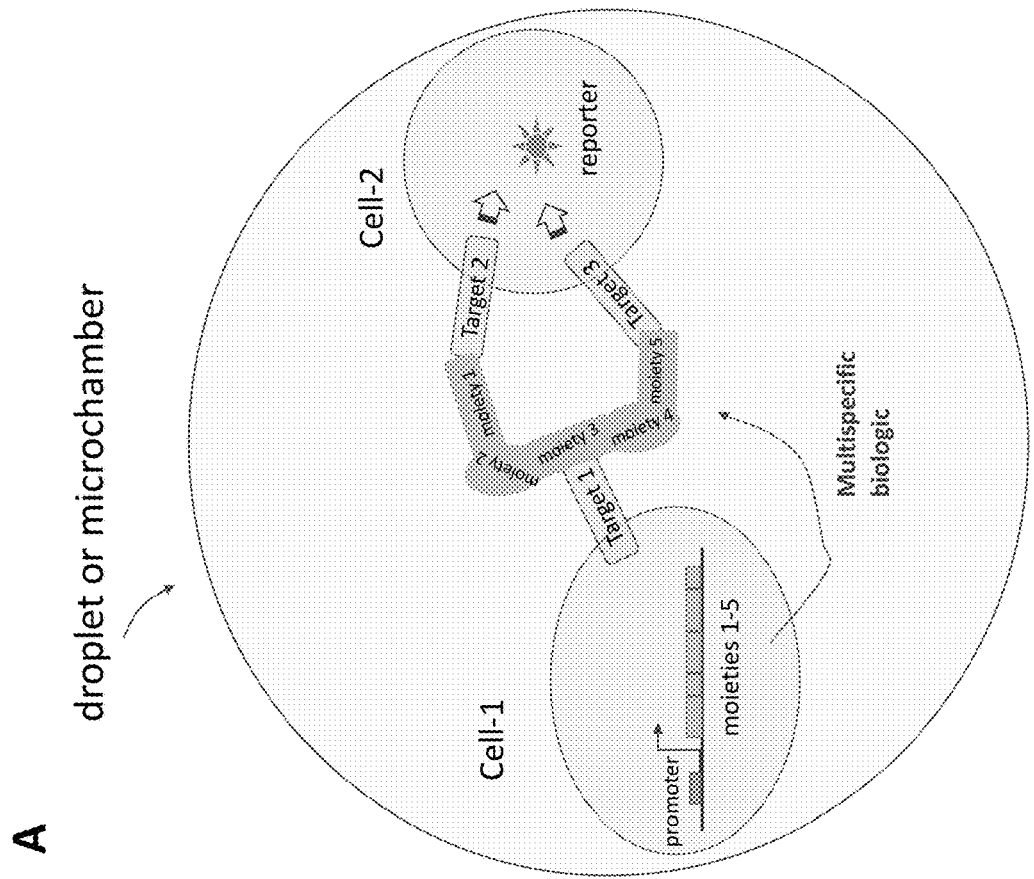
FIGS. 7, (A) and (B) are schematics showing a general principles and features of some embodiments of a compartmentalized nano-volume based assay for a triple-targeting multispecific biologic.

FIG. 7, (A) illustrates general concepts and schemes of some embodiments of a nano-volume (droplet or microchamber) based assay for a tri-specific biologic as a single chimeric protein, wherein a first cell is provided, which is engineered to express five moieties of the said biologic through a single expression cassette integrated in a genomic locus, wherein a second cell is provided, which is selected or engineered to produce a reporter signal that is triggered by the said biologic, wherein the said biologic, if properly assembled and secreted in a functional form, is intended to target three distinct assumed targets expressed on the surface of the said first and second cells respectively. FIG. 7, (B) illustrates similar assay principles and features as FIG. 7, (A), except that all the three distinct types of target molecules are mainly or exclusively expressed on the second cell (i.e., reporter cell).

Figure 8:
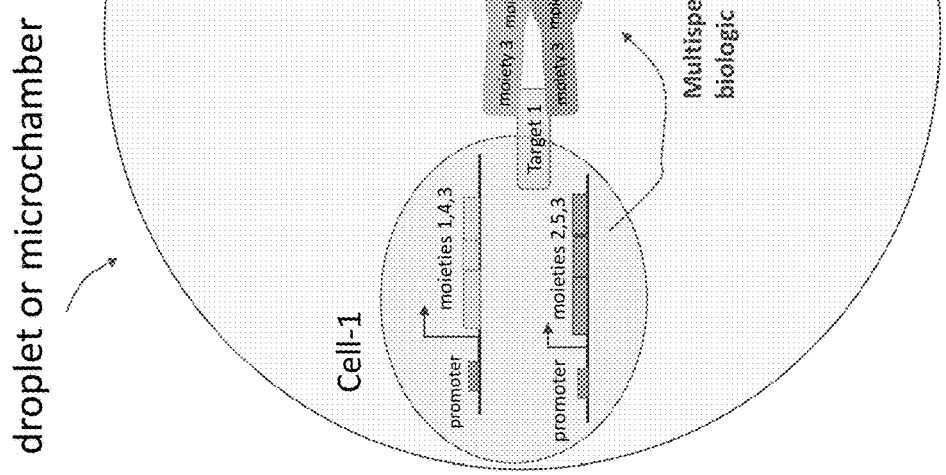
FIGS. 8, (A) and (B) depict general principles and features of some embodiments of a compartmentalized nano-volume based assay for a triple-targeting multispecific biologic.
Figure 8:
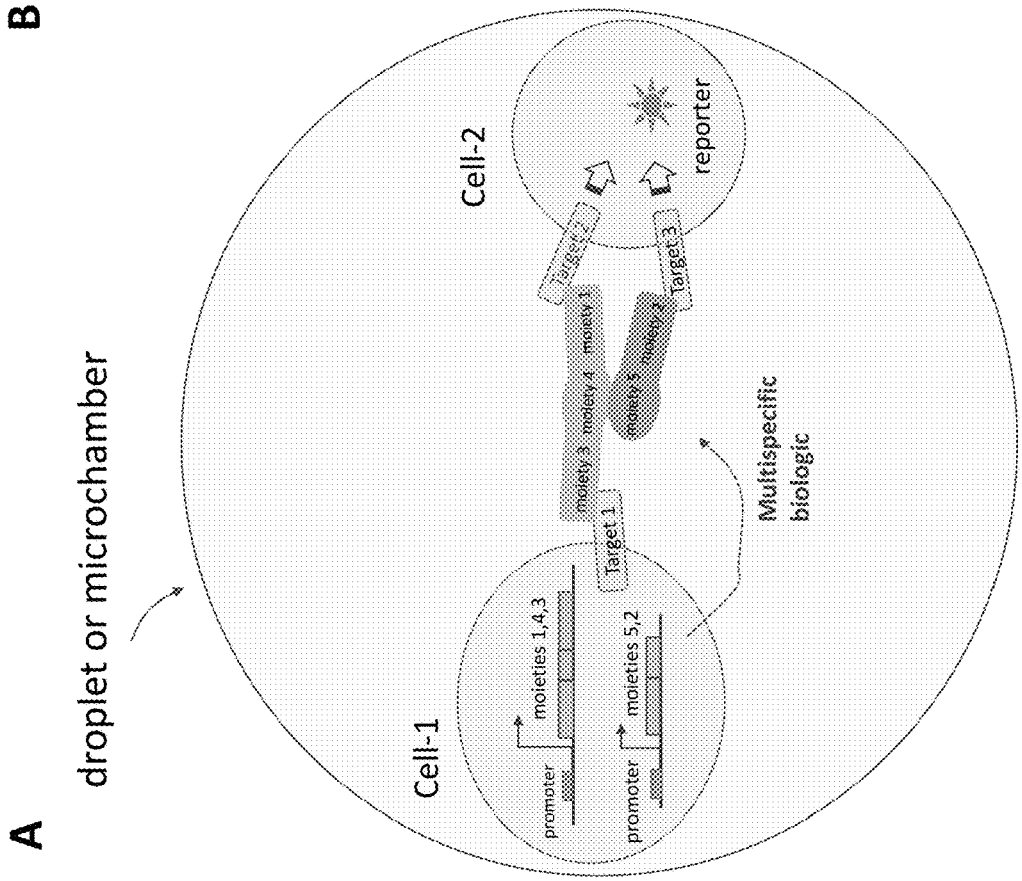

FIG. 8, (A) depicts general concepts and schemes of some embodiments of a nano-volume (droplet or microchamber) based assay for a tri-specific biologic, wherein a first cell is provided, which is engineered to express five moieties of the said biologic spreading into two asymmetric heterodimerized-subunits that are expressed from two expression cassettes integrated into two distinct genomic loci respectively, wherein a second cell is provided, which is selected or engineered to produce a reporter signal that is triggered by the said biologic, wherein the said biologic, if properly assembled and secreted in a functional form, is intended to target three distinct assumed target types expressed on the surface of the said first and second cells. FIG. 8, (B) illustrates similar assay principles and features as FIG. 8, (A), except that the tri-specific biologic comprises two heterodimerized-subunits that share an identical moiety-3, wherein the two moiety-3 copies are both involved in the binding with target-1 expressed on the first cell.

NON-LIMITING AND ILLUSTRATIVE EXAMPLES

Figure 9:
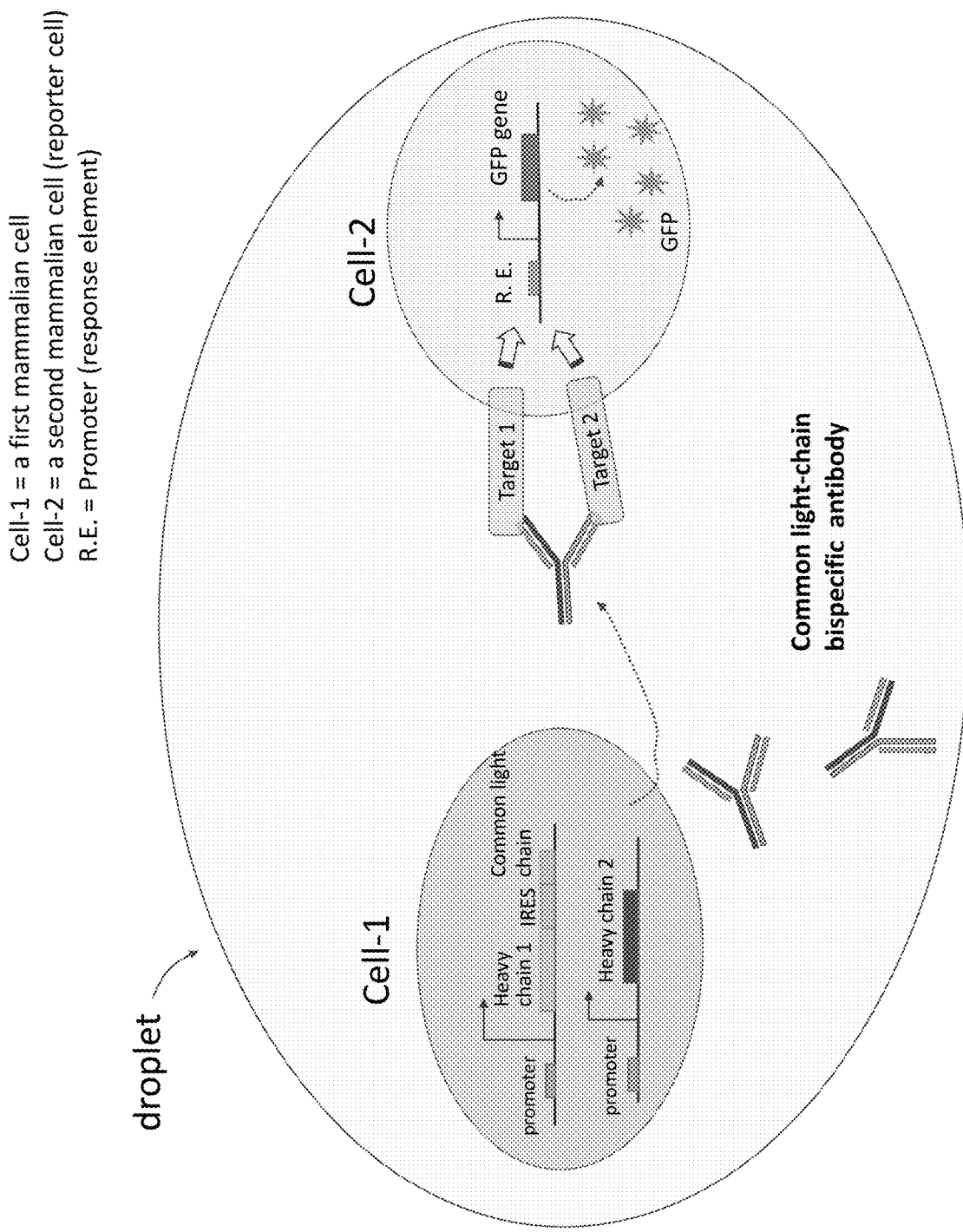
FIG. 9 depicts a non-limiting example of a droplet-based assay for the screening of a functional common-light-chain bispecific antibody (BsAb).

Example 1: Screening for a Common-Light-Chain Bispecific Antibody that Binds to Two Distinct Targets on a Single Cell FIG. 9 illustrates an embodiment of a droplet-based screening assay for a functional common-light-chain bispecific antibody from a plurality of variants, each comprising three distinct moieties (a common light chain, a first heavy light chain and a second heavy chain) that are expressed from two genomically integrated expression cassettes in a single mammalian cell (cell-1), wherein the common light chain and the first heavy chain are encoded by a single expression cassette with two open reading frames connected by an IRES element. Upon expression, proper assembly and secretion into the extracellular space, a functional bispecific antibody binds to the two cell surface targets on a reporter cell leading to transcription activation of a reporter gene (GFP). Accumulated GFP signal is optically detected by a laser and PMT-based detection module. The GFP-positive droplets can then be sorted by a droplet sorting module, and further subject to cell lysis, RT-PCR and genetic identification of individual variants that each encode a functional assembly of the said bispecific antibody.

As another example similar to that described in FIG. 9, it would be appreciated that a different format of BsAb, for example, a single fusion protein with two distinct target-binding scFvs can be used here to replace the foregoing common-light-chain BsAb format.

Figure 10:
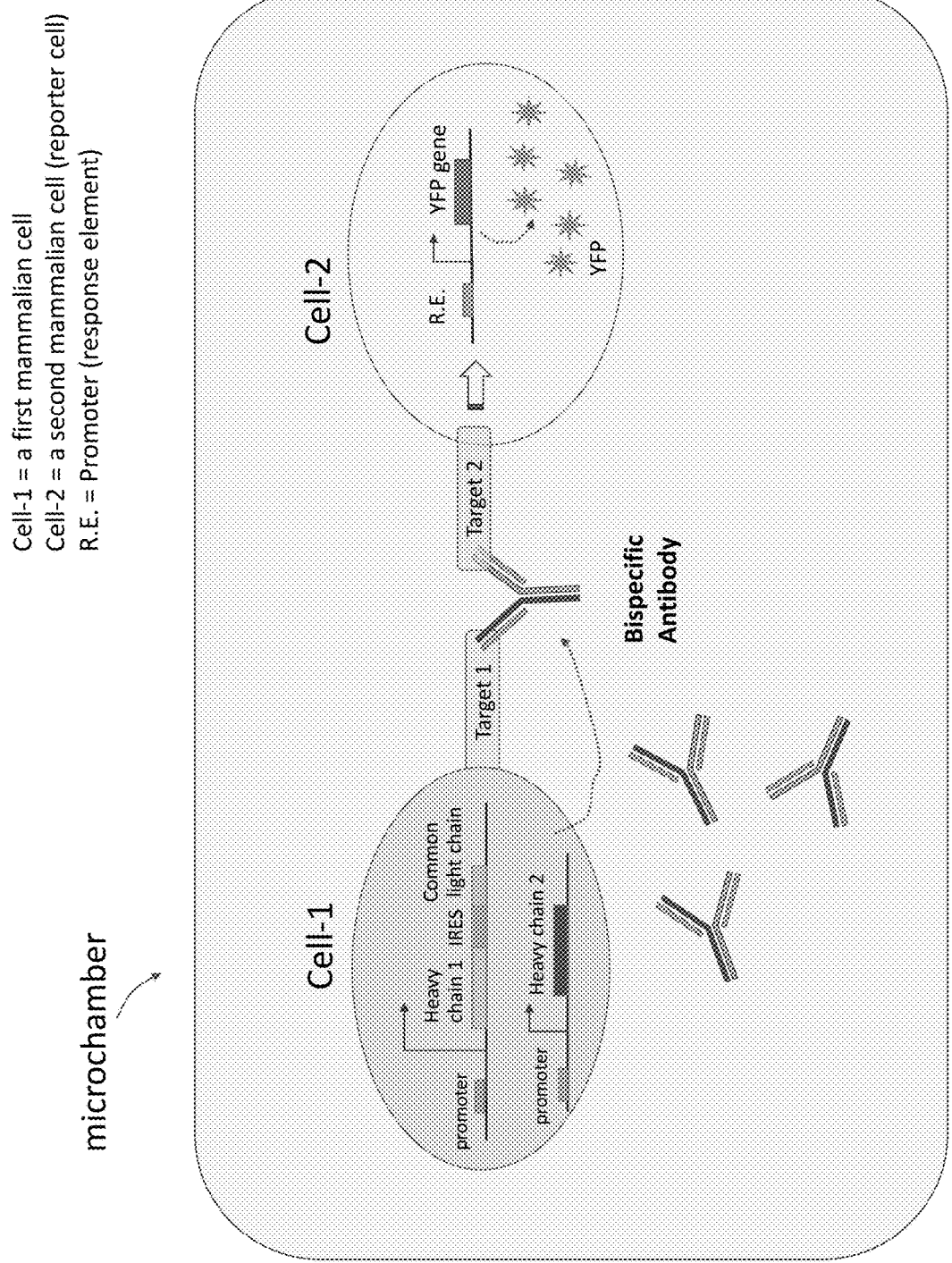
FIG. 10 depicts a non-limiting example of a microchamber-based assay screening for a common-light-chain BsAb.

Example 2: Screening for a Common-Light-Chain Bispecific Antibody that Engages Two Neighboring Cells FIG. 10 depicts an embodiment of a microchamber-based screening assay for a functional common-light-chain bispecific antibody from a plurality of variants, each comprising three distinct moieties (a common light chain, a first heavy chain and a second heavy chain) that are expressed from two genomically integrated expression cassettes in a single mammalian cell (cell-1). Upon expression, proper assembly and secretion into the extracellular space, a functional bispecific antibody binds to one cell-surface target on cell-1 and the other cell-surface target on cell-2 (a reporter cell), leading to transcription activation of a reporter gene (RFP). Accumulated RFP signal is optically detected under a fluorescent microscope. A cell-1 within RFP-positive microchambers can then be respectively recovered by a microscopy-guided micropipette, and further subject to cell lysis, RT-PCR and genetic identification of individual variants that each encode a functional assembly of the said bispecific antibody.

Example 3: Screening for a Functional Chimeric scFv Fusion Protein that Engages Two Neighboring Cells FIG. 11, (A) shows an embodiment of a droplet-based screening assay for functional chimeric scFv fusion proteins from a plurality of genetic variants, each encoding a single fusion protein comprising three distinct moieties (a first scFv intended for target-1, a second scFv intended for target-2 and a short peptide linker that links the two scFVs) that are expressed from a single genomically integrated expression cassette in a mammalian cell (cell-1). Upon expression, proper assembly and secretion into the extracellular space, a functional scFv fusion protein binds to one cell-surface target on cell-1 and the other cell-surface target on cell-2 (a reporter cell), leading to transcription activation of a reporter gene (GFP). Accumulated GFP signal is optically detected by a laser and PMT-based detection module. The GFP-positive droplets can then be sorted by a droplet sorting module, and further subject to cell lysis, RT-PCR and genetic identification of individual variants that each encode a functional chimeric scFv fusion.

Figure 11:
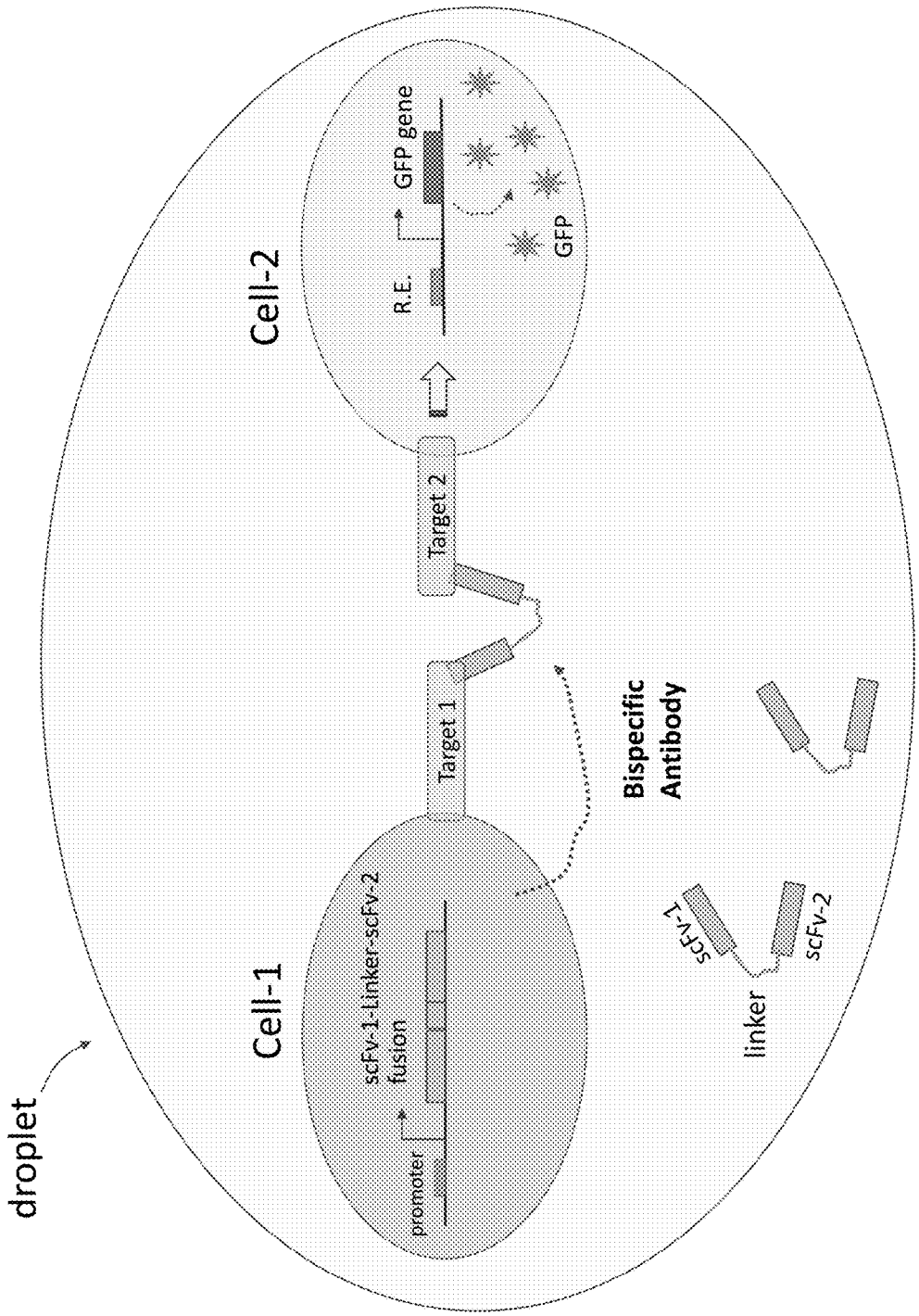
FIGS. 11, (A) and (B) depict non-limiting examples of droplet-based assays screening for a bispecific scFv fusion protein.
Figure 11:
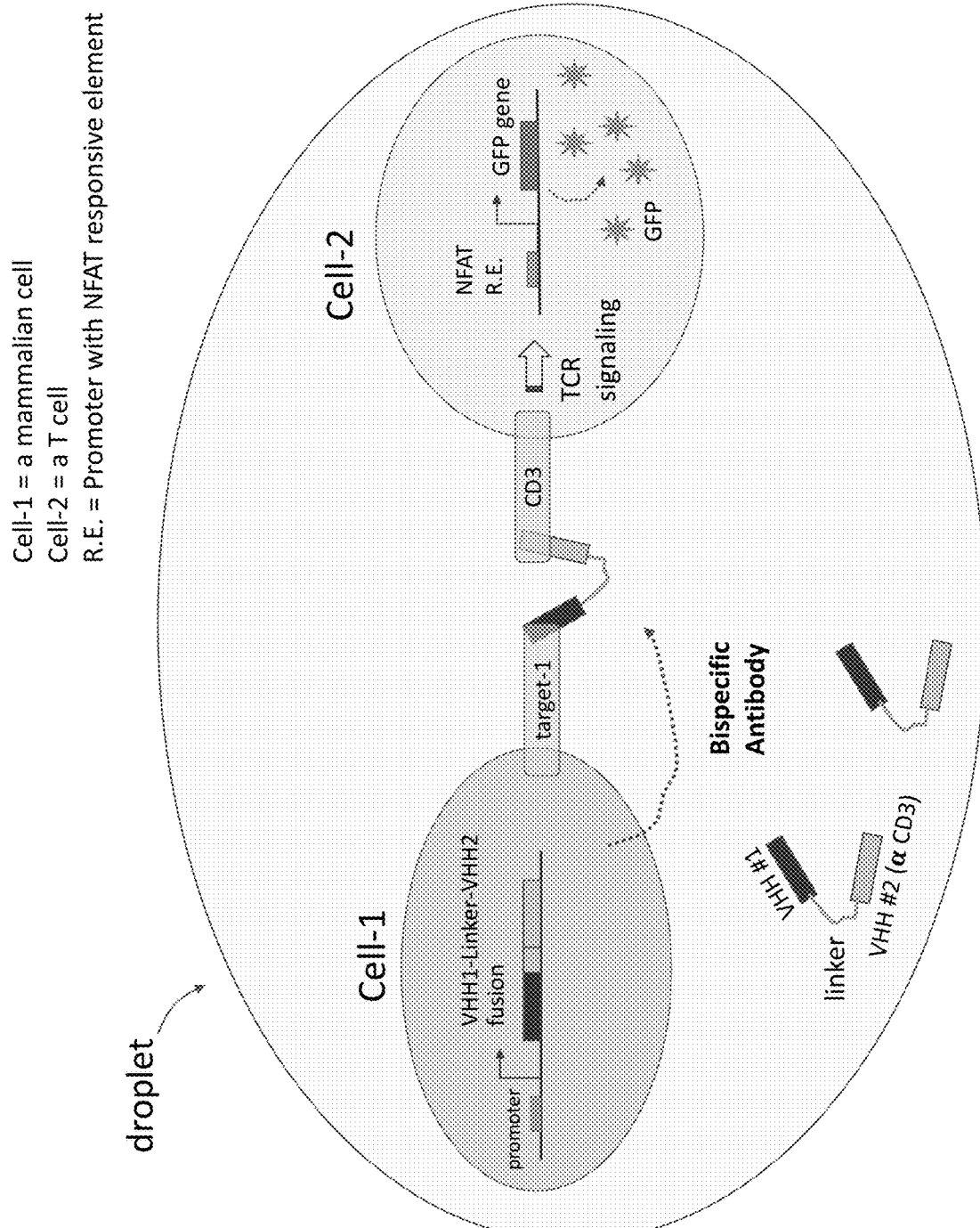

FIG. 11, (B) shows an embodiment of a droplet-based screening assay for functional bispecific chimeric VHH fusion proteins from a plurality of genetic variants, each encoding a single fusion protein comprising three distinct moieties (a first VHH intended for target-1, a second VHH intended for target-2 (CD3) and a short peptide linker that links the two VHHs) that are expressed from a single genomically integrated expression cassette in a mammalian cell (cell-1). Upon expression, proper assembly and secretion into the extracellular space, a functional bispecific VHH fusion protein binds to one cell-surface target on cell-1 and the other cell-surface target (CD3) on cell-2 (a reporter cell), leading to transcription activation of a reporter gene (GFP) under the control of a NFAT responsive element. Accumulated GFP signal is optically detected by a laser and an optical detection module. The GFP-positive droplets can then be sorted by a droplet sorting module, and further subject to cell lysis, RT-PCR and genetic identification of individual variants that each encode a functional chimeric VHH fusion.

Figure 12:
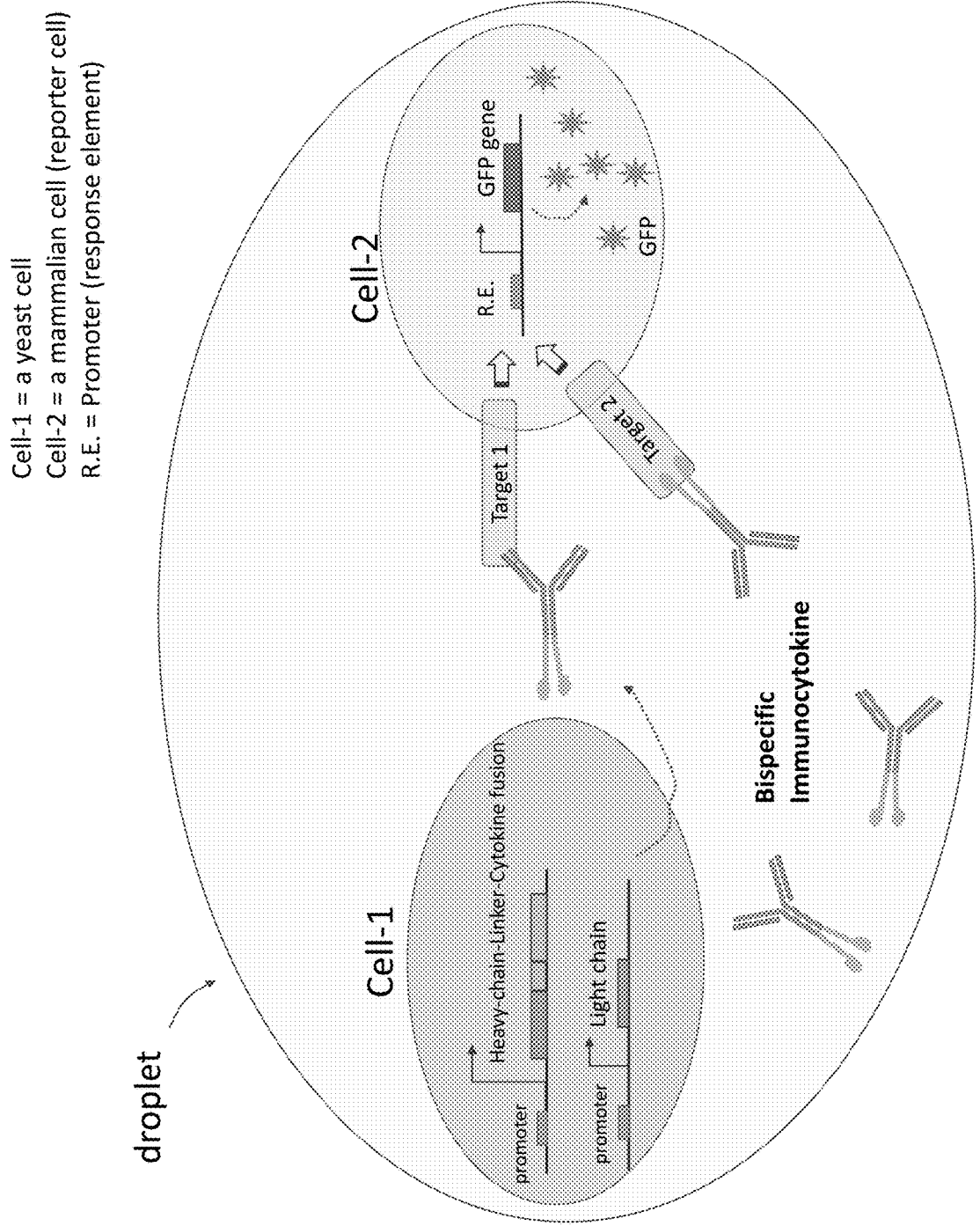
FIG. 12 depicts a non-limiting example of a droplet-based assay screening for a bispecific immunocytokine (a chimeric fusion protein of an antibody and a cytokine).

Example 4: Screening for a Bispecific Immunocytokine that Targets Two Distinct Targets on a Cell Type FIG. 12 shows an embodiment of an droplet-based screening assay for a functional bispecific immunocytokine from a plurality of variants, each comprising three distinct moieties (a light chain, a heavy chain, and a cytokine) that are expressed from two genomically integrated expression cassettes in a single mammalian cell (cell-1). Upon expression, proper assembly and secretion into the extracellular space, a functional bispecific immunocytokine binds to an antibody-target and a cytokine receptor on the cell surface of a reporter cell (cell-2), leading to transcription activation of a reporter gene (GFP). Accumulated GFP signal is optically detected by a laser and PMT-based detection module. The GFP-positive droplets can then be sorted by a droplet sorting module, and further subject to cell lysis, RT-PCR and genetic identification of individual variants that each encode a functional assembly of the said bispecific immunocytokine.

Figure 13:
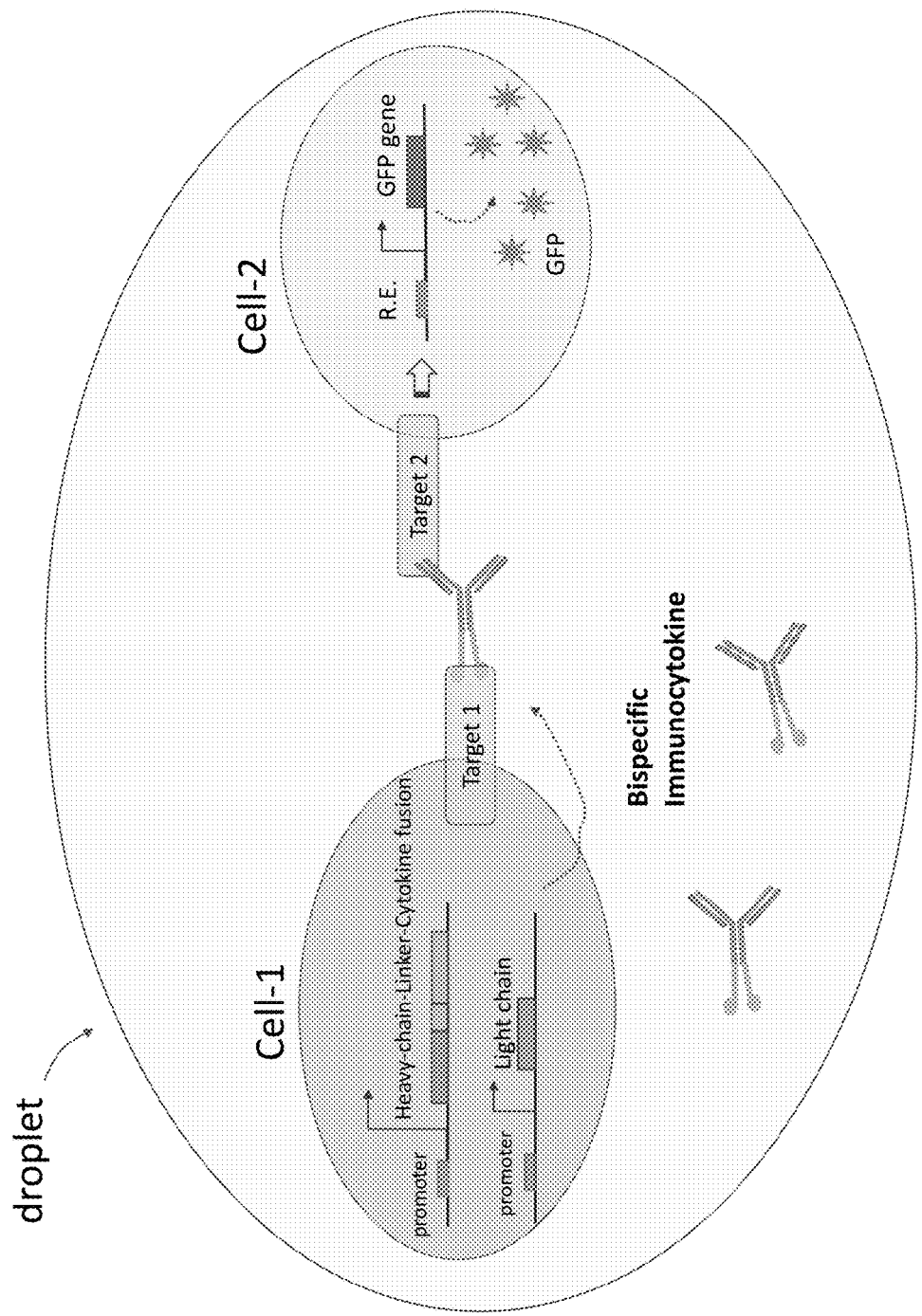
FIG. 13 depicts a non-limiting example of a compartmentalized assay screening for a bispecific immunocytokine (a chimeric fusion of an antibody and a cytokine) in droplets.

Example 5: Screening for a Bispecific Immunocytokine that Engages Two Neighboring Cells FIG. 13 depicts an embodiment of a droplet-based screening assay for a functional bispecific immunocytokine from a plurality of variants, each comprising an antibody and a cytokine assembled from three distinct moieties (a light chain, a heavy chain, and a cytokine) that are expressed from two genomically integrated expression cassettes in a single mammalian cell (cell-1). Upon expression, proper assembly and secretion into the extracellular space, a functional bispecific immunocytokine binds to an antibody-target on a reporter cell (cell-2) and a cytokine receptor on the first cell (cell-1), leading to transcription activation of a reporter gene (GFP). Accumulated GFP signal is optically detected by a laser and PMT-based detection module. The GFP-positive droplets can then be sorted by a droplet sorting module, and further subject to cell lysis, RT-PCR and genetic identification of individual variants that each encode a functional assembly of the said bispecific immunocytokine.

Example 6: Screening for a Tri-Specific Cytokine-Like Biologic that Targets Three Distinct Receptor Targets on a Single Cell Many cytokine receptors, represented by the high-affinity IL-2 receptor (which comprises CD25 (IL-2Rα), CD122 and CD132 subunits) and the IL-15 receptor (which comprises IL-15Rα, CD122 and CD132 subunits), are known as a heterotrimeric complex, where all three subunits engages a single cognate cytokine molecule. Engineering an IL-2 or IL-15 like cytokine, or a biologic with tri-specific targeting activity, may find important therapeutic applications.

Figure 14:
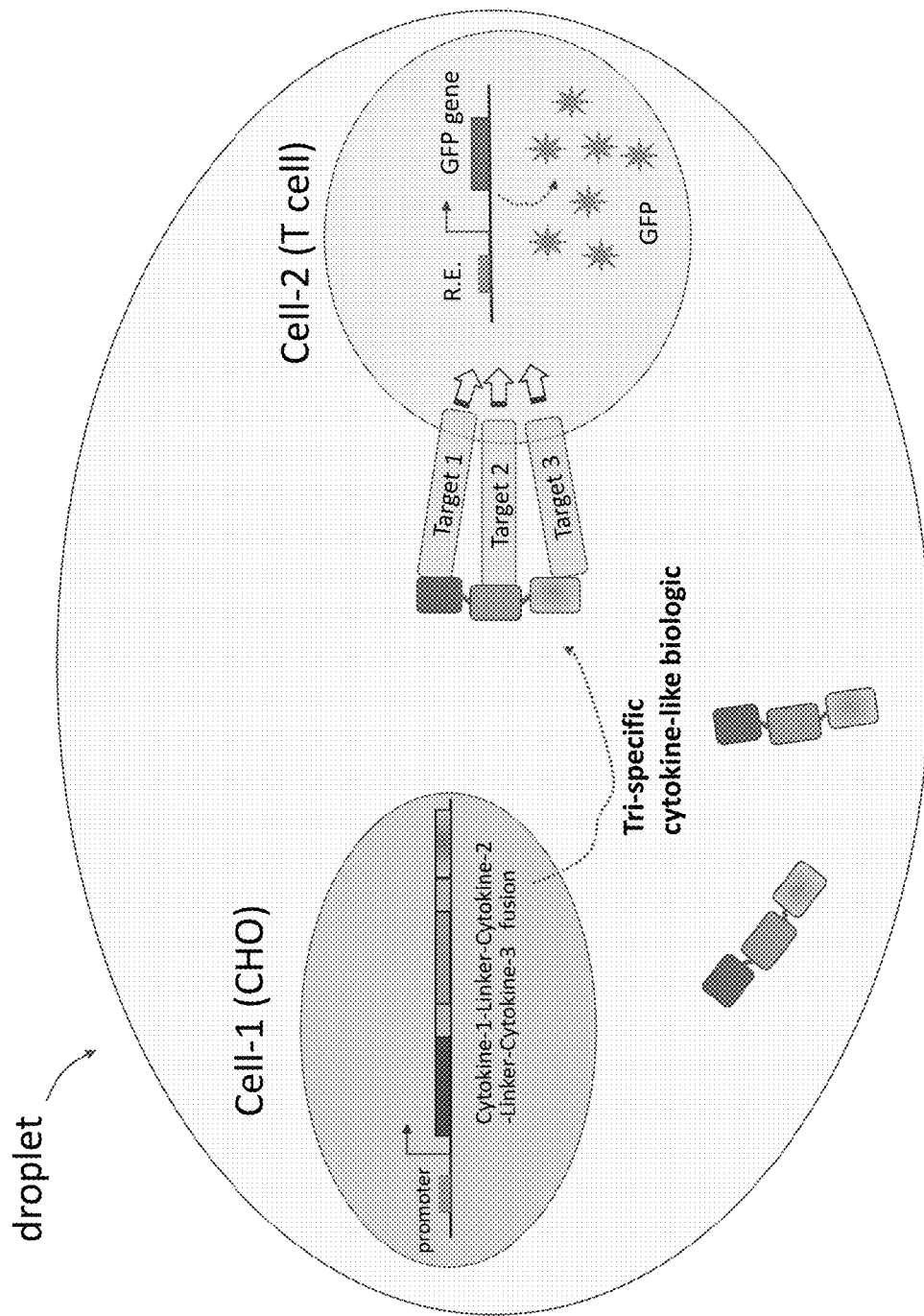
FIG. 14 depicts a non-limiting example of a compartmentalized assay screening for a tri-specific cytokine fusion (a chimeric protein of three distinct cytokines) in droplets.

As a non-limiting example (FIG. 14), a tri-specific cytokine-like fusion protein is screened using a droplet-based screening assay from a plurality of variants, each comprising three distinct target-binding moieties plus two linker peptides. A single variant of the said cytokine-like proteins is expressed from a genomically integrated expression cassette in a single mammalian cell (cell-1). Upon expression, proper assembly and secretion into the extracellular space, a functional tri-specific variant binds to three distinct receptors on the reporter cell (cell-2), leading to transcription activation of a reporter gene (GFP). Accumulated GFP signal is optically detected by a laser and PMT-based detection module. The GFP-positive droplets can then be sorted by a droplet sorting module, and further subject to cell lysis, RT-PCR and genetic identification of individual variants that each encode a functional tri-specific cytokine-like molecule.

Figure 15:
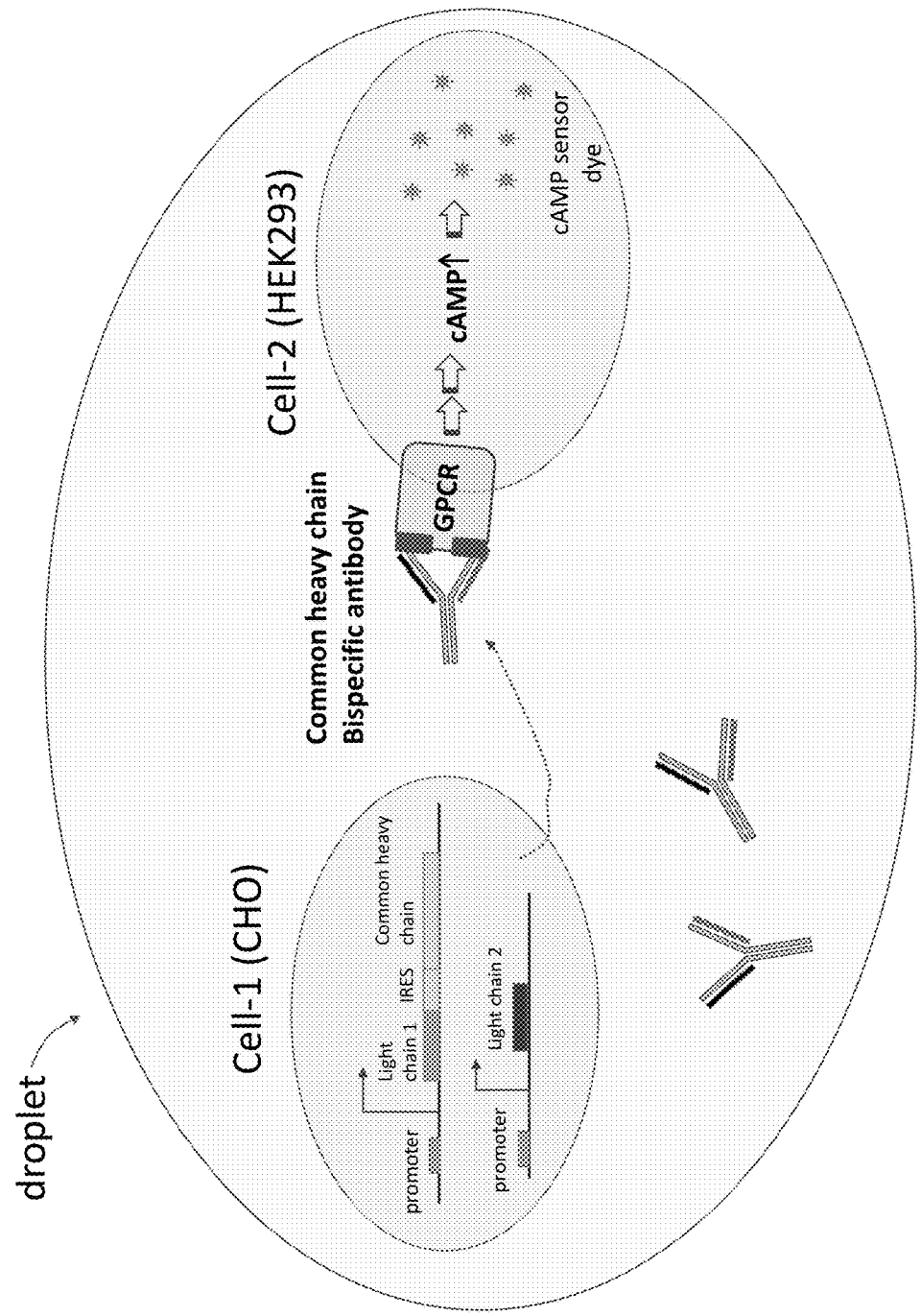
FIG. 15 depicts a non-limiting example of a droplet-based assay for screening for an agonistic common-light-chain BsAb targeting two sites on a same GPCR target on the cell surface.

Example 7: Screening for a Common-Heavy-Chain Bispecific Antibody for a GPCR Target FIG. 15 shows an embodiment of a droplet-based screening assay for a functional common-heavy-chain bispecific antibody from a plurality of variants, each comprising three distinct moieties (a common heavy chain, a first light chain and a second light chain) that are expressed from two genomically integrated expression cassettes in a single mammalian cell (cell-1). Upon expression, proper assembly and secretion into the extracellular space, a functional bispecific antibody binds to two distinct molecular sites of a single GPCR target on a reporter cell, leading to signal activation and accumulation of the downstream effector molecule cAMP (a reporter signal). Accumulated cAMP is bound to provided cAMP-specific fluorescent sensor dyes, which are subsequently detected by a laser and PMT-based detection module. The sensor-positive droplets can then be sorted by a droplet sorting module, and further subject to cell lysis, RT-PCR and genetic identification of individual variants that each encode a functional assembly of the said bispecific antibody.

Figure 16:
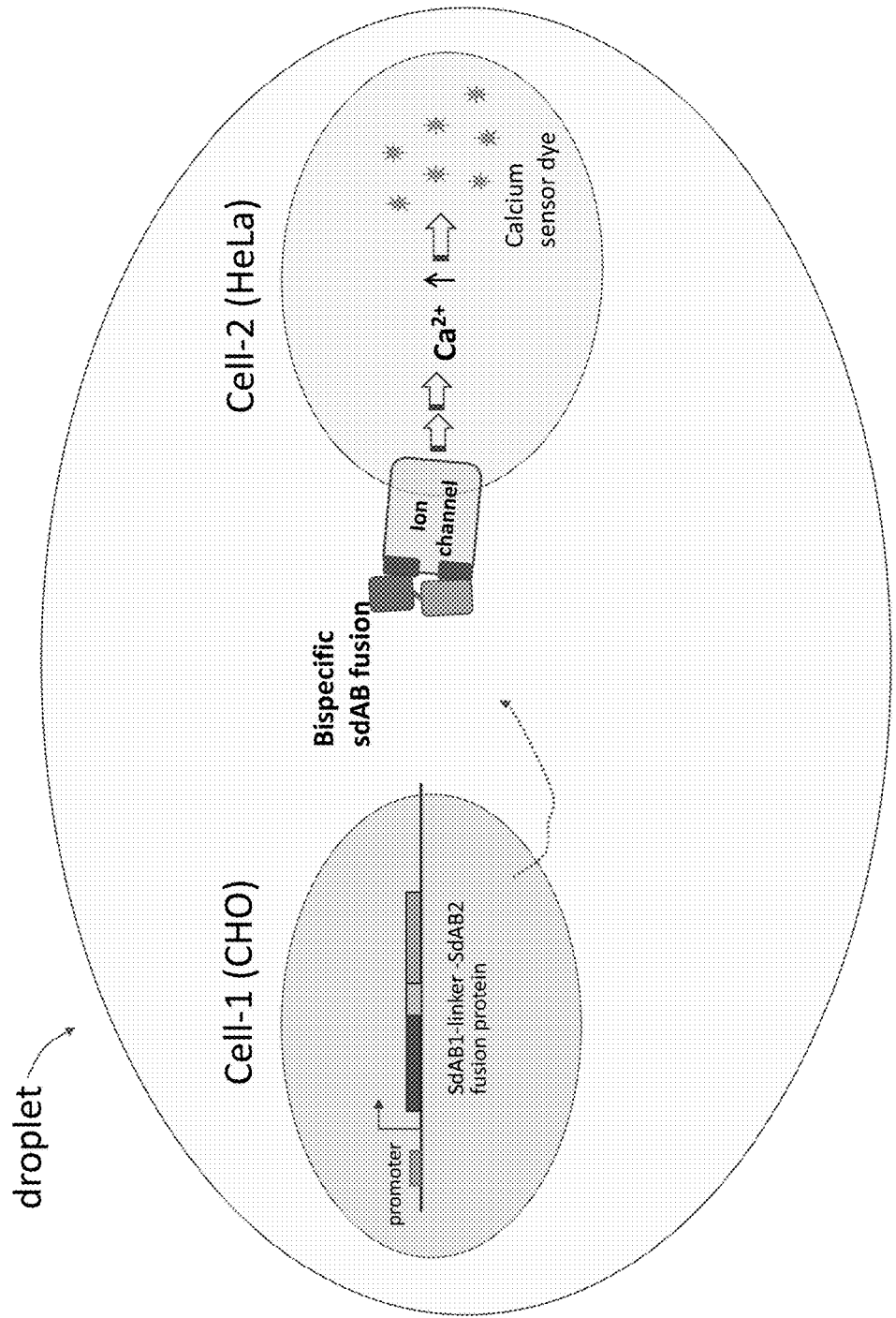
FIG. 16 depicts a non-limiting example of a droplet-based assay for screening for an agonistic common-light-chain BsAb targeting two sites on a same ion channel target on the cell surface.

Example 8: Screening for a Bispecific Single-Domain-Antibodies (sdABs) Fusion Protein that Antagonizes an Ion Channel FIG. 16 shows an example of a droplet-based screening assay for a functional bispecific sdABs fusion protein from a plurality of variants, each comprising three distinct moieties (a first sdAB, a second sdAB, and a peptide linker) that are expressed from a single genomically integrated expression cassettes in a single mammalian cell (cell-1). Upon expression, proper assembly and secretion into the extracellular space, a functional bispecific sdABs fusion protein binds to two distinct molecular sites of a single calcium channel target on a reporter cell, leading to calcium flux and accumulation in the reporter cell. Accumulated Calcium ions bind to provided fluorescent Calcium sensor dyes, which are subsequently detected by a laser and PMT-based detection module. The sensor-positive droplets can then be sorted by a droplet sorting module, and further subject to cell lysis, RT-PCR and genetic identification of individual variants that each encode a functional assembly of the said bispecific sdABs fusion protein.

Example 9: Screening for a Common-Light-Chain Bispecific Antibody that Targets Two Distinct Targets on a Cell FIG. 17, (A) shows an embodiment of a droplet-based screening assay for a functional common-light-chain bispecific antibody from a plurality of variants, each comprising three distinct moieties (a common light chain, a first heavy light chain and a second heavy chain) that are expressed from two genomically integrated expression cassettes in a single mammalian cell (cell-1). Upon expression, proper assembly and secretion into the extracellular space, a functional common-light-chain bispecific antibody binds to two distinct cell surface targets on a reporter cell, wherein the two expressed targets are engineered with an extracellular SNAP™- and CLIP™-tag respectively. The SNAP-tag covalently self-links with a provided oligo-DNA labelled with $O^6$-benzylguanin on one end and a FRET donor on the other; The CLIP-tag covalently self-links with another provided oligo-DNA labelled with $O^2$-benzylcytosine on one end and a FRET acceptor on the other. Bispecific targeting by a functional common-light-chain antibody brings the donor and acceptor within close proximity (i.e., within effective Foster radius), leading to FRET signal upon excitation by a proper laser wavelength. The FRET signal is optically detected by a PMT-based FRET-compatible detection module. The FRET-positive droplets can then be sorted by a droplet sorting module, and further subject to cell lysis, RT-PCR and genetic identification of individual variants that each encode a functional assembly of the said bispecific antibody.

Figure 17:
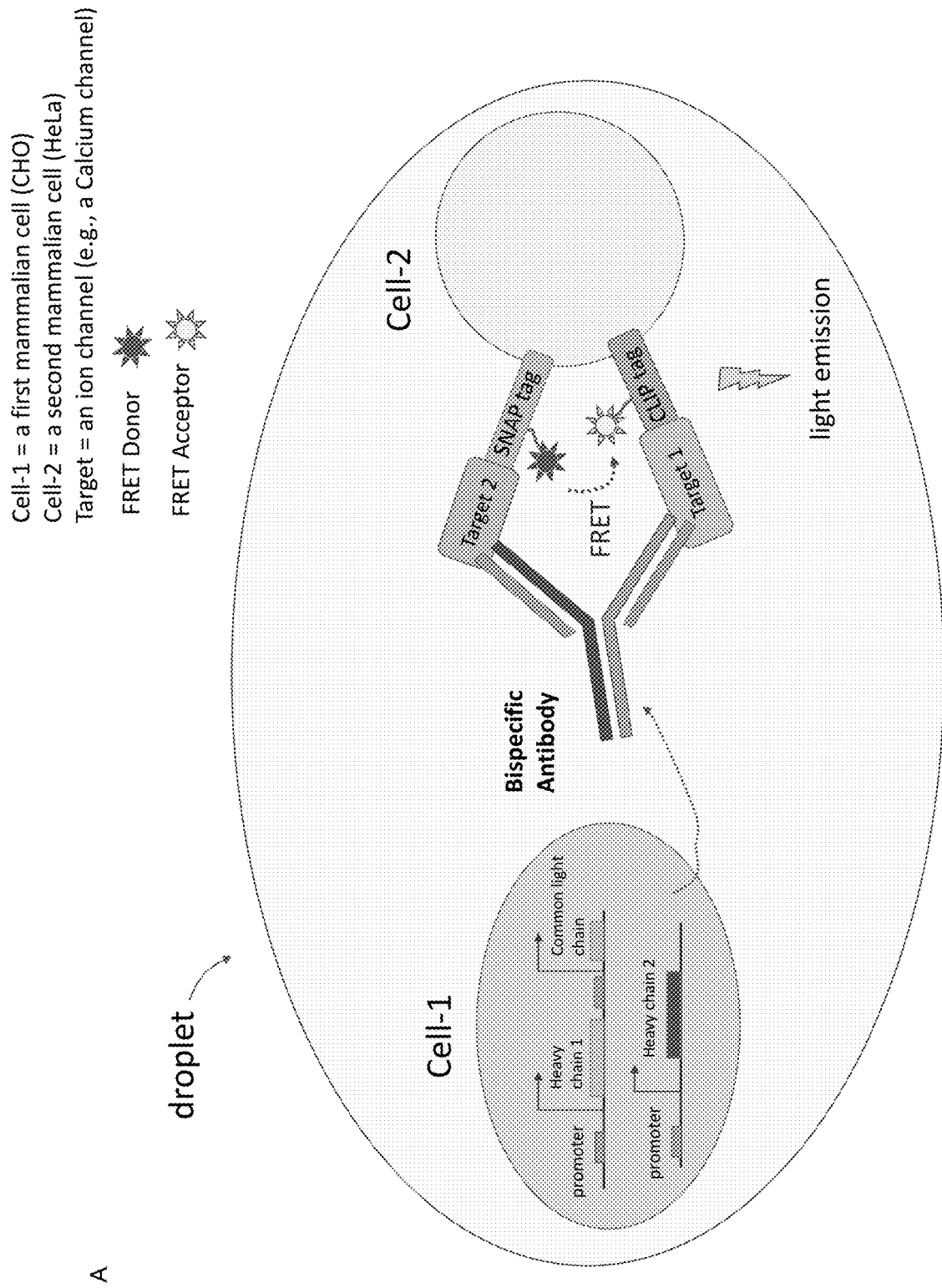
FIGS. 17, (A) and (B) depict non-limiting example of droplet-based assays screening for a common-light-chain BsAb for two distinct cell-surface targets via a FRET based reporter.
Figure 17:
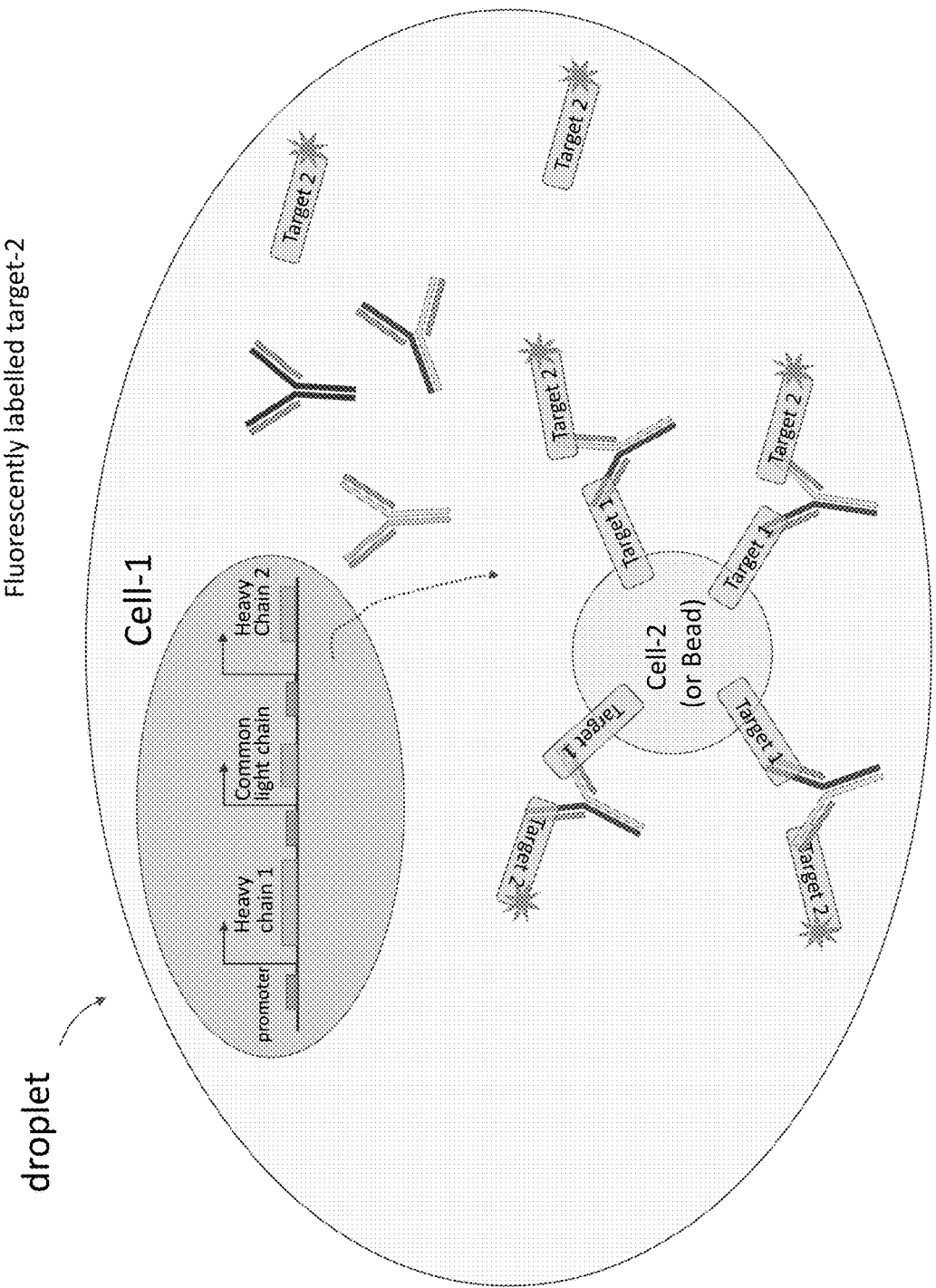

FIG. 17, (B) shows an embodiment of a droplet-based screening assay for a functional common-light-chain bispecific antibody from a plurality of variants, each comprising three distinct moieties (a common light chain, a first heavy light chain and a second heavy chain) that are expressed from one genomically integrated expression cassette in a single mammalian cell (cell-1). Upon expression, proper assembly and secretion into the extracellular space, a functional common-light-chain bispecific antibody binds to target-1 that is expressed on a cell (cell-2) or conjugated to a capture bead (or particle, or a polymeric matrix). The said common-light-chain bispecific antibody also binds to target-2 which is provided as fluorescently labelled soluble molecules in the droplet. Accumulation of the bispecific antibody/labelled-target-2 complex leads to fluorescence focus formation, which can be optically detected. The fluorescence focus-positive droplets can then be sorted by a droplet sorting module, and further subject to cell lysis, RT-PCR and genetic identification of individual variants that each encode a functional assembly of the said bispecific antibody.

Figure 18:
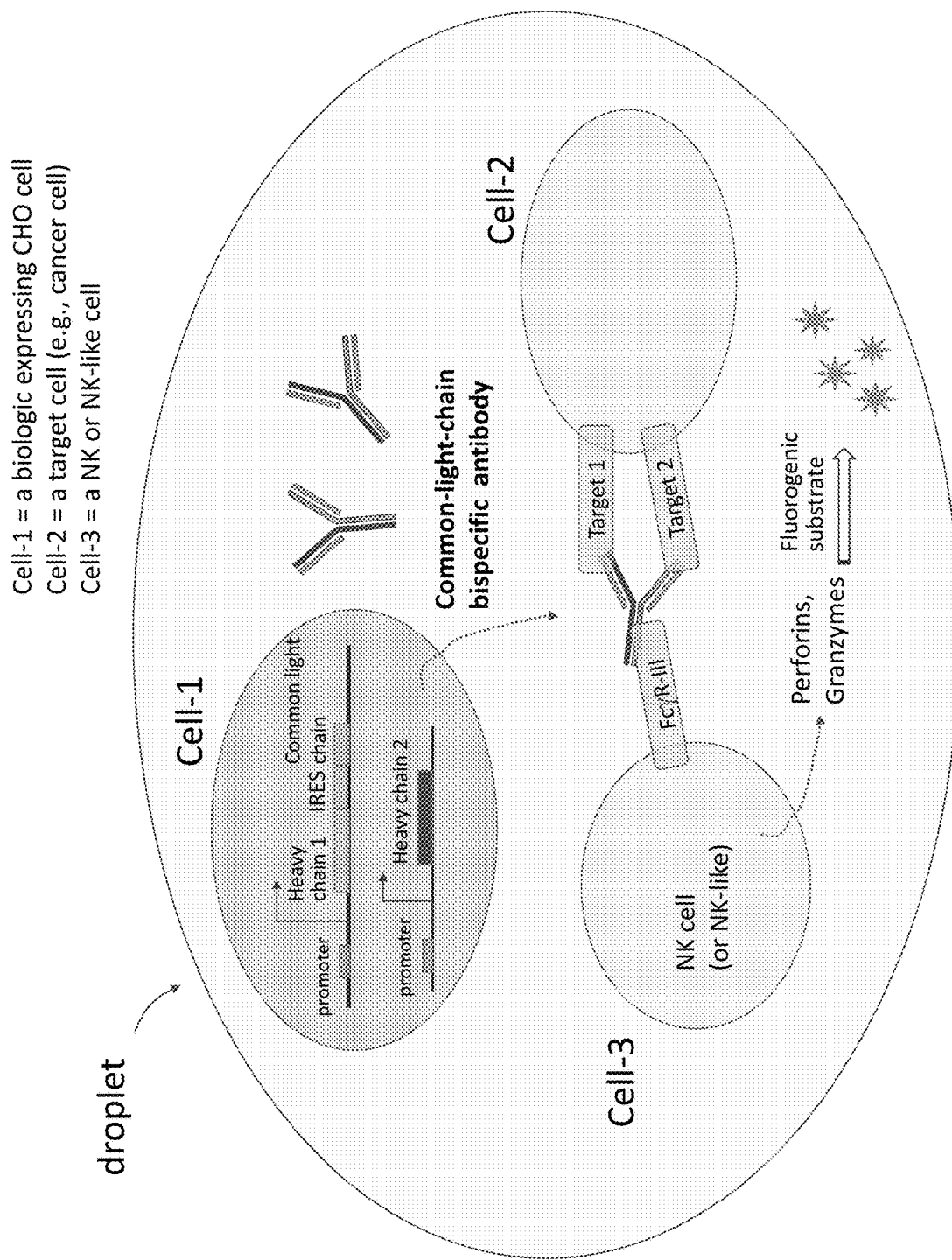
FIG. 18 depicts an example of droplet assays with three distinct types of cell to screen for a common-light-chain BsAb that targets two molecular targets on a cancer cell, based on antibody-dependent cell-mediated cytotoxicity (ADCC).

Example 10: Screening for a Common-Light-Chain Bispecific Antibody with a Proper ADCC Activity FIG. 18 shows an embodiment of a droplet-based screening assay for a functional common-light-chain BsAb from a plurality of variants, each comprising three distinct subunits (a common light chain, a first heavy light chain and a second heavy chain) that are expressed from two genomically integrated expression cassettes in a single mammalian cell (cell-1). Upon expression, proper assembly and secretion into the extracellular space, a functional bispecific antibody binds to the two cell surface targets on a second cell (a cancer cell), and meanwhile, the Fc region of the BsAb is bound to the FcγR-III receptors a provided third cell (a NK or NK-like cell), leading to the activation of the third cell and subsequent release of ADCC-related effectors (e.g., Perforins and Granzymes). With provided fluorogenic substrates, the accumulated effectors are then detected by an optical detector such as a PMT or CCD. The fluorescence-positive droplets can then be sorted by a droplet sorting module, and further subject to cell lysis, RT-PCR and genetic identification of individual variants that each encode a functional assembly of the said bispecific antibody.

Figure 19:
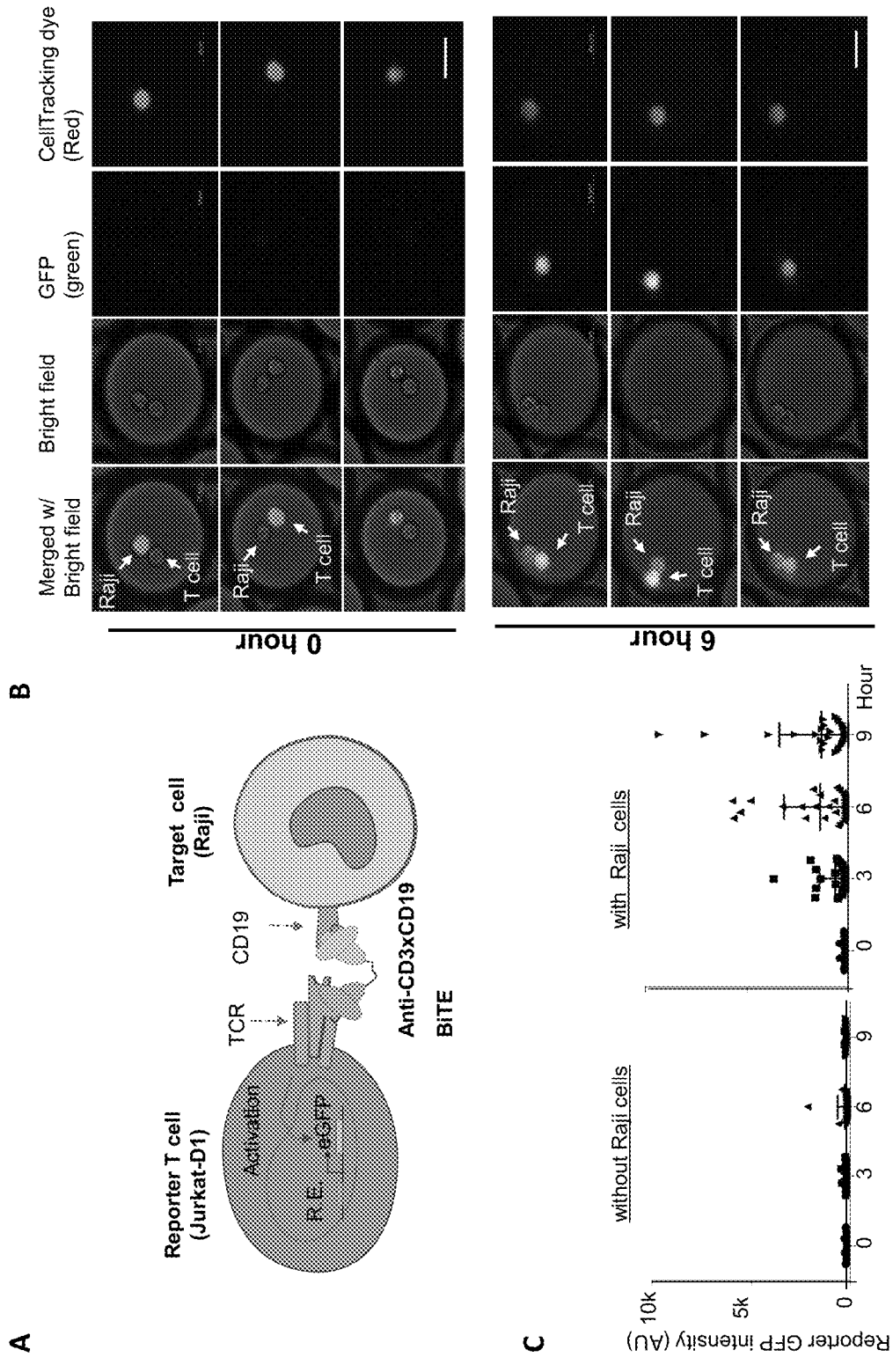
FIG. 19, (A) depicts an example of droplet assays illustrating the mechanism-of-action of a BiTE (an anti-CD3× CD19 BiTE) on a target cell (a first cell) and a T cell (a second cell); (B) cell images; and (C) Reporter GFP intensity (±Raji cells).

Example 11: Functional Assay for an Anti-CD3×CD19 Bispecific T Cell Engager (BiTE) in Droplets FIG. 19, (A) illustrates the mechanism-of-action of a BiTE (e.g. an anti-CD3×CD19 BiTE), R.E., promoter responsive element; (B) Microscopic images of nonactivated (at 0 hour) and activated (at 6 hour) Jurkat-D1 reporter T cells in the presence of Raji cell (a CD19$^+$ lymphoma cell line) and a recombinant anti-CD3×CD19 BiTE in droplets; scale bar, 100 μm. Green, GFP reporter signal; Red, a CellTracking dye pre-labelled for Raji; (C) Kinetic GFP signal intensity change in Jurkat-D1 cells added with 10 ng/ml of the said anti-CD3×CD19 BiTE, with or without the presence of Raji cells, over a 9-hour time period post co-encapsulation in droplets.

Non-Limiting and Illustrative Processes

Figure 20:
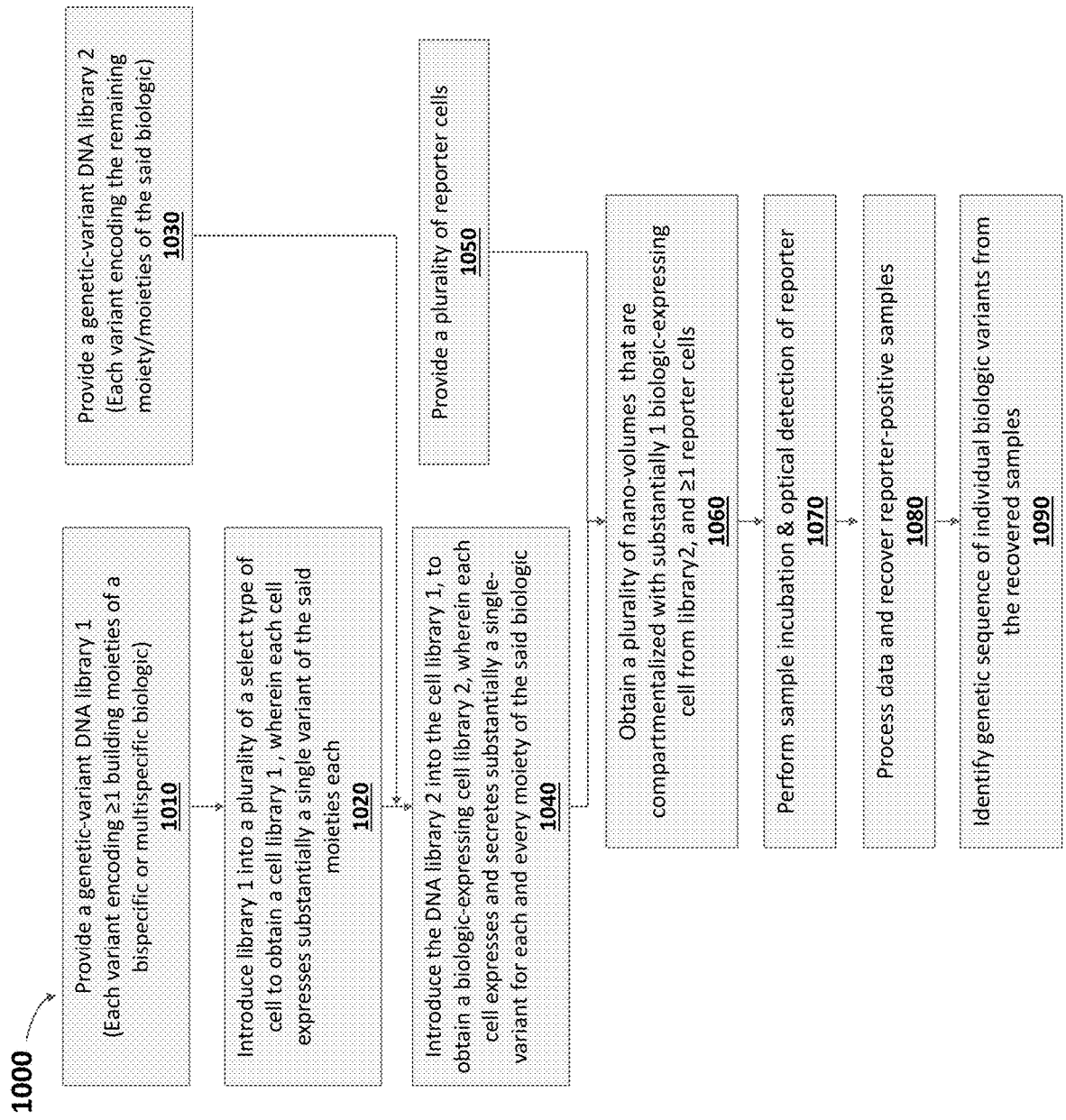
FIG. 20 is a diagram illustrating a non-limiting workflow and process for performing an assay for a functional bispecific or multispecific biologic in a compartmentalized nano-volume.

FIG. 20 illustrates an example process 1000 in accordance with an implementation of the present disclosure. Process 1000 may represent an aspect of implementing the proposed concepts and schemes such as one or more of the various schemes, concepts and examples described above with respect to FIG. 1-FIG. 18. More specifically, process 1000 may represent an aspect of the proposed concepts and schemes pertaining to compartmentalized nano-volume based assays to directly and rapidly screen for functional single variants from an engineered library of bispecific or multispecific biologics in an ultra-high throughput manner. Process 1000 may include one or more operations, actions, or functions as illustrated by one or more of blocks 1010, 1020, 1030, 1040, 1050, 1060, 1070, 1080 and 1090. Although illustrated as discrete blocks, various blocks of process 1000 may be divided into additional blocks, combined into fewer blocks, or eliminated, depending on the desired implementation. Moreover, the blocks of process 1000 may be executed in the order shown in FIG. 20 or alternatively in a different order. Furthermore, the blocks of process 1000 may be executed iteratively. Process 1000 may begin at block 1010.

At 1010, process 1000 may involve providing a genetic-variant DNA library 1, wherein each variant encodes in a single expression-construct at least one moieties comprised by a bispecific or multispecific biologic. Process 1000 may proceed from 1010 to 1020.

At 1020, process 1000 may involve introducing library 1 into a single genomic locus of a plurality of a select type of cell to obtain an engineered cell library 1, wherein each individual cell expresses substantially a single variant of the said moieties encoded by the said genetic-variant library 1. Process 1000 may proceed from 1020 to 1040.

At 1030, which may be performed in parallel with 1010 and 1020, process 1000 may involve providing a genetic-variant DNA library 2, wherein each variant encodes in a single expression-construct the remaining moieties that are not encoded by the genetic-variant DNA Library 1, but otherwise comprised by a bispecific or multispecific biologic. Process 1000 may proceed from 1030 to 1040.

At 1040, process 1000 may involve Introducing the DNA library 2 into the cell library 1 engineered at 1020, to obtain a biologic-expressing cell library 2, wherein each cell expresses and secretes substantially a single-variant for each and every moiety of an integral biologic. Process 1000 may proceed from 1040 to 1060.

At 1050, which may be performed in parallel with 1040, process 1000 may involve providing a plurality of a reporter cell. Process 1000 may proceed from 1050 to 1060.

At 1060, process 1000 may involve obtaining a plurality of nano-volumes (droplets or microchambers) that are compartmentalized with substantially 1 biologic-expressing cell from engineered cell library 2, and reporter cells provided at 1050. Process 1000 may proceed from 1060 to 1070.

At 1070, process 1000 may involve performing sample incubation and optical detection of reporter signals. Process 1000 may proceed from 1070 to 1080.

At 1080, process 1000 may involve processing signal detection data and recovering reporter-positive cell samples. Process 1000 may proceed from 1080 to 1090.

At 1090, process 1000 may involve identifying genetic sequence of individual biologic variants from the recovered samples.

Figure 21:
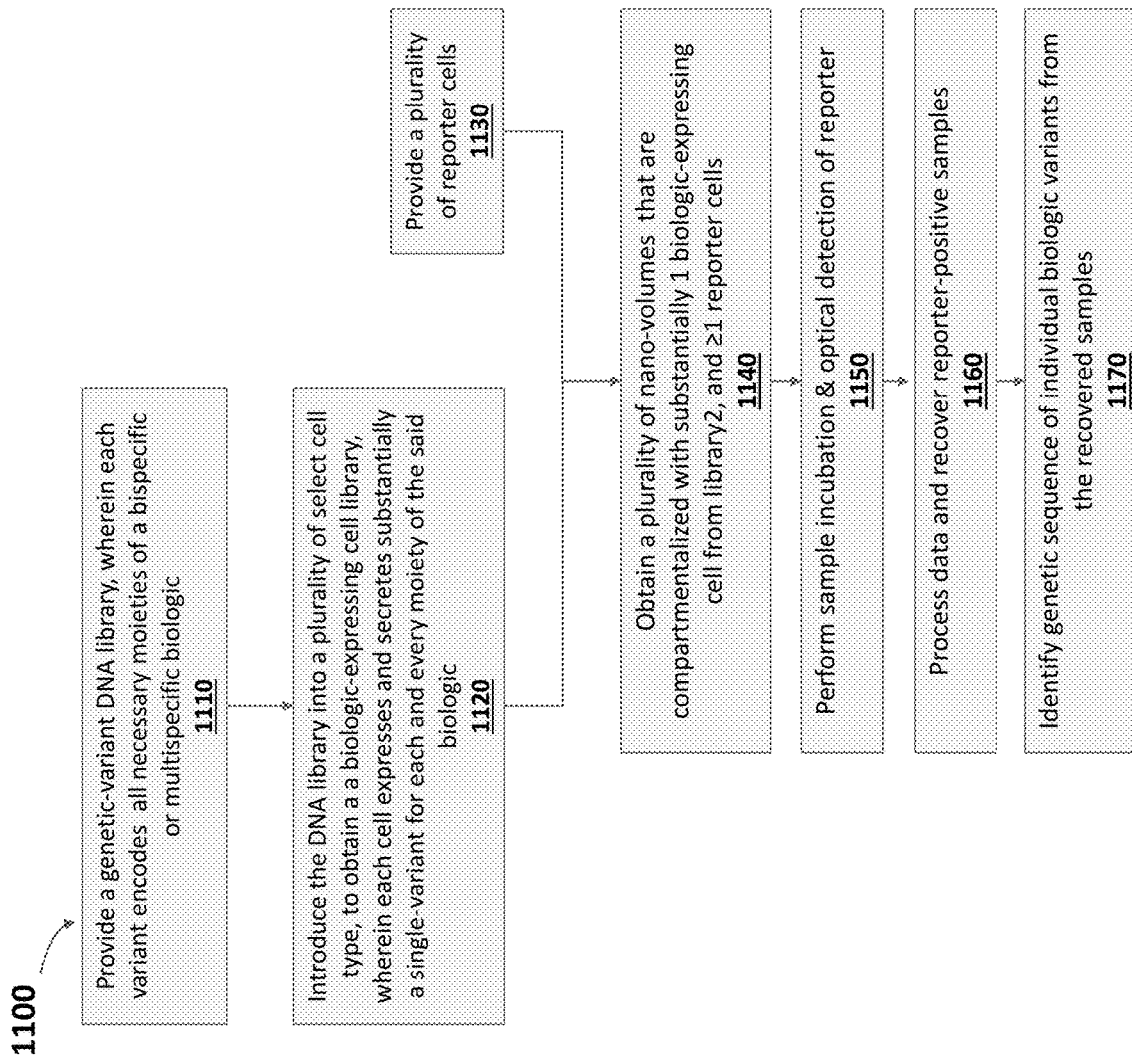
FIG. 21 is a diagram illustrating a non-limiting example of a workflow and process for performing an assay for a functional bispecific or multispecific biologic in a compartmentalized nano-volume.

FIG. 21 illustrates an example process 1100 in accordance with an implementation of the present disclosure. Process 1100 may represent an aspect of implementing the proposed concepts and schemes such as one or more of the various schemes, concepts and examples described above with respect to FIG. 1~FIG. 19. More specifically, process 1100 may represent an aspect of the proposed concepts and schemes pertaining to compartmentalized nano-volume based assays to directly and rapidly screen for functional single variants from an engineered library of bispecific or multispecific biologics in an ultra-high throughput manner. Process 1100 may include one or more operations, actions, or functions as illustrated by one or more of blocks 1110, 1120, 1130, 1140, 1150, 1160 and 1170. Although illustrated as discrete blocks, various blocks of process 1100 may be divided into additional blocks, combined into fewer blocks, or eliminated, depending on the desired implementation. Moreover, the blocks of process 1100 may be executed in the order shown in FIG. 21 or alternatively in a different order. Furthermore, the blocks of process 1100 may be executed iteratively. Process 1100 may begin at block 1110.

At 1110, process 1100 may involve providing a genetic-variant DNA library, wherein each variant encodes all necessary moieties of a bispecific or multispecific biologic. Process 1100 may proceed from 1110 to 1120.

At 1120, process 1100 may involve introducing the DNA library from 1110 into a plurality of a select cell type, to obtain an engineered biologic-expressing cell library, wherein each cell expresses and secretes substantially a single-variant for each and every moiety of the said biologic.

Figure 22:
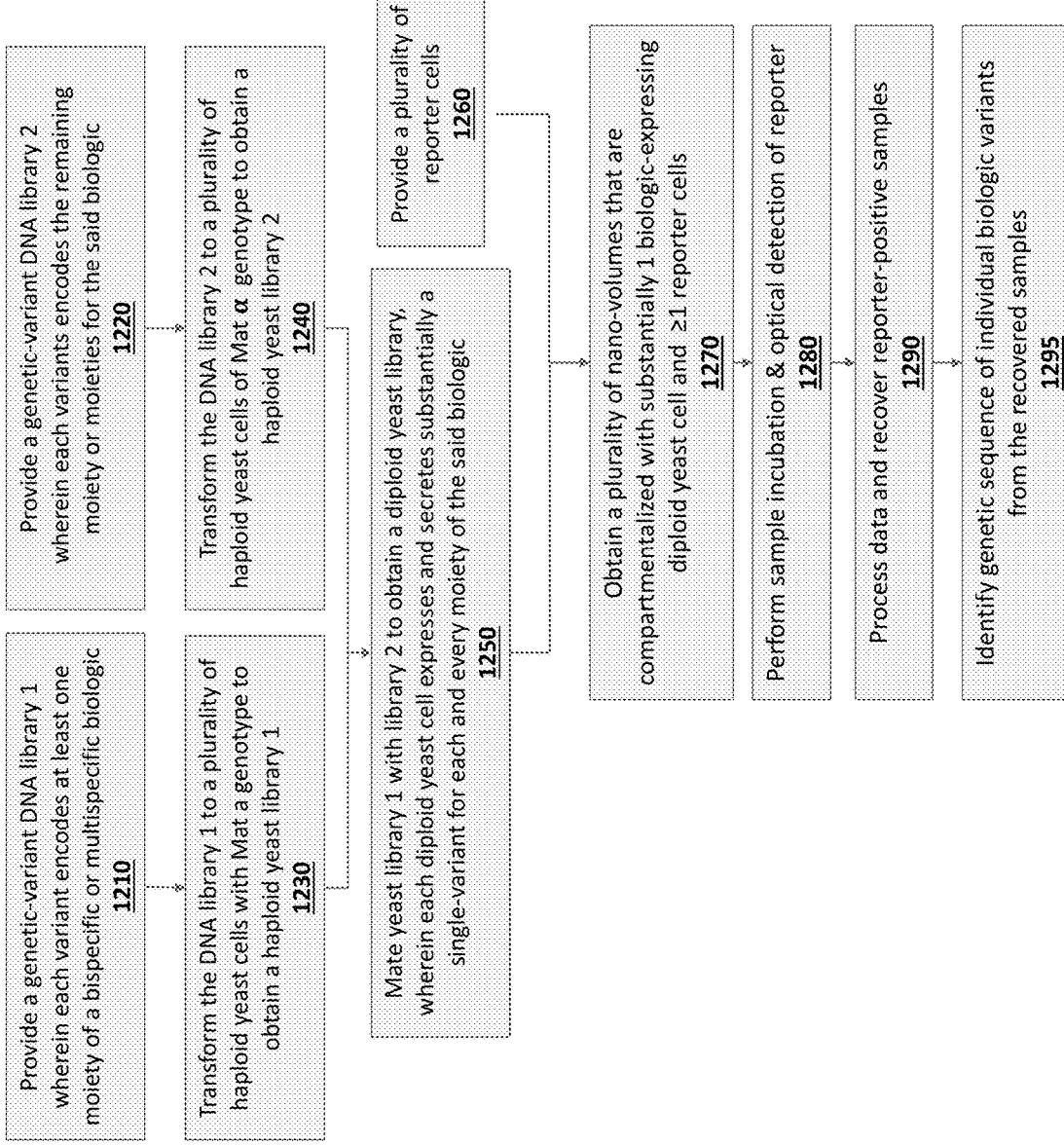
FIG. 22 is a diagram illustrating a non-limiting example of a workflow for performing a screening assay for a functional bispecific or multispecific biologic in a compartmentalized nano-volume, which involves using a yeast cell expressing single variants of a biologic.

FIG. 22 illustrates an example process 1200 in accordance with an implementation of the present disclosure. Process 1200 may represent an aspect of implementing the proposed concepts and schemes such as one or more of the various schemes, concepts and examples described above with respect to FIG. 1-FIG. 18. More specifically, process 1200 may represent an aspect of the proposed concepts and schemes pertaining to compartmentalized nano-volume based assays to directly and rapidly screen for functional single variants from an engineered library of bispecific or multispecific biologics in an ultra-high throughput manner. Process 1200 may include one or more operations, actions, or functions as illustrated by one or more of blocks 1210, 1220, 1230, 1240, 1250, 1260, 1270, 1280, 1290 and 1295. Although illustrated as discrete blocks, various blocks of process 1100 may be divided into additional blocks, combined into fewer blocks, or eliminated, depending on the desired implementation. Moreover, the blocks of process 1200 may be executed in the order shown in FIG. 22 or, alternatively in a different order. Furthermore, the blocks of process 1100 may be executed iteratively. Process 1200 may begin at block 1210.

At 1210, process 1200 may involve providing a genetic-variant DNA library 1, wherein each variant encodes at least one moiety or moieties of a bispecific or multispecific biologic. Process 1200 may proceed from 1210 to 1230.

At 1220, which may be performed in parallel with 1210, process 1200 may involve providing a genetic-variant DNA library 2, wherein each variant encodes all remaining necessary moieties of a bispecific or multispecific biologic. Process 1200 may proceed from 1220 to 1240.

At 1230, process 1200 may involve transforming the DNA library 1 obtained at 1210 into a plurality of haploid yeast cells with Mat a genotype to obtain a haploid yeast library 1. Process 1200 may proceed from 1230 to 1250.

At 1240, process 1200 may involve transforming the DNA library 2 obtained at 1220 into a plurality of haploid yeast cells with Mat a genotype to obtain a haploid yeast library 2. Process 1200 may proceed from 1230 to 1250.

At 1250, process 1200 may involve mating the yeast library 1 and 2 of complementary mating types to obtain a diploid yeast library, wherein each diploid yeast cell expresses and secretes substantially a single-variant of the said biologic. Process 1200 may proceed from 1250 to 1270.

At 1270, process 1200 may involve obtaining a plurality of nano-volumes (droplets or microchambers) that are compartmentalized with substantially 1 biologic-expressing diploid yeast cell from engineered cell library 2, and reporter cells provided in parallel at block 1260. Process 1200 may proceed from 1270 to 1280.

At 1280, process 1200 may involve performing sample incubation and optical detection of reporter signals. Process 1000 may proceed from 1280 to 1290.

At 1290, process 1200 may involve processing signal detection data and recovering reporter-positive yeast cells. Process 1000 may proceed from 1290 to 1295.

At 1295, process 1200 may involve identifying genetic sequence of individual biologic variants from the recovered diploid yeast cells.

Non-Limiting and Illustrative Processes

Figure 23:
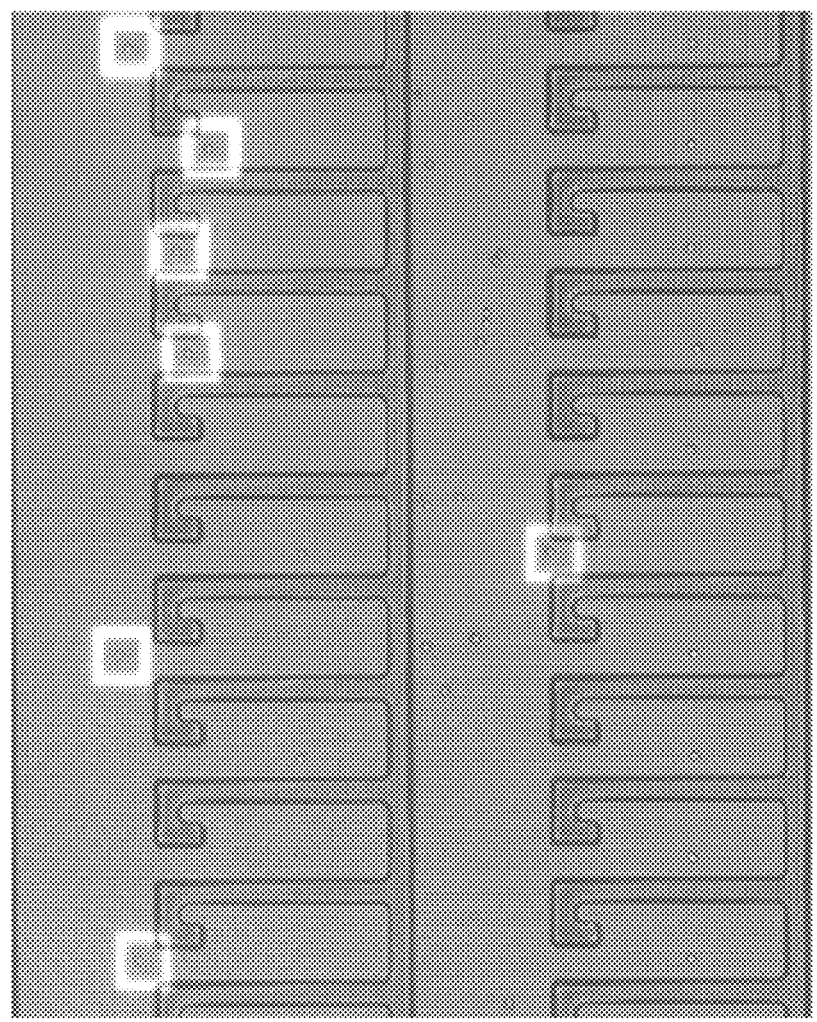
FIG. 23. Semi-enclosed microchamber device containing NANOPENS™ microchambers (e.g., Berkeley Lights Inc. OPTOSELECT™ device).

Several embodiments utilize a droplet-based compartmentalization platform. Some embodiments utilize a semi-enclosed microchamber format. For example, a semi-enclosed microchamber device is depicted in FIG. 23. In the Berkeley Lights Inc. OptoSelect™ device (see the World-Wide-Web at Berkeleylights.com), each has platform with a few thousand or more microchambers that are semi-enclosed (so called NANOPENS™). Each individual cell can be precisely "moved" into/out of a NANOPENS™ by a controlled laser light. Cells are cloned and assayed in individual 500 pL or 1 nL NANOPENS™. Each pen is about 100,000 times smaller than a microwell.

Figure 24:
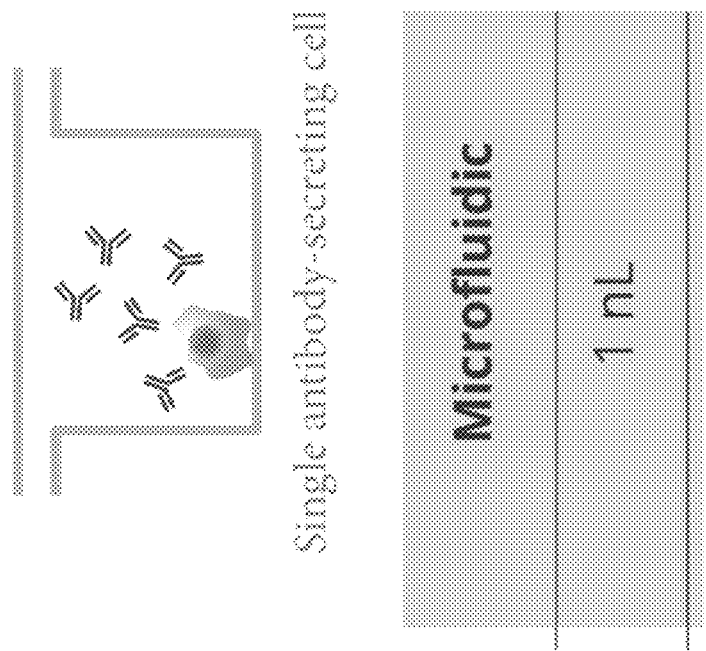
FIG. 24. Semi-enclosed microchamber device, enclosed by a thin film or a plastic layer (e.g., Single Cell Technologies' microfluidic devices (USA)).

Other devices are provided by Abcellera Biologics (Canada) on the World-Wide-Web at: abcellera.com, Xcella Biosciences (USA) on the World-Wide-Web at xcellabio.com, and Single Cell Technologies (USA). In these devices, each device has about 20,000, 30,000, 40,000, 50,000 or more microchambers or "micro-pores" that are also semi-enclosed (see FIG. 24), each chamber having a volume of about 0.5 nL to about 4 nL, where the top of the device is a thin film, a layer of polymeric plastic, or a layer of hydrophobic oil. Individual cells randomly or in a controlled manner flow into and fill the chambers, and can be recovered by an established method, e.g., by applying a needle directly from the device top film to suck the cell(s) out.

Alternative Cell Library Designs

In several embodiments, all components (subunits) encoding the biologic are integrated into cell-1 (see, for example, FIG. 1). In some embodiments, all components (subunits) encoding the biologic are integrated into cell-1 (see FIG. 25).

In several embodiments, the reporter cell comprises a genetically engineered fluorescent protein/complex or a luciferase or luminogenic protein that can be activated by a functional biologic (bispecific or multispecific).

In several embodiments, a genetically engineered effector protein can be optically detected by using a fluorescent probe(s) that bind to the effector molecules (e.g., modular sensor proteins (extracellular, intracellular, or cell-surface based).

In several embodiments, an endogenous effector molecule can be activated or upregulated by a functional biologics. The effector molecule can be optically detected by using a fluorescent probe(s). Such effector molecule can be expressed on a cell surface or inside a cell, e.g., endogenous GPCR can be activated, leading to upregulation of effector molecules including 2nd messengers (cAMP and calcium). These effector molecules ("reporter molecules") can be optically detected using fluorescent or luminogenic molecules.

In additional reporter cell embodiments, multi-step detection schemes may be employed, for example: (1): detecting the binding of a biologic to targets (similar to Flow Cytometry), (2) recovery of cells, and (3) analysis by linkage PCR and sequencing.

Figure 26:
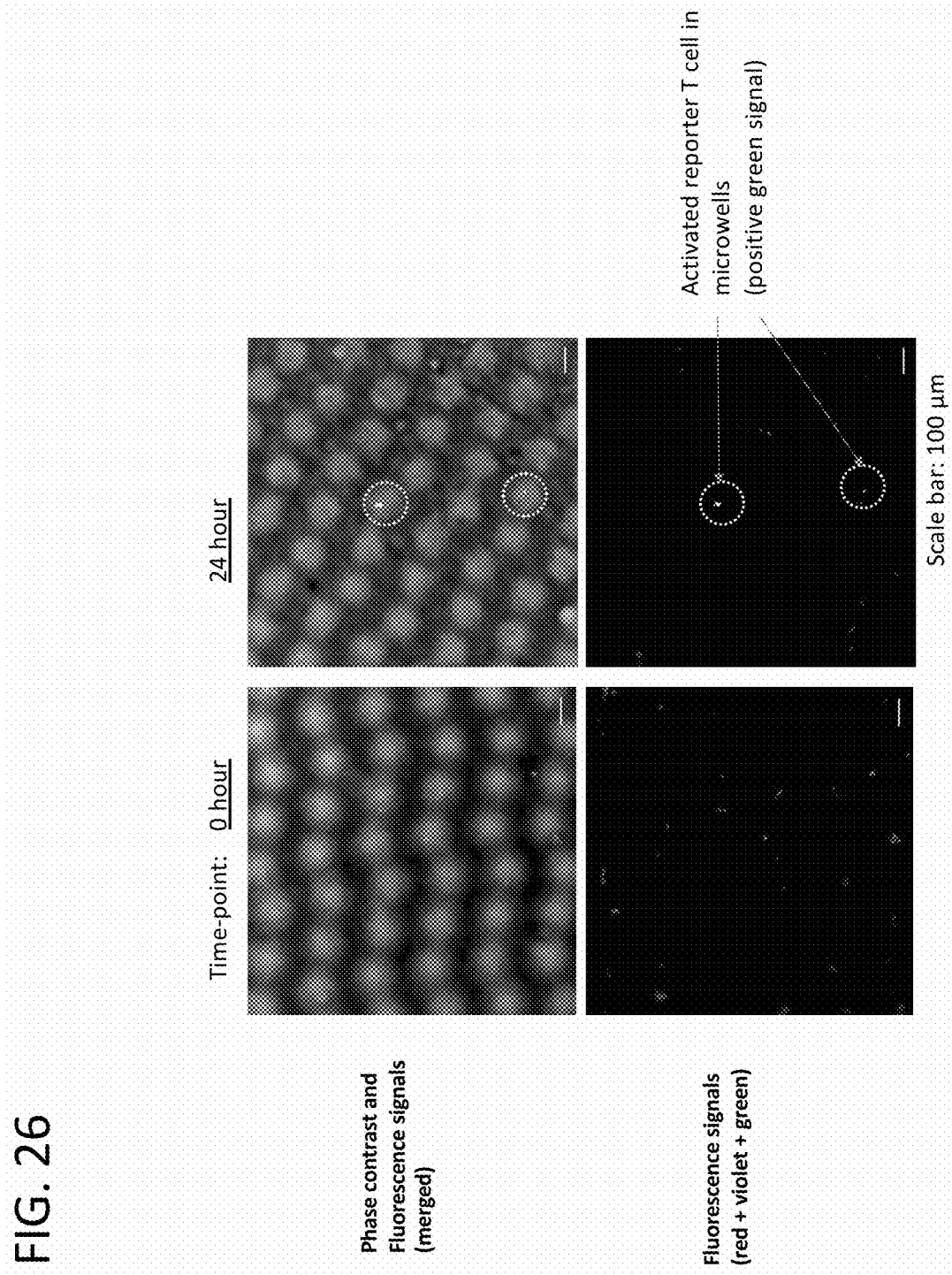
FIG. 26 depicts an alternative microchamber-like device that is printed with a biodegradable soft-solid polymer material by using a 3D printer.

In another embodiment, FIG. 26 depicts an alternative microchamber-like device that is printed with a biodegradable soft-solid polymer material by using a 3D printer. This device contains thousands of cylindrical microwells (height: 100 μm×diameter 100 μm), which are optionally enclosed by a layer of mineral oil or film, where a plurality of such microwells are provided with substantially a target cell ($CD19^+$ leukemia cell, Raji) and one or more reporter cells (a Jurkat-derived reporter T cell), plus Blinatumomab, a CD3×CD19 bispecific molecule (or BiTE). Functional cross-linking between CD3 and CD19 by the CD3×CD19 bispecific molecule activates the transcription and expression of the reporter molecule, which is a zsGreen fluorescent protein driven by a NFAT-responsive regulatory element.

Raji cells were stained with CellTrace Violet (blue fluorescence) and Jurkat cells with CellTrace Far Red (red fluorescence). As a control, the reporter cells are not activated in microchamber wells without the target cells.

Although some embodiments are disclosed above, they are not intended to limit the scope of the present disclosure. It will be apparent to those skilled in the art that various modifications and variations can be made to the disclosed embodiments of the present disclosure without departing from the scope or spirit of the present disclosure. In view of the foregoing, the scope of the present disclosure shall be defined by the following claims and their equivalents.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although embodiments of the inventions disclosed herein have been disclosed in the context of certain preferred embodiments and examples, it will be understood by those skilled in the art that the present inventions extend beyond the specifically disclosed embodiments to other alternative embodiments and/or uses of the various inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method for performing assays in compartmentalized nano-volumes to screen for functional bispecific or multispecific biologics, comprising:
   (a) obtaining a plurality of at least two distinct types of cells, wherein a first-type of cells are engineered to express a single genetic-variant per cell of a bispecific or multispecific biologic in a secreted form, and wherein a second-type of cells are selected or engineered to produce a positive reporter molecule signal that is triggered by a functional variant of the bispecific or multispecific biologic expressed from the single genetic-variant by the first-type cell, wherein the bispecific or multispecific biologic comprises:
      (i) a first target-binding moiety configured to bind to a first target molecule selected from the group consisting of a cytokine or a cytokine-like polypeptide, an extracellular fragment of a cell surface protein, a chemokine and a chemokine-like molecule, wherein the first target molecule is on either the first type of cells or the second type of cells, and
      (ii) a second target-binding moiety that is configured to bind to a second target molecule, wherein, if the first target molecule is on the second type of cells, the second target molecule is on the first type of cells and if the first target molecule is on the first type of cells, the second target molecule is on the second type of cells, wherein the bispecific or multispecific biologic connects the cell of the first type to the cell of the second type;
   (b) co-encapsulating into each of a plurality of compartmentalized nano-volumes only one cell of the first-type cell and one or more cell(s) of the second-type cell;
   (c) incubating the nano-volumes over a period of time sufficient to allow the expression and secretion of the bispecific or multispecific biologic and expression of the positive reporter molecule signal inside the nano-volumes;

(d) collecting data representing a positive reporter molecule signal triggered by the secreted bispecific or multispecific biologics inside the nano-volumes, (e) recovering the first type of cells from the nano-volumes that exhibit a positive reporter molecule signal, and (f) extracting from the recovered first type of cells genetic information representing respective functional variants of the bispecific or multispecific biologics.

2. The method of claim 1, wherein the second target-binding moiety is selected from the group consisting of an IgG heavy chain, an IgG light chain, a scFv, a Fab, a Fab', a F(ab')$_2$, a single domain antibody, a VHH domain antibody and a nanobody, wherein the first target-binding moiety is fused to a carboxy terminal end of an immunoglobulin heavy chain molecule, and wherein the second target-binding moiety comprises the amino terminal, variable region of the heavy chain molecule combined with variable region of an immunoglobulin light chain molecule.

3. The method of claim 1, wherein the first target-binding moiety and the second target-binding moiety of the bispecific or multispecific biologic are each configured to bind to a cytokine or a cytokine-like polypeptide, an extracellular fragment of a cell surface protein, a chemokine or a chemokine-like molecule.

4. The method of claim 1, wherein the compartmentalized nano-volumes are individual semi-enclosed microchambers and wherein the two distinct types of cells are introduced into the individual semi-enclosed microchambers via sequential steps.

5. A method for performing assays in compartmentalized nano-volumes to screen for functional bispecific or multispecific biologics, comprising:

(a) obtaining a plurality of at least two distinct types of cells, wherein a first-type of cells are engineered to express a single genetic-variant per cell of a bispecific or multispecific biologic in a secreted form, and wherein a second-type of cells are selected or engineered to produce a positive reporter molecule signal that is triggered by a functional variant of the bispecific or multispecific biologic expressed from the single genetic-variant by the first-type cell, wherein the bispecific or multispecific biologic comprises:

(i) a first target-binding moiety configured to bind to a target molecule on either the first type of cells or the second type of cells, and (ii) a second target-binding moiety configured to bind to:

(1) a target molecule on the second type of cells if the first target-binding moiety is configured to bind to the first type of cells; or (2) a target molecule on the first type of cells if the first target-binding moiety is configured to bind to the second type of cells;

(b) co-encapsulating into each of a plurality of compartmentalized nano-volumes only one cell of the first-type cell and one or more cell(s) of the second-type cell;

(c) incubating the nano-volumes over a period of time sufficient to allow the expression and secretion of the bispecific or multispecific biologic and binding of the bispecific or multispecific biologic to the first type of cell and to one of the second type cell, wherein binding to both cell types is required to induce expression of the positive reporter molecule signal inside the nano-volumes;

(d) collecting data representing a positive reporter molecule signal triggered by the secreted bispecific or multispecific biologics inside the nano-volumes, (e) recovering the first type of cells from the nano-volumes that exhibit a positive reporter molecule signal, and (f) extracting from the recovered first type of cells genetic information representing respective functional variants of the bispecific or multispecific biologics.

6. The method of claim 5, wherein the compartmentalized nano-volumes are individual semi-enclosed microchambers and wherein the two distinct types of cells are introduced into the individual semi-enclosed microchambers via sequential steps.

7. The method of claim 1, wherein the compartmentalized nano-volumes are microchambers or droplets with a homogeneous or near-homogeneous size of about 0.03 nL to about 100 nL, or of about 0.1 nL to about 4 nL.

8. The method of claim 1, wherein target-binding moieties of the said biologic are linked by at least one non-target-binding moiety, which is selected from a group consisting of a heterodimerization domain, a hetero-trimerization domain and a linker peptide with a length of about 2 to about 30 amino acids or of about 10 to about 50 amino acids.

9. The method of claim 1, wherein the first-type cell is engineered with substantially one or two distinct expression cassettes or vehicles that are integrated into the genome of the first-type cell, which express a single genetic-variant of the said biologic from the integrated expression cassettes or vehicles.

10. The method of claim 1, wherein the reporter molecule in the second-type cell is a fluorescent protein, a fluorogenic molecule, a fluorescent molecule or complex, or a FRET pair.

11. The method of claim 1, wherein the reporter molecule in the second cell is a luciferase, a luminogenic molecule or complex.

12. The method according to claim 11, wherein the reporter molecule is an effector molecule downstream of a cell-surface target comprised by the second-type cell.

13. The method of claim 1, wherein collecting data that represent the positive reporter molecule signal is through detecting a reporter-derived optical signal using an optical detection device.

14. The method of claim 1, wherein the bispecific or multispecific biologic binds to two or more distinct target molecules on the second-type cell(s) in the compartmentalized nano-volume.

15. The method of claim 1, wherein the bispecific or multispecific biologic further binds to a target molecule on the first-type cell in the compartmentalized nano-volume.

16. A method for performing assays in compartmentalized nano-volumes to screen for functional bispecific or multispecific biologics, comprising:

(a) obtaining a plurality of at least two distinct types of cells, wherein a first-type of cells are engineered to express a single genetic-variant per cell of a bispecific or multispecific biologic in a secreted form, and wherein a second-type of cells are selected or engineered to produce a positive reporter molecule signal that is triggered by a functional variant of the bispecific or multispecific biologic expressed from the single genetic-variant by the first-type cell, wherein the bispecific or multispecific biologic comprises:

(1) a first target-binding moiety that binds to a G Protein Coupled Receptor (GPCR) on either the first type of cells or the second type of cells, and
(2) a second target-binding moiety that is configured to bind to a different target molecule on either the first type of cells or a target molecule on the second type of cells, wherein, if the first target molecule is on the second type of cells, the second target molecule is on the first type of cells, and if the first target molecule is on the first type of cells, the second target molecule is on the second type of cells, wherein the bispecific or multispecific biologic connects the cell of the first type to the cell of the second type;
(b) co-encapsulating into each of a plurality of compartmentalized nano-volumes only one cell of the first-type cell and one or more cell(s) of the second-type cell;
(c) incubating the nano-volumes over a period of time sufficient to allow the expression and secretion of the bispecific or multispecific biologic and expression of the positive reporter molecule signal inside the nano-volumes;
(d) collecting data representing a positive reporter molecule signal triggered by the secreted bispecific or multispecific biologics inside the nano-volumes,
(e) recovering the first type of cells from the nano-volumes that exhibit a positive reporter molecule signal, and
(f) extracting from the recovered first type of cells genetic information representing respective functional variants of the bispecific or multispecific biologics.

17. The method of claim 16, wherein the second target-binding moiety is selected from the group consisting of an IgG heavy chain, an IgG light chain, a scFv, a Fab, a Fab', a F(ab')$_2$, a single domain antibody, a VHH domain antibody and a nanobody, wherein the first target-binding moiety is fused to a carboxy terminal end of an immunoglobulin heavy chain molecule, and wherein the second target-binding moiety comprises the amino terminal, variable region of the heavy chain molecule combined with variable region of an immunoglobulin light chain molecule.

18. The method of claim 16, wherein the compartmentalized nano-volumes are individual semi-enclosed microchambers and wherein the two distinct types of cells are introduced into the individual semi-enclosed microchambers via sequential steps.

19. The method of claim 16, wherein the compartmentalized nano-volumes are microchambers or droplets with a homogeneous or near-homogeneous size of about 0.03 nL to about 100 nL, or of about 0.1 nL to about 4 nL.

20. The method of claim 16, wherein target-binding moieties of the said biologic are linked by at least one non-target-binding moiety, which is selected from a group consisting of a heterodimerization domain, a hetero-trimerization domain and a linker peptide with a length of about 2 to about 30 amino acids or of about 10 to about 50 amino acids.

21. The method of claim 16, wherein the first-type cell is engineered with substantially one or two distinct expression cassettes or vehicles that are integrated into the genome of the first-type cell, which express a single genetic-variant of the said biologic from the integrated expression cassettes or vehicles.

22. The method of claim 16, wherein the reporter molecule in the second-type cell is a fluorescent protein, a fluorogenic molecule, a fluorescent molecule or complex, or a FRET pair.

23. The method of claim 16, wherein the reporter molecule in the second cell is a luciferase, a luminogenic molecule or complex.

24. The method according to claim 16, wherein the reporter molecule is an effector molecule downstream of a cell-surface target comprised by the second-type cell.

25. The method of claim 16, wherein collecting data that represent the positive reporter molecule signal is through detecting a reporter-derived optical signal using an optical detection device.

26. The method of claim 16, wherein the bispecific or multispecific biologic binds to two or more distinct target molecules on the second-type cell(s) in the compartmentalized nano-volume.

27. The method of claim 26, wherein the bispecific or multispecific biologic further binds to a target molecule on the first-type cell in the compartmentalized nano-volume.

* * * * *